(12) United States Patent
Barrio García et al.

(10) Patent No.: US 11,702,692 B2
(45) Date of Patent: Jul. 18, 2023

(54) METHOD OF TREATMENT OF DISEASE AND METHOD FOR QUANTIFYING THE LEVEL OF MINIMAL RESIDUAL DISEASE IN A SUBJECT

(71) Applicant: FUNDACIÓN DE INVESTIGACIÓN HOSPITAL 12 DE OCTUBRE, Madrid (ES)

(72) Inventors: Santiago Barrio García, Madrid (ES); Joaquín Martínez López, Madrid (ES); Carlos Marín Sebastián, Madrid (ES); María Inmaculada Rapado Martínez, Madrid (ES); Rosa María Ayala Díaz, Madrid (ES); Beatriz Sánchez Vega Carrión, Madrid (ES)

(73) Assignee: FUNDACIÓN DE INVESTIGACIÓN HOSPITAL 12 DE OCTUBRE

( * ) Notice: Subject to any disclaimer, the term of this patent is extended or adjusted under 35 U.S.C. 154(b) by 973 days.

(21) Appl. No.: 15/932,273

(22) Filed: Feb. 16, 2018

(65) Prior Publication Data

US 2019/0017114 A1   Jan. 17, 2019

Related U.S. Application Data

(60) Continuation-in-part of application No. 15/848,718, filed on Dec. 20, 2017, now abandoned, and a division of application No. 14/932,267, filed on Nov. 4, 2015, now abandoned.

(30) Foreign Application Priority Data

Nov. 5, 2014   (EP) .................................... 14191967

(51) Int. Cl.
| | | |
|---|---|---|
| *C12Q 1/6874* | (2018.01) | |
| *C12Q 1/6806* | (2018.01) | |
| *C12Q 1/6883* | (2018.01) | |
| *C12Q 1/6886* | (2018.01) | |
| *G16B 25/20* | (2019.01) | |
| *G16B 30/10* | (2019.01) | |
| *G16B 20/00* | (2019.01) | |
| *G16B 30/00* | (2019.01) | |

(52) U.S. Cl.
CPC ......... *C12Q 1/6874* (2013.01); *C12Q 1/6806* (2013.01); *C12Q 1/6883* (2013.01); *C12Q 1/6886* (2013.01); *G16B 20/00* (2019.02); *G16B 25/20* (2019.02); *G16B 30/10* (2019.02); *C12Q 2600/106* (2013.01); *C12Q 2600/118* (2013.01); *C12Q 2600/156* (2013.01); *G16B 30/00* (2019.02)

(58) Field of Classification Search
None
See application file for complete search history.

(56) References Cited

U.S. PATENT DOCUMENTS

| | | |
|---|---|---|
| 2014/0235454 A1 | 8/2014 | Faham et al. |
| 2016/0122819 A1 | 5/2016 | Barrio Garcia et al. |
| 2018/0012782 A1 | 1/2018 | Balucani |

FOREIGN PATENT DOCUMENTS

WO   2014062945 A1   4/2014

OTHER PUBLICATIONS

Faham, Malek, et al.; "Deep-sequencing approach for minimal residual disease detection in acute lymphoblastic leukemia," Blood, 2012, pp. 5173-5180, vol. 120.

(Continued)

*Primary Examiner* — G Steven Vanni
(74) *Attorney, Agent, or Firm* — Tristan A. Fuierer; Casimir Jones SC

(57) ABSTRACT

The present invention belongs to the field of diagnosis of disease. Thus the present invention is focused on a method and kit and system for quantifying the level of minimal residual disease (MRD) in a subject who has been treated for said disease, as well as a method of treatment of said disease in a subject which comprises a step of quantifying the level of minimal residual diseases, wherein said quantifying comprises:
(a) identifying, amplifying and sequencing a nucleotide sequence in a biological sample obtained from said subject after treatment for said disease, wherein the gDNA of said biological sample has an average weight, k, per cell, and wherein said nucleotide sequence is identified using primers and is amplified using an amount, D, to afford a first list of characters;
(b) identifying, amplifying and sequencing a nucleotide sequence in a biological sample obtained from a subject with said disease using the same primers as in step (a) to afford a second list of characters;
(c) determining, for each first list of characters obtained in step (a), the degree of similarity, DS, with each second list of characters obtained in step (b);
(d) selecting, for each first list of characters obtained in step (a), the DS of highest value, $DS_{HV}$;
(e) adding up the number of first lists of characters obtained in step (a) which have a $DS_{HV}$ that is greater than a threshold value, T, to obtain $L_c$;
(f) adding up the total number of lists of characters, $L_t$, in the first list of characters; and
(g) calculating the level of minimal residual disease (MRD) according to either of the following formulae:

$$MRD = (L_c \times k)/(L_t \times D)$$

or $$MRD = L_c/L_t$$

or $$MRD = L_c \times (D/k)/L_t^2.$$

15 Claims, 31 Drawing Sheets

Specification includes a Sequence Listing.

(56) References Cited

OTHER PUBLICATIONS

Martinez-Lopez, Joaquin, et al.; "Prognostic value of deep sequencing method for minimal residual disease detection in multiple myeloma," Blood, 2014, pp. 3073-3079, vol. 123.
Extended European Search Report, dated Mar. 4, 2015.
Martinez-Lopez, J.; Leukemia (2017); vol. 31, pp. 1446-1449; doi:10.1038/leu.2017.58, preview online Feb. 17, 2017.

Figure 3 xi)
xii)
xiii)
xiv)
xv) repeat xiii)
xv) repeat xiv)
xv) repeat xiii)
xv) repeat xiv)
xv) repeat xiii)
xv) repeat xiv)

*etc.*

A

B

```
                         SEQUENCE LISTING

<160> NUMBER OF SEQ ID NOS: 153

<210> SEQ ID NO 1
<211> LENGTH: 25
<212> TYPE: DNA
<213> ORGANISM: Artificial Sequence
<220> FEATURE:
<223> OTHER INFORMATION: Primer VH1-FR1

<400> SEQUENCE: 1
ggcctcagtg aaggtctcct gcaag                                            25

<210> SEQ ID NO 2
<211> LENGTH: 25
<212> TYPE: DNA
<213> ORGANISM: Artificial Sequence
<220> FEATURE:
<223> OTHER INFORMATION: Primer VH2-FR1

<400> SEQUENCE: 2
gtctggtcct acgctggtga aaccc                                            25

<210> SEQ ID NO 3
<211> LENGTH: 25
<212> TYPE: DNA
<213> ORGANISM: Artificial Sequence
<220> FEATURE:
<223> OTHER INFORMATION: Primer VH3-FR1

<400> SEQUENCE: 3 ctgggggtc cctgagactc tcctg                                             25

<210> SEQ ID NO 4
<211> LENGTH: 25
<212> TYPE: DNA
<213> ORGANISM: Artificial Sequence
<220> FEATURE:
<223> OTHER INFORMATION: Primer VH4-FR1

<400> SEQUENCE: 4
cttcggagac cctgtccctc acctg                                            25

<210> SEQ ID NO 5
<211> LENGTH: 25
<212> TYPE: DNA
<213> ORGANISM: Artificial Sequence
<220> FEATURE:
<223> OTHER INFORMATION: Primer VH5-FR1

<400> SEQUENCE: 5
cggggagtct ctgaagatct cctgt                                            25

<210> SEQ ID NO 6
<211> LENGTH: 25
<212> TYPE: DNA
<213> ORGANISM: Artificial Sequence
<220> FEATURE:
<223> OTHER INFORMATION: Primer VH6-FR1

<400> SEQUENCE: 6
```

-continued tcgcagaccc tctcactcac ctgtg        25

<210> SEQ ID NO 7
<211> LENGTH: 25
<212> TYPE: DNA
<213> ORGANISM: Artificial Sequence
<220> FEATURE:
<223> OTHER INFORMATION: Primer VH1-FR2

<400> SEQUENCE: 7
ctgggtgcga caggcccctg gacaa        25

<210> SEQ ID NO 8
<211> LENGTH: 25
<212> TYPE: DNA
<213> ORGANISM: Artificial Sequence
<220> FEATURE:
<223> OTHER INFORMATION: Primer VH2-FR2

<400> SEQUENCE: 8
tggatccgtc agcccccagg gaagg        25

<210> SEQ ID NO 9
<211> LENGTH: 21
<212> TYPE: DNA
<213> ORGANISM: Artificial Sequence
<220> FEATURE:
<223> OTHER INFORMATION: Primer VH3-FR2

<400> SEQUENCE: 9
ggtccgccag gctccaggga a        21

<210> SEQ ID NO 10
<211> LENGTH: 25
<212> TYPE: DNA
<213> ORGANISM: Artificial Sequence
<220> FEATURE:
<223> OTHER INFORMATION: Primer VH4-FR2

<400> SEQUENCE: 10
tggatccgcc agcccccagg gaagg        25

<210> SEQ ID NO 11
<211> LENGTH: 25
<212> TYPE: DNA
<213> ORGANISM: Artificial Sequence
<220> FEATURE:
<223> OTHER INFORMATION: Primer VH5-FR2

<400> SEQUENCE: 11
gggtgcgcca gatgcccggg aaagg        25

<210> SEQ ID NO 12
<211> LENGTH: 25
<212> TYPE: DNA
<213> ORGANISM: Artificial Sequence
<220> FEATURE:
<223> OTHER INFORMATION: Primer VH6-FR2

<400> SEQUENCE: 12
tggatcaggc agtccccatc gagag        25

<210> SEQ ID NO 13
<211> LENGTH: 25
<212> TYPE: DNA
<213> ORGANISM: Artificial Sequence

```
<220> FEATURE:
<223> OTHER INFORMATION: Primer VH7-FR2

<400> SEQUENCE: 13
ttgggtgcga caggcccctg gacaa                                              25

<210> SEQ ID NO 14
<211> LENGTH: 25
<212> TYPE: DNA
<213> ORGANISM: Artificial Sequence
<220> FEATURE:
<223> OTHER INFORMATION: Primer VH1-FR3

<400> SEQUENCE: 14
tggagctgag cagcctgaga tctga                                              25

<210> SEQ ID NO 15
<211> LENGTH: 25
<212> TYPE: DNA
<213> ORGANISM: Artificial Sequence
<220> FEATURE:
<223> OTHER INFORMATION: Primer VH2-FR3

<400> SEQUENCE: 15
caatgaccaa catggaccct gtgga                                              25

<210> SEQ ID NO 16
<211> LENGTH: 25
<212> TYPE: DNA
<213> ORGANISM: Artificial Sequence
<220> FEATURE:
<223> OTHER INFORMATION: Primer VH3-FR3

<400> SEQUENCE: 16
tctgcaaatg aacagcctga gagcc                                              25

<210> SEQ ID NO 17
<211> LENGTH: 25
<212> TYPE: DNA
<213> ORGANISM: Artificial Sequence
<220> FEATURE:
<223> OTHER INFORMATION: Primer VH4-FR3

<400> SEQUENCE: 17
gagctctgtg accgccgcgg acacg                                              25

<210> SEQ ID NO 18
<211> LENGTH: 25
<212> TYPE: DNA
<213> ORGANISM: Artificial Sequence
<220> FEATURE:
<223> OTHER INFORMATION: Primer VH5-FR3

<400> SEQUENCE: 18
cagcaccgcc tacctgcagt ggagc                                              25

<210> SEQ ID NO 19
<211> LENGTH: 25
<212> TYPE: DNA
<213> ORGANISM: Artificial Sequence
<220> FEATURE:
<223> OTHER INFORMATION: Primer VH6-FR3

<400> SEQUENCE: 19
gttctccctg cagctgaact ctgtg                                              25
```

<210> SEQ ID NO 20
<211> LENGTH: 24
<212> TYPE: DNA
<213> ORGANISM: Artificial Sequence
<220> FEATURE:
<223> OTHER INFORMATION: Primer VH7-FR3

<400> SEQUENCE: 20
cagcacggca tatctgcaga tcag                                         24

<210> SEQ ID NO 21
<211> LENGTH: 18
<212> TYPE: DNA
<213> ORGANISM: Artificial Sequence
<220> FEATURE:
<223> OTHER INFORMATION: Primer DH1

<400> SEQUENCE: 21
ggcggaatgt gtgcaggc                                                18

<210> SEQ ID NO 22
<211> LENGTH: 21
<212> TYPE: DNA
<213> ORGANISM: Artificial Sequence
<220> FEATURE:
<223> OTHER INFORMATION: Primer DH2

<400> SEQUENCE: 22
gcactgggct cagagtcctc t                                            21

<210> SEQ ID NO 23
<211> LENGTH: 20
<212> TYPE: DNA
<213> ORGANISM: Artificial Sequence
<220> FEATURE:
<223> OTHER INFORMATION: Primer DH3

<400> SEQUENCE: 23
gtggccctgg gaatataaaa                                              20

<210> SEQ ID NO 24
<211> LENGTH: 19
<212> TYPE: DNA
<213> ORGANISM: Artificial Sequence
<220> FEATURE:
<223> OTHER INFORMATION: Primer DH4

<400> SEQUENCE: 24
agatccccag gacgcagca                                               19

<210> SEQ ID NO 25
<211> LENGTH: 20
<212> TYPE: DNA
<213> ORGANISM: Artificial Sequence
<220> FEATURE:
<223> OTHER INFORMATION: Primer DH5

<400> SEQUENCE: 25 caggggggaca ctgtgcatgt                                             20

<210> SEQ ID NO 26
<211> LENGTH: 19
<212> TYPE: DNA
<213> ORGANISM: Artificial Sequence
<220> FEATURE:
<223> OTHER INFORMATION: Primer DH6

```
<400> SEQUENCE: 26 tgacccccagc aagggaagg                                                    19

<210> SEQ ID NO 27
<211> LENGTH: 18
<212> TYPE: DNA
<213> ORGANISM: Artificial Sequence
<220> FEATURE:
<223> OTHER INFORMATION: Primer DH7

<400> SEQUENCE: 27
cacaggcccc ctaccagc                                                      18

<210> SEQ ID NO 28
<211> LENGTH: 22
<212> TYPE: DNA
<213> ORGANISM: Artificial Sequence
<220> FEATURE:
<223> OTHER INFORMATION: Primer JH57

<400> SEQUENCE: 28
cttacctgag gagacggtga cc                                                 22

<210> SEQ ID NO 29
<211> LENGTH: 25
<212> TYPE: DNA
<213> ORGANISM: Artificial Sequence
<220> FEATURE:
<223> OTHER INFORMATION: Primer VK1f/6

<400> SEQUENCE: 29
tcaaggttca gcggcagtgg atctg                                              25

<210> SEQ ID NO 30
<211> LENGTH: 26
<212> TYPE: DNA
<213> ORGANISM: Artificial Sequence
<220> FEATURE:
<223> OTHER INFORMATION: Primer VK2f

<400> SEQUENCE: 30
ggcctccatc tcctgcaggt ctagtc                                             26

<210> SEQ ID NO 31
<211> LENGTH: 27
<212> TYPE: DNA
<213> ORGANISM: Artificial Sequence
<220> FEATURE:
<223> OTHER INFORMATION: Primer VK3f

<400> SEQUENCE: 31
cccaggctcc tcatctatga tgcatcc                                            27

<210> SEQ ID NO 32
<211> LENGTH: 27
<212> TYPE: DNA
<213> ORGANISM: Artificial Sequence
<220> FEATURE:
<223> OTHER INFORMATION: Primer VK4

<400> SEQUENCE: 32
caactgcaag tccagccaga gtgtttt                                            27

<210> SEQ ID NO 33
```

```
<211> LENGTH: 26
<212> TYPE: DNA
<213> ORGANISM: Artificial Sequence
<220> FEATURE:
<223> OTHER INFORMATION: Primer VK5

<400> SEQUENCE: 33
cctgcaaagc cagccaagac attgat                                          26

<210> SEQ ID NO 34
<211> LENGTH: 27
<212> TYPE: DNA
<213> ORGANISM: Artificial Sequence
<220> FEATURE:
<223> OTHER INFORMATION: Primer VK6

<400> SEQUENCE: 34
gaccgatttc accctcacaa ttaatcc                                         27

<210> SEQ ID NO 35
<211> LENGTH: 27
<212> TYPE: DNA
<213> ORGANISM: Artificial Sequence
<220> FEATURE:
<223> OTHER INFORMATION: Primer JK1-4

<400> SEQUENCE: 35
cttacgtttg atctccacct tggtccc                                         27

<210> SEQ ID NO 36
<211> LENGTH: 27
<212> TYPE: DNA
<213> ORGANISM: Artificial Sequence
<220> FEATURE:
<223> OTHER INFORMATION: Primer JK5

<400> SEQUENCE: 36
cttacgttta atctccagtc gtgtccc                                         27

<210> SEQ ID NO 37
<211> LENGTH: 27
<212> TYPE: DNA
<213> ORGANISM: Artificial Sequence
<220> FEATURE:
<223> OTHER INFORMATION: Primer Kde

<400> SEQUENCE: 37
cctcagaggt cagagcaggt tgtccta                                         27

<210> SEQ ID NO 38
<211> LENGTH: 22
<212> TYPE: DNA
<213> ORGANISM: Artificial Sequence
<220> FEATURE:
<223> OTHER INFORMATION: Primer INTR

<400> SEQUENCE: 38
cgtggcaccg cgagctgtag ac                                              22

<210> SEQ ID NO 39
<211> LENGTH: 21
<212> TYPE: DNA
<213> ORGANISM: Artificial Sequence
<220> FEATURE:
<223> OTHER INFORMATION: Primer 2VH1-1

<400> SEQUENCE: 39
```

```
caagggcttg agtggatggg a                                           21

<210> SEQ ID NO 40
<211> LENGTH: 24
<212> TYPE: DNA
<213> ORGANISM: Artificial Sequence
<220> FEATURE:
<223> OTHER INFORMATION: Primer 2VH1-2

<400> SEQUENCE: 40
caacgccttg agtggatagg atgg                                        24

<210> SEQ ID NO 41
<211> LENGTH: 26
<212> TYPE: DNA
<213> ORGANISM: Artificial Sequence
<220> FEATURE:
<223> OTHER INFORMATION: Primer 2VH1-3

<400> SEQUENCE: 41
gacaagggct tgaaaggatg agatgg                                      26

<210> SEQ ID NO 42
<211> LENGTH: 17
<212> TYPE: DNA
<213> ORGANISM: Artificial Sequence
<220> FEATURE:
<223> OTHER INFORMATION: Primer 2VH2-1

<400> SEQUENCE: 42
gccctggagt ggcttgc                                                17

<210> SEQ ID NO 43
<211> LENGTH: 21
<212> TYPE: DNA
<213> ORGANISM: Artificial Sequence
<220> FEATURE:
<223> OTHER INFORMATION: Primer 2VH2-2

<400> SEQUENCE: 43
gaaggccctg gagtggattg c                                           21

<210> SEQ ID NO 44
<211> LENGTH: 18
<212> TYPE: DNA
<213> ORGANISM: Artificial Sequence
<220> FEATURE:
<223> OTHER INFORMATION: Primer 2VH3-1

<400> SEQUENCE: 44
ggaaggggct ggagtggg                                               18

<210> SEQ ID NO 45
<211> LENGTH: 19
<212> TYPE: DNA
<213> ORGANISM: Artificial Sequence
<220> FEATURE:
<223> OTHER INFORMATION: Primer 2VH3-9

<400> SEQUENCE: 45
gggaagggtc tggagtggg                                              19

<210> SEQ ID NO 46
<211> LENGTH: 25
<212> TYPE: DNA
```

```
<213> ORGANISM: Artificial Sequence
<220> FEATURE:
<223> OTHER INFORMATION: Primer 2VH3-11

<400> SEQUENCE: 46
gctacaggaa aaggtctgga gtggg                                              25

<210> SEQ ID NO 47
<211> LENGTH: 18
<212> TYPE: DNA
<213> ORGANISM: Artificial Sequence
<220> FEATURE:
<223> OTHER INFORMATION: Primer 2VH3-12

<400> SEQUENCE: 47
ggaagggcct ggagtggg                                                      18

<210> SEQ ID NO 48
<211> LENGTH: 20
<212> TYPE: DNA
<213> ORGANISM: Artificial Sequence
<220> FEATURE:
<223> OTHER INFORMATION: Primer 2VH3-13

<400> SEQUENCE: 48
ggagaagggg caggagtggg                                                    20

<210> SEQ ID NO 49
<211> LENGTH: 19
<212> TYPE: DNA
<213> ORGANISM: Artificial Sequence
<220> FEATURE:
<223> OTHER INFORMATION: Primer 2VH3-14

<400> SEQUENCE: 49
ggcaaggggc tagagtggg                                                     19

<210> SEQ ID NO 50
<211> LENGTH: 18
<212> TYPE: DNA
<213> ORGANISM: Artificial Sequence
<220> FEATURE:
<223> OTHER INFORMATION: Primer 2VH3-16

<400> SEQUENCE: 50
ggaaggggct ggtgtggg                                                      18

<210> SEQ ID NO 51
<211> LENGTH: 19
<212> TYPE: DNA
<213> ORGANISM: Artificial Sequence
<220> FEATURE:
<223> OTHER INFORMATION: Primer 2VH3-17

<400> SEQUENCE: 51
gggaaggggc tggaatggg                                                     19

<210> SEQ ID NO 52
<211> LENGTH: 25
<212> TYPE: DNA
<213> ORGANISM: Artificial Sequence
<220> FEATURE:
<223> OTHER INFORMATION: Primer 2VH3-18

<400> SEQUENCE: 52
gctacaggaa aaggtctgga atggg                                              25
```

<210> SEQ ID NO 53
<211> LENGTH: 20
<212> TYPE: DNA
<213> ORGANISM: Artificial Sequence
<220> FEATURE:
<223> OTHER INFORMATION: Primer 2VH3-19

<400> SEQUENCE: 53
agggaatggg ctggagttgg					20

<210> SEQ ID NO 54
<211> LENGTH: 20
<212> TYPE: DNA
<213> ORGANISM: Artificial Sequence
<220> FEATURE:
<223> OTHER INFORMATION: Primer 2VH3-21

<400> SEQUENCE: 54
agggaagggg ctggagtgag					20

<210> SEQ ID NO 55
<211> LENGTH: 18
<212> TYPE: DNA
<213> ORGANISM: Artificial Sequence
<220> FEATURE:
<223> OTHER INFORMATION: Primer 2VH3-22

<400> SEQUENCE: 55
ggaagggtcc ggagtggg					18

<210> SEQ ID NO 56
<211> LENGTH: 25
<212> TYPE: DNA
<213> ORGANISM: Artificial Sequence
<220> FEATURE:
<223> OTHER INFORMATION: Primer 2VH3-23

<400> SEQUENCE: 56
gctccaagaa agggtttgta gtggg					25

<210> SEQ ID NO 57
<211> LENGTH: 18
<212> TYPE: DNA
<213> ORGANISM: Artificial Sequence
<220> FEATURE:
<223> OTHER INFORMATION: Primer 2VH3-24

<400> SEQUENCE: 57
ggaaggggct ggagggag					18

<210> SEQ ID NO 58
<211> LENGTH: 25
<212> TYPE: DNA
<213> ORGANISM: Artificial Sequence
<220> FEATURE:
<223> OTHER INFORMATION: Primer 2VH3-25

<400> SEQUENCE: 58
gctccaggga agggactgga atatg					25

<210> SEQ ID NO 59
<211> LENGTH: 22
<212> TYPE: DNA
<213> ORGANISM: Artificial Sequence
<220> FEATURE:

```
<223> OTHER INFORMATION: Primer 2VH4-1

<400> SEQUENCE: 59
ggaagggact ggagtggatt gg                                         22

<210> SEQ ID NO 60
<211> LENGTH: 21
<212> TYPE: DNA
<213> ORGANISM: Artificial Sequence
<220> FEATURE:
<223> OTHER INFORMATION: Primer 2VH4-2

<400> SEQUENCE: 60
gaagggcctg gagtggattg g                                          21

<210> SEQ ID NO 61
<211> LENGTH: 21
<212> TYPE: DNA
<213> ORGANISM: Artificial Sequence
<220> FEATURE:
<223> OTHER INFORMATION: Primer 2VH4-3

<400> SEQUENCE: 61
gaagggyctg gagtggattg g                                          21

<210> SEQ ID NO 62
<211> LENGTH: 19
<212> TYPE: DNA
<213> ORGANISM: Artificial Sequence
<220> FEATURE:
<223> OTHER INFORMATION: Primer 2VH5-1

<400> SEQUENCE: 62
cctggagtgg atggggagg                                             19

<210> SEQ ID NO 63
<211> LENGTH: 20
<212> TYPE: DNA
<213> ORGANISM: Artificial Sequence
<220> FEATURE:
<223> OTHER INFORMATION: Primer 2VH5-2

<400> SEQUENCE: 63
gcctggagtg gatggggatc                                            20

<210> SEQ ID NO 64
<211> LENGTH: 24
<212> TYPE: DNA
<213> ORGANISM: Artificial Sequence
<220> FEATURE:
<223> OTHER INFORMATION: Primer 2VH5-3

<400> SEQUENCE: 64
gaaagaactg gagtggatgg ggag                                       24

<210> SEQ ID NO 65
<211> LENGTH: 20
<212> TYPE: DNA
<213> ORGANISM: Artificial Sequence
<220> FEATURE:
<223> OTHER INFORMATION: Primer 2VH6-4

<400> SEQUENCE: 65
aggcagtccc catcgagagg                                            20
```

```
<210> SEQ ID NO 66
<211> LENGTH: 23
<212> TYPE: DNA
<213> ORGANISM: Artificial Sequence
<220> FEATURE:
<223> OTHER INFORMATION: Primer 2VH7-5

<400> SEQUENCE: 66
agggctttga gtggatgtga tgg                                            23

<210> SEQ ID NO 67
<211> LENGTH: 22
<212> TYPE: DNA
<213> ORGANISM: Artificial Sequence
<220> FEATURE:
<223> OTHER INFORMATION: Primer 2VH7-6

<400> SEQUENCE: 67
agggcttgag tggatgggat gg                                             22

<210> SEQ ID NO 68
<211> LENGTH: 21
<212> TYPE: DNA
<213> ORGANISM: Artificial Sequence
<220> FEATURE:
<223> OTHER INFORMATION: Primer 3VH1-12

<400> SEQUENCE: 68
acgagcacag cctacatgga g                                              21

<210> SEQ ID NO 69
<211> LENGTH: 23
<212> TYPE: DNA
<213> ORGANISM: Artificial Sequence
<220> FEATURE:
<223> OTHER INFORMATION: Primer 3VH1-19

<400> SEQUENCE: 69
ccacaaccac agcctacaca gac                                            23

<210> SEQ ID NO 70
<211> LENGTH: 23
<212> TYPE: DNA
<213> ORGANISM: Artificial Sequence
<220> FEATURE:
<223> OTHER INFORMATION: Primer 3VH1-20

<400> SEQUENCE: 70
ccacgagcac agtctacatg gag                                            23

<210> SEQ ID NO 71
<211> LENGTH: 24
<212> TYPE: DNA
<213> ORGANISM: Artificial Sequence
<220> FEATURE:
<223> OTHER INFORMATION: Primer 3VH1-21

<400> SEQUENCE: 71
tccctgagga cagcctacat agag                                           24

<210> SEQ ID NO 72
<211> LENGTH: 24
<212> TYPE: DNA
<213> ORGANISM: Artificial Sequence
<220> FEATURE:
<223> OTHER INFORMATION: Primer 3VH2-7
```

```
<400> SEQUENCE: 72
ctcaccatct ccaaggacac ctcc                                         24

<210> SEQ ID NO 73
<211> LENGTH: 24
<212> TYPE: DNA
<213> ORGANISM: Artificial Sequence
<220> FEATURE:
<223> OTHER INFORMATION: Primer 3VH2-8

<400> SEQUENCE: 73
ctcaccatca ccaaggacac ctcc                                         24

<210> SEQ ID NO 74
<211> LENGTH: 24
<212> TYPE: DNA
<213> ORGANISM: Artificial Sequence
<220> FEATURE:
<223> OTHER INFORMATION: Primer 3VH2-9

<400> SEQUENCE: 74
ctcattatct ccaaggacac ctcc                                         24

<210> SEQ ID NO 75
<211> LENGTH: 24
<212> TYPE: DNA
<213> ORGANISM: Artificial Sequence
<220> FEATURE:
<223> OTHER INFORMATION: Primer 3VH2-10

<400> SEQUENCE: 75
ctcaccatta ccaaggacac ctcc                                         24

<210> SEQ ID NO 76
<211> LENGTH: 26
<212> TYPE: DNA
<213> ORGANISM: Artificial Sequence
<220> FEATURE:
<223> OTHER INFORMATION: Primer 3VH3-26

<400> SEQUENCE: 76
cgctgtatct gcaaatgaac agcctg                                       26

<210> SEQ ID NO 77
<211> LENGTH: 28
<212> TYPE: DNA
<213> ORGANISM: Artificial Sequence
<220> FEATURE:
<223> OTHER INFORMATION: Primer 3VH3-27

<400> SEQUENCE: 77
ctcactgtat ctgcaaatga acagcctg                                     28

<210> SEQ ID NO 78
<211> LENGTH: 24
<212> TYPE: DNA
<213> ORGANISM: Artificial Sequence
<220> FEATURE:
<223> OTHER INFORMATION: Primer 3VH3-28

<400> SEQUENCE: 78
ctgtatcagc aaatgaacag cctg                                         24

<210> SEQ ID NO 79
<211> LENGTH: 26
```

```
<212> TYPE: DNA
<213> ORGANISM: Artificial Sequence
<220> FEATURE:
<223> OTHER INFORMATION: Primer 3VH3-30

<400> SEQUENCE: 79
cgctgcatct tcaaatgaac agcctg                                              26

<210> SEQ ID NO 80
<211> LENGTH: 28
<212> TYPE: DNA
<213> ORGANISM: Artificial Sequence
<220> FEATURE:
<223> OTHER INFORMATION: Primer 3VH3-31

<400> SEQUENCE: 80
cacgctgtat cttcaaatga acagcctg                                            28

<210> SEQ ID NO 81
<211> LENGTH: 25
<212> TYPE: DNA
<213> ORGANISM: Artificial Sequence
<220> FEATURE:
<223> OTHER INFORMATION: Primer 3VH3-32

<400> SEQUENCE: 81
cctctatctg caagtgaaca gcctg                                               25

<210> SEQ ID NO 82
<211> LENGTH: 25
<212> TYPE: DNA
<213> ORGANISM: Artificial Sequence
<220> FEATURE:
<223> OTHER INFORMATION: Primer 3VH3-33

<400> SEQUENCE: 82
gctgtatctg caaatgagca gcctg                                               25

<210> SEQ ID NO 83
<211> LENGTH: 26
<212> TYPE: DNA
<213> ORGANISM: Artificial Sequence
<220> FEATURE:
<223> OTHER INFORMATION: Primer 3VH3-34

<400> SEQUENCE: 83
cgctgtatct gcaaatgatc agcctg                                              26

<210> SEQ ID NO 84
<211> LENGTH: 28
<212> TYPE: DNA
<213> ORGANISM: Artificial Sequence
<220> FEATURE:
<223> OTHER INFORMATION: Primer 3VH3-35

<400> SEQUENCE: 84
catcacctat ctgcaaatga agagcctg                                            28

<210> SEQ ID NO 85
<211> LENGTH: 27
<212> TYPE: DNA
<213> ORGANISM: Artificial Sequence
<220> FEATURE:
<223> OTHER INFORMATION: Primer 3VH3-36

<400> SEQUENCE: 85
```

```
accctgtatc tgcaaacgaa tagcctg                                          27

<210> SEQ ID NO 86
<211> LENGTH: 25
<212> TYPE: DNA
<213> ORGANISM: Artificial Sequence
<220> FEATURE:
<223> OTHER INFORMATION: Primer 3VH3-37

<400> SEQUENCE: 86
gctgtatctt caaatgggca gcctg                                            25

<210> SEQ ID NO 87
<211> LENGTH: 34
<212> TYPE: DNA
<213> ORGANISM: Artificial Sequence
<220> FEATURE:
<223> OTHER INFORMATION: Primer 3VH3-38

<400> SEQUENCE: 87
caagaactca ctgtatttgc aaatgaacag tctg                                  34

<210> SEQ ID NO 88
<211> LENGTH: 35
<212> TYPE: DNA
<213> ORGANISM: Artificial Sequence
<220> FEATURE:
<223> OTHER INFORMATION: Primer 3VH3-39

<400> SEQUENCE: 88
ccaagaactc actgtatttg ctaatgaaca gtctg                                 35

<210> SEQ ID NO 89
<211> LENGTH: 26
<212> TYPE: DNA
<213> ORGANISM: Artificial Sequence
<220> FEATURE:
<223> OTHER INFORMATION: Primer 3VH3-40

<400> SEQUENCE: 89
caccgtatct ccaaacgaac agtctg                                           26

<210> SEQ ID NO 90
<211> LENGTH: 28
<212> TYPE: DNA
<213> ORGANISM: Artificial Sequence
<220> FEATURE:
<223> OTHER INFORMATION: Primer 3VH3-41

<400> SEQUENCE: 90
cacgctgtat gttcaaatga gcagtctg                                         28

<210> SEQ ID NO 91
<211> LENGTH: 26
<212> TYPE: DNA
<213> ORGANISM: Artificial Sequence
<220> FEATURE:
<223> OTHER INFORMATION: Primer 3VH3-42

<400> SEQUENCE: 91
ccctgtatct gcaaaagaac agacgg                                           26

<210> SEQ ID NO 92
<211> LENGTH: 34
<212> TYPE: DNA
<213> ORGANISM: Artificial Sequence
```

```
<220> FEATURE:
<223> OTHER INFORMATION: Primer 3VH3-43

<400> SEQUENCE: 92
taagaactct ctgtatctgc aaatgaacag tcag                              34

<210> SEQ ID NO 93
<211> LENGTH: 34
<212> TYPE: DNA
<213> ORGANISM: Artificial Sequence
<220> FEATURE:
<223> OTHER INFORMATION: Primer 3VH3-44

<400> SEQUENCE: 93
taagaactct ctgtatctgc aaatgaacac tcag                              34

<210> SEQ ID NO 94
<211> LENGTH: 31
<212> TYPE: DNA
<213> ORGANISM: Artificial Sequence
<220> FEATURE:
<223> OTHER INFORMATION: Primer 3VH3-45

<400> SEQUENCE: 94
gaacacgctg tatcttcaaa tgaacaacct g                                 31

<210> SEQ ID NO 95
<211> LENGTH: 24
<212> TYPE: DNA
<213> ORGANISM: Artificial Sequence
<220> FEATURE:
<223> OTHER INFORMATION: Primer 3VH4-17

<400> SEQUENCE: 95
acctactaca acccgtccct caag                                         24

<210> SEQ ID NO 96
<211> LENGTH: 24
<212> TYPE: DNA
<213> ORGANISM: Artificial Sequence
<220> FEATURE:
<223> OTHER INFORMATION: Primer 3VH4-19

<400> SEQUENCE: 96
accaactaca acccctccct caag                                         24

<210> SEQ ID NO 97
<211> LENGTH: 24
<212> TYPE: DNA
<213> ORGANISM: Artificial Sequence
<220> FEATURE:
<223> OTHER INFORMATION: Primer 3VH4-21

<400> SEQUENCE: 97
accaacaaca acccgtccct caag                                         24

<210> SEQ ID NO 98
<211> LENGTH: 24
<212> TYPE: DNA
<213> ORGANISM: Artificial Sequence
<220> FEATURE:
<223> OTHER INFORMATION: Primer 3VH4-24

<400> SEQUENCE: 98
cccaactaca acccatccct caag                                         24
```

<210> SEQ ID NO 99
<211> LENGTH: 20
<212> TYPE: DNA
<213> ORGANISM: Artificial Sequence
<220> FEATURE:
<223> OTHER INFORMATION: Primer 3VH5-1

<400> SEQUENCE: 99
gcagtggagc agcctgaagg                                                    20

<210> SEQ ID NO 100
<211> LENGTH: 27
<212> TYPE: DNA
<213> ORGANISM: Artificial Sequence
<220> FEATURE:
<223> OTHER INFORMATION: Primer 3VH6-5

<400> SEQUENCE: 100
cagacacatc caagaaccag ttctccc                                            27

<210> SEQ ID NO 101
<211> LENGTH: 26
<212> TYPE: DNA
<213> ORGANISM: Artificial Sequence
<220> FEATURE:
<223> OTHER INFORMATION: Primer 3VH7-8

<400> SEQUENCE: 101
gtttgtcttc tccttggaca cctctg                                             26

<210> SEQ ID NO 102
<211> LENGTH: 26
<212> TYPE: DNA
<213> ORGANISM: Artificial Sequence
<220> FEATURE:
<223> OTHER INFORMATION: Primer 3VH7-9

<400> SEQUENCE: 102
gtttgtcttc tccatggaca cgtctg                                             26

<210> SEQ ID NO 103
<211> LENGTH: 26
<212> TYPE: DNA
<213> ORGANISM: Artificial Sequence
<220> FEATURE:
<223> OTHER INFORMATION: Primer 3VH7-10

<400> SEQUENCE: 103
gtttgtcttc tccttggaca cgtctg                                             26

<210> SEQ ID NO 104
<211> LENGTH: 19
<212> TYPE: DNA
<213> ORGANISM: Artificial Sequence
<220> FEATURE:
<223> OTHER INFORMATION: Primer JH2

<400> SEQUENCE: 104
acctgaggag acggtgacc                                                     19

<210> SEQ ID NO 105
<211> LENGTH: 22
<212> TYPE: DNA
<213> ORGANISM: Artificial Sequence
<220> FEATURE:
<223> OTHER INFORMATION: Primer JH3

```
<400> SEQUENCE: 105
cctgaagaga cggtgaccat tg                                                22

<210> SEQ ID NO 106
<211> LENGTH: 21
<212> TYPE: DNA
<213> ORGANISM: Artificial Sequence
<220> FEATURE:
<223> OTHER INFORMATION: Primer JH4

<400> SEQUENCE: 106
acctgaggag acagtgacca g                                                 21

<210> SEQ ID NO 107
<211> LENGTH: 21
<212> TYPE: DNA
<213> ORGANISM: Artificial Sequence
<220> FEATURE:
<223> OTHER INFORMATION: Primer VK1-1

<400> SEQUENCE: 107
cccatcaagg ttcagcggca g                                                 21

<210> SEQ ID NO 108
<211> LENGTH: 21
<212> TYPE: DNA
<213> ORGANISM: Artificial Sequence
<220> FEATURE:
<223> OTHER INFORMATION: Primer VK1-2

<400> SEQUENCE: 108
cccatcaaag ttcagcggca g                                                 21

<210> SEQ ID NO 109
<211> LENGTH: 24
<212> TYPE: DNA
<213> ORGANISM: Artificial Sequence
<220> FEATURE:
<223> OTHER INFORMATION: Primer VK1-3

<400> SEQUENCE: 109
ggtcccatca aggttcagtg gaag                                              24

<210> SEQ ID NO 110
<211> LENGTH: 21
<212> TYPE: DNA
<213> ORGANISM: Artificial Sequence
<220> FEATURE:
<223> OTHER INFORMATION: Primer VK1-4

<400> SEQUENCE: 110
cccatctcgg ttcagtggca g                                                 21

<210> SEQ ID NO 111
<211> LENGTH: 23
<212> TYPE: DNA
<213> ORGANISM: Artificial Sequence
<220> FEATURE:
<223> OTHER INFORMATION: Primer VK1-5

<400> SEQUENCE: 111
gtcccatcaa ggttcagtgg cag                                               23

<210> SEQ ID NO 112
```

```
<211> LENGTH: 21
<212> TYPE: DNA
<213> ORGANISM: Artificial Sequence
<220> FEATURE:
<223> OTHER INFORMATION: Primer VK1-6

<400> SEQUENCE: 112
cccatccagg ttcagtggca g                                        21

<210> SEQ ID NO 113
<211> LENGTH: 24
<212> TYPE: DNA
<213> ORGANISM: Artificial Sequence
<220> FEATURE:
<223> OTHER INFORMATION: Primer VK1-7

<400> SEQUENCE: 113
gattccctct cggttcagtg acag                                     24

<210> SEQ ID NO 114
<211> LENGTH: 20
<212> TYPE: DNA
<213> ORGANISM: Artificial Sequence
<220> FEATURE:
<223> OTHER INFORMATION: Primer VK1-8

<400> SEQUENCE: 114
ccctctcagt tcagtgacag                                          20

<210> SEQ ID NO 115
<211> LENGTH: 20
<212> TYPE: DNA
<213> ORGANISM: Artificial Sequence
<220> FEATURE:
<223> OTHER INFORMATION: Primer VK1-9

<400> SEQUENCE: 115
cccactcggt tcagtgacag                                          20

<210> SEQ ID NO 116
<211> LENGTH: 21
<212> TYPE: DNA
<213> ORGANISM: Artificial Sequence
<220> FEATURE:
<223> OTHER INFORMATION: Primer VK1-10

<400> SEQUENCE: 116
ctcatcgagg ttcagtggca g                                        21

<210> SEQ ID NO 117
<211> LENGTH: 17
<212> TYPE: DNA
<213> ORGANISM: Artificial Sequence
<220> FEATURE:
<223> OTHER INFORMATION: Primer VK2-1

<400> SEQUENCE: 117
agtggcagcg ggtcagg                                             17

<210> SEQ ID NO 118
<211> LENGTH: 20
<212> TYPE: DNA
<213> ORGANISM: Artificial Sequence
<220> FEATURE:
<223> OTHER INFORMATION: Primer VK2-2

<400> SEQUENCE: 118
```
ttcagtggca gtgggtcagg                                              20

<210> SEQ ID NO 119
<211> LENGTH: 22
<212> TYPE: DNA
<213> ORGANISM: Artificial Sequence
<220> FEATURE:
<223> OTHER INFORMATION: Primer VK2-3

<400> SEQUENCE: 119
ggtttagtgg cagtgggtca gg                                           22

<210> SEQ ID NO 120
<211> LENGTH: 17
<212> TYPE: DNA
<213> ORGANISM: Artificial Sequence
<220> FEATURE:
<223> OTHER INFORMATION: Primer VK2-4

<400> SEQUENCE: 120
agcggcagtg ggtcagg                                                 17

<210> SEQ ID NO 121
<211> LENGTH: 21
<212> TYPE: DNA
<213> ORGANISM: Artificial Sequence
<220> FEATURE:
<223> OTHER INFORMATION: Primer VK2-5

<400> SEQUENCE: 121
ttcagtggca gtggatcagg c                                            21

<210> SEQ ID NO 122
<211> LENGTH: 17
<212> TYPE: DNA
<213> ORGANISM: Artificial Sequence
<220> FEATURE:
<223> OTHER INFORMATION: Primer VK2-6

<400> SEQUENCE: 122
agtggcagtg gggcagg                                                 17

<210> SEQ ID NO 123
<211> LENGTH: 17
<212> TYPE: DNA
<213> ORGANISM: Artificial Sequence
<220> FEATURE:
<223> OTHER INFORMATION: Primer VK2-7

<400> SEQUENCE: 123
agtggcagtg ggtcggg                                                 17

<210> SEQ ID NO 124
<211> LENGTH: 20
<212> TYPE: DNA
<213> ORGANISM: Artificial Sequence
<220> FEATURE:
<223> OTHER INFORMATION: Primer VK2-8

<400> SEQUENCE: 124
ttcagtggca gcaggtcagg                                              20

<210> SEQ ID NO 125
<211> LENGTH: 20
<212> TYPE: DNA

<213> ORGANISM: Artificial Sequence
<220> FEATURE:
<223> OTHER INFORMATION: Primer VK3-1

<400> SEQUENCE: 125
ccaggttcag tggcagtggg                                         20

<210> SEQ ID NO 126
<211> LENGTH: 21
<212> TYPE: DNA
<213> ORGANISM: Artificial Sequence
<220> FEATURE:
<223> OTHER INFORMATION: Primer VK3-2

<400> SEQUENCE: 126
gacaggttca gtggcagtgg g                                       21

<210> SEQ ID NO 127
<211> LENGTH: 21
<212> TYPE: DNA
<213> ORGANISM: Artificial Sequence
<220> FEATURE:
<223> OTHER INFORMATION: Primer VK3-3

<400> SEQUENCE: 127
gcaaggttca gtggcagtgg g                                       21

<210> SEQ ID NO 128
<211> LENGTH: 21
<212> TYPE: DNA
<213> ORGANISM: Artificial Sequence
<220> FEATURE:
<223> OTHER INFORMATION: Primer VK3-4

<400> SEQUENCE: 128
gccaggttca gtggtagtgg g                                       21

<210> SEQ ID NO 129
<211> LENGTH: 21
<212> TYPE: DNA
<213> ORGANISM: Artificial Sequence
<220> FEATURE:
<223> OTHER INFORMATION: Primer VK4-1

<400> SEQUENCE: 129
gtccctgacc gattcagtgg c                                       21

<210> SEQ ID NO 130
<211> LENGTH: 20
<212> TYPE: DNA
<213> ORGANISM: Artificial Sequence
<220> FEATURE:
<223> OTHER INFORMATION: Primer VK5-1

<400> SEQUENCE: 130
ttcagtggca gcgggtatgg                                         20

<210> SEQ ID NO 131
<211> LENGTH: 22
<212> TYPE: DNA
<213> ORGANISM: Artificial Sequence
<220> FEATURE:
<223> OTHER INFORMATION: Primer VK6-1

<400> SEQUENCE: 131
gttcagtggc agtggatctg gg                                      22

<210> SEQ ID NO 132
<211> LENGTH: 18
<212> TYPE: DNA
<213> ORGANISM: Artificial Sequence
<220> FEATURE:
<223> OTHER INFORMATION: Primer VK7-1

<400> SEQUENCE: 132
aggttcagcg gcagtggg                                                 18

<210> SEQ ID NO 133
<211> LENGTH: 22
<212> TYPE: DNA
<213> ORGANISM: Artificial Sequence
<220> FEATURE:
<223> OTHER INFORMATION: Primer JK-1

<400> SEQUENCE: 133
atttccacct tggtcccttg gc                                            22

<210> SEQ ID NO 134
<211> LENGTH: 20
<212> TYPE: DNA
<213> ORGANISM: Artificial Sequence
<220> FEATURE:
<223> OTHER INFORMATION: Primer JK-2

<400> SEQUENCE: 134
atctccagct tggtcccctg                                               20

<210> SEQ ID NO 135
<211> LENGTH: 22
<212> TYPE: DNA
<213> ORGANISM: Artificial Sequence
<220> FEATURE:
<223> OTHER INFORMATION: Primer JK-3

<400> SEQUENCE: 135
atatccactt tggtcccagg gc                                            22

<210> SEQ ID NO 136
<211> LENGTH: 19
<212> TYPE: DNA
<213> ORGANISM: Artificial Sequence
<220> FEATURE:
<223> OTHER INFORMATION: Primer JK-4

<400> SEQUENCE: 136
ctccaccttg gtccctccg                                                19

<210> SEQ ID NO 137
<211> LENGTH: 22
<212> TYPE: DNA
<213> ORGANISM: Artificial Sequence
<220> FEATURE:
<223> OTHER INFORMATION: Primer JK-5

<400> SEQUENCE: 137
atctccagtc gtgtcccttg gc                                            22

<210> SEQ ID NO 138
<211> LENGTH: 32
<212> TYPE: DNA
<213> ORGANISM: Artificial Sequence
<220> FEATURE:

<223> OTHER INFORMATION: Forward primer for IDH1

<400> SEQUENCE: 138
aagaataaaa cacatacaag ttggaaattt ct                                    32

<210> SEQ ID NO 139
<211> LENGTH: 28
<212> TYPE: DNA
<213> ORGANISM: Artificial Sequence
<220> FEATURE:
<223> OTHER INFORMATION: Reverse primer for IDH1

<400> SEQUENCE: 139
gagaagccat tatctgcaaa aatatccc                                         28

<210> SEQ ID NO 140
<211> LENGTH: 23
<212> TYPE: DNA
<213> ORGANISM: Artificial Sequence
<220> FEATURE:
<223> OTHER INFORMATION: Forward primer for IDH2

<400> SEQUENCE: 140
acaaagtctg tggccttgta ctg                                              23

<210> SEQ ID NO 141
<211> LENGTH: 21
<212> TYPE: DNA
<213> ORGANISM: Artificial Sequence
<220> FEATURE:
<223> OTHER INFORMATION: Reverse primer for IDH2

<400> SEQUENCE: 141
ctggaccaag cccatcacca t                                                21

<210> SEQ ID NO 142
<211> LENGTH: 32
<212> TYPE: DNA
<213> ORGANISM: Artificial Sequence
<220> FEATURE:
<223> OTHER INFORMATION: Forward primer for NPM1

<400> SEQUENCE: 142
gttaactctc tggtggtaga atgaaaaata ga                                    32

<210> SEQ ID NO 143
<211> LENGTH: 32
<212> TYPE: DNA
<213> ORGANISM: Artificial Sequence
<220> FEATURE:
<223> OTHER INFORMATION: Reverse primer for NPM1

<400> SEQUENCE: 143
gatatcaact gttacagaaa tgaaataaga cg                                    32

<210> SEQ ID NO 144
<211> LENGTH: 30
<212> TYPE: DNA
<213> ORGANISM: Artificial Sequence
<220> FEATURE:
<223> OTHER INFORMATION: Forward primer for FLT3

<400> SEQUENCE: 144
ttggaaactc ccatttgaga tcatattcat                                       30

```
<210> SEQ ID NO 145
<211> LENGTH: 27
<212> TYPE: DNA
<213> ORGANISM: Artificial Sequence
<220> FEATURE:
<223> OTHER INFORMATION: Reverse primer for FLT3

<400> SEQUENCE: 145
tctatctgca gaactgccta ttcctaa                                          27

<210> SEQ ID NO 146
<211> LENGTH: 19
<212> TYPE: DNA
<213> ORGANISM: Artificial Sequence
<220> FEATURE:
<223> OTHER INFORMATION: Forward primer for DNMT3A

<400> SEQUENCE: 146
gatgactggc acgctccat                                                   19

<210> SEQ ID NO 147
<211> LENGTH: 21
<212> TYPE: DNA
<213> ORGANISM: Artificial Sequence
<220> FEATURE:
<223> OTHER INFORMATION: Reverse primer for DNMT3A

<400> SEQUENCE: 147
gctgtgtggt tagacggctt c                                                21

<210> SEQ ID NO 148
<211> LENGTH: 24
<212> TYPE: DNA
<213> ORGANISM: Artificial Sequence
<220> FEATURE:
<223> OTHER INFORMATION: Forward primer for FLT3 a

<400> SEQUENCE: 148
gggagaaaag gcagacttta aggg                                             24

<210> SEQ ID NO 149
<211> LENGTH: 29
<212> TYPE: DNA
<213> ORGANISM: Artificial Sequence
<220> FEATURE:
<223> OTHER INFORMATION: Reverse primer for FLT3 a

<400> SEQUENCE: 149
gaagatcttc tttgctttgc atatcaagt                                        29

<210> SEQ ID NO 150
<211> LENGTH: 23
<212> TYPE: DNA
<213> ORGANISM: Artificial Sequence
<220> FEATURE:
<223> OTHER INFORMATION: Forward primer for NRAS A

<400> SEQUENCE: 150
caataacacc agcactcctc caa                                              23

<210> SEQ ID NO 151
<211> LENGTH: 26
<212> TYPE: DNA
<213> ORGANISM: Artificial Sequence
<220> FEATURE:
<223> OTHER INFORMATION: Reverse primer for NRAS A
```

```
<400> SEQUENCE: 151
gaaatacgcc agtaccgaat gaaaaa                                          26

<210> SEQ ID NO 152
<211> LENGTH: 28
<212> TYPE: DNA
<213> ORGANISM: Artificial Sequence
<220> FEATURE:
<223> OTHER INFORMATION: Forward primer for NRAS B

<400> SEQUENCE: 152
tggatcacat ctctaccaga gttaatca                                        28

<210> SEQ ID NO 153
<211> LENGTH: 23
<212> TYPE: DNA
<213> ORGANISM: Artificial Sequence
<220> FEATURE:
<223> OTHER INFORMATION: Reverse primer for NRAS B

<400> SEQUENCE: 153
gatttgccaa caaggacagt tga                                             23
```

METHOD OF TREATMENT OF DISEASE AND METHOD FOR QUANTIFYING THE LEVEL OF MINIMAL RESIDUAL DISEASE IN A SUBJECT

Cross-reference to related applications

This application is filed under the provisions of 35 U.S.C § 120 and is a continuation-in-part of U.S. patent application Ser. No. 15/848,718 filed on Dec. 20, 2017 in the name of Santiago BARRIO GARCÍA, et al. and entitled "METHOD FOR QUANTIFYING THE LEVEL OF MINIMAL RESIDUAL DISEASE IN A SUBJECT," which is a divisional of and claims benefit of U.S. patent application Ser. No. 14/932,267 filed on Nov. 4, 2015, which claims benefit of European Patent Application No. 141919670 filed on Nov. 5, 2014, which are all hereby incorporated by reference herein in their entireties.

FIELD OF THE INVENTION

The present invention may be included in the field of medicine in general, more particularly in the field of diagnosis of disease.

In particular, the present invention is focused on a method and kit and system for quantifying the level of minimal residual disease in a subject. In addition, the present invention is focused on use of the method and/or kit or system for quantifying the level of minimal residual disease in a subject and use of the method for quantifying the level of minimal residual disease in a subject in a method of treatment of said subject for a disease. Thus, the present invention is also focused on a method a treatment of a disease.

BACKGROUND TO THE INVENTION

Current methods for the detection and treatment of disease mean that it is possible to control many diseases at a clinical level, thereby obliterating all traces of the disease. Nevertheless, it may be that some diseases are not detected or that the subject's recovery is not complete after treatment. In the latter case, the disease may develop drug resistance under selective pressure of treatment by a process of clonal selection, thus allowing expansion and ultimately disease recidivism or relapse. It is therefore very important to monitor the number of diseased cells in a given tissue. In particular, it is especially beneficial to monitor the level of minimal residual disease (MRD) in subjects who have been treated for a disease. MRD is the name given to the disease that remains in a subject or a particular tissue thereof during or after treatment of said disease. Typically, MRD refers to the cancer and/or leukaemia that remains in a subject during or after treatment of said cancer and/or leukaemia by, for example, chemotherapy.

Currently monitoring through, for example, determination of MRD may be performed by different techniques. Firstly, flow cytometry (FCM) can use up to 8 different markers to determine the disease phenotype. Secondly, another method used to this end is allele specific oligonucleotide PCR (ASO-PCR) of immunoglobulin (Igs) genes, which requires the design of specific primers for each patient or a specific molecular marker and is applicable only to 40% of cases. In this regard, WO 2004033728 A2 details primers for the amplification of immunoglobulin rearrangements for the diagnosis of lymphoproliferative disorders. The amplification by PCR of rearranged immunoglobulins or genes has also been used in U.S. Pat. No. 7,785,783 B2 to characterize nucleic acid regions based on the identification of regions flanking a marker nucleic acid region. This provides means of analyzing a marker which is characteristic of a clonal population of cells and for monitoring the progression of a condition.

Finally, the emergence of next-generation sequencing (NGS) technologies has made it possible to analyze millions of sequences at once, each coming from different fragments of genome, or the result of amplification of the same region, representing a large number of cells. As a consequence, NGS technology may be used to identify disease and/or quantify a level of disease in subjects. In his regard, deep sequencing has been revealed as an alternative methodology to the aforementioned techniques which provides greater applicability than ASO-PCR and higher sensitivity than FCM [cf. Martinez-Lopez J. et al. "*Prognostic value of deep sequencing method for minimal residual disease detection in multiple myeloma*"; Blood (2014) 123(20):3073-3079]. This technique has also proved useful for detecting and quantifying myeloma cells in both the bone marrow and the peripheral blood [cf. Vij R. et al. "*Deep sequencing reveals myeloma cells in peripheral blood in majority of multiple myeloma patients*"; J. Clin. Lymphoma Myeloma Leuk. (2013) 14(2):131-139].

In addition, NGS technology has made it possible to identify clonogenic B or T cells with high sensitivity and specificity, thus allowing the detection of minimal residual disease in conditions such as acute lymphoblastic leukemias (ALL), mantle cell lymphoma (MCL) and multiple myeloma (MM) [cf. Ladetto M. et al. "*Next-generation sequencing and real-time quantitative PCR for minimal residual disease detection in B-cell disorders*"; Leukemia (2014) 28(6):1299-1307]. NGS has also proven to be a useful method for the identification of clonotypic profiles to detect and monitor a disease from a lymphocyte sample. U.S. Pat. No. 8,628,927 B2 demonstrates that the MRD of ALL can be established by comparing the sequence of a sample to previously-obtained clonotype profiles and markers on leukemic cells such as those of acute myeloid leukaemia. In addition, another approach for the detection of MRD is the determination of a clonotype profile by the use of sequence tags for producing sequence-based profiles of complex nucleic-acid populations, as disclosed in WO 2013188471 A2.

Although the aforementioned documents disclose several different approaches for detecting MRD wherein improvements in are achieved through different methods of sequencing, none of these documents specifically discloses a method which achieves improvement through the alignment strategy used. The method of alignment used is important to the accuracy of any method which is based on comparison of nucleotide sequences because the rate of failures of sequencers using a classical binary logic—in which sequences can only be equal or different—is so high that it is not useful. In fact, a high proportion (nearly all) of nucleotide sequences that evaluate as different, are equal but appear as different because of an error in the sequencer. In this regard, U.S. Pat. No. 8,628,927 B2 mentions that some sequences are harder to align than others due to somatic mutations and diverse regions [such as the NDN region between the variable (V) and joining (J) gene segments in lymphocytes]. However, despite generally disclosing that alignment may be achieved using references sequences such as primer binding sequences or non-reference sequences, this document does not disclose a specific method for alignment that is capable of determining the level of disease in a subject irrespective of the genetic characteristics of the nucleotide or the disease.

It is the problem of the present invention to provide a method for the quantification of the level of disease in a patient, wherein said method exhibits improved sensitivity, greater analytical reproducibility and more accurate determination of said levels, wherein said method can be fully automated, and thus easily standardized, thereby minimizing lab-to-lab variation. It is a further problem of the present invention to provide a universal method which is capable of determining the level of disease in a subject, irrespective of the genetic characteristics of the nucleotide or the disease, and thus allows diagnosis of the presence of disease in said subject with the capacity to develop relapse and, hence, the need for further treatment. In addition, it is a problem of the present invention to provide a method which is subject-specific and does not require access to external databases comprising data obtained from populations of subjects. Moreover, it is a problem of the invention to provide a method for the quantification of tumor clonotypic sequences for immunoglobulin gene rearrangements, as well as allelic load, point mutations (SNV), multiple mutations (MNV), indels, long insertions and translocations.

In addition, it is a problem of the present invention to provide a method for treatment of a disease which is patient-specific and ensures that the disease is treated sufficiently as to eliminate as much minimal residual disease as possible, yet also avoid unnecessarily subjecting said patient to therapy beyond that which is required to treat the disease.

BRIEF DESCRIPTION OF THE INVENTION

The present invention discloses a method for treatment of disease in a subject, wherein said disease is a cancer, comprising the steps of:

(A) administering therapy to a subject, wherein said therapy is selected from chemotherapy, immunotherapy or radiotherapy, or combinations thereof; and (B) quantifying the level of minimal residual disease (MRD) in said subject who has been treated for said disease, without the need to access an external database comprising data obtained from a population of subjects, which comprises:

(a) amplifying by polymerase chain reaction using a PCR instrument and primers, at least one nucleotide sequence comprised in an amount, D, of genomic DNA of a biological sample obtained from said subject after treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease; and sequencing said at least one nucleotide sequence on a massively parallel sequencing platform to obtain at least one first list of characters reading from left to right, wherein said sequencing is massively parallel sequencing;

(b) amplifying by polymerase chain reaction using a PCR instrument and the same locus-specific forward primer and the same locus-specific reverse primer as in step (a), at least one nucleotide sequence in a biological sample obtained from said subject prior to treatment for said disease; and sequencing said at least one nucleotide sequence on a massively parallel sequencing platform to obtain at least one second list of characters reading from left to right, wherein said sequencing is massively parallel sequencing;

(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined using at least one computer program product, either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(ii) excluding the character or longest continuous sequence of characters selected in step (i) from subsequent steps of selecting a character or longest continuous sequence of characters which is the same in the first list of characters and the second list of characters;

(iii) selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;

(iv) excluding each character and/or each longest continuous sequence of characters selected in step (iii) from subsequent steps of selecting a character or longest continuous sequence of characters which is the same in the first list of characters and the second list (v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters; and (x) calculating DS according to the following formula:

$$DS=C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up
the number of characters in the first list of characters which were excluded in any of the steps (xi) to (xv); and
the number of characters in the second list of characters which were excluded in any of the steps (xi) to (xv)
to obtain the total number of characters, $C_c$, in the first and second lists of characters which are the same as in the second and first lists of characters, respectively;

(xvii) adding up
$C_c$; and
the number of characters in the first list of characters which are located between the characters and/or longest continuous sequences of characters that were excluded from the first list of characters, and which were not excluded in any of the steps (xi) to (xv) of step (c); and
the number of characters in the second list of characters which are located between the characters and/or longest continuous sequences of characters that were excluded from the second list of characters, and which were not excluded in any of the steps (xi) to (xv) of step (c),
to obtain the total number of characters, $C_t$, in the first and second lists of characters; and (xviii) calculating DS according to the following formula:

$$DS=C_c/C_t$$

(d) selecting using at least one computer program product, for each first list of characters obtained in step (a), the DS of highest value, $DS_{HV}$;

(e) adding up using at least one computer program product, the number of first lists of characters which have a $DS_{HV}$ that is greater than a threshold value, T, to obtain the total number of first lists of characters, $L_c$, which are the same as a second list of characters;

(f) adding up, using at least one computer program product, $L_c$; and
the number of first lists of characters which do not have a $DS_{HV}$ that is greater than T,
to obtain the total number of first lists of characters, $L_t$; and (g) calculating using at least one computer program product, the level of minimal residual disease (MRD) according to any of the following formulae:

$$MRD=(L_c \times k)/(L_t \times D)$$

or $$MRD=L_c/L_t$$

or $$MRD=L_c \times (D/k)/L_t^2,$$

wherein when the level of MRD is >0 steps A and B are repeated,
wherein each repetition of step A comprises administering the same therapy as previously administered to said subject or therapy different to that previously administered to said subject.

The present invention also relates to a method for quantifying the level of minimal residual disease (MRD) in a subject who has been treated for said disease, which comprises:

(a) amplifying by polymerase chain reaction using primers, at least one nucleotide sequence comprised in an amount, D, of genomic DNA of a biological sample obtained from said subject after treatment for said disease, wherein the genomic DNA has an average weight, k, per diploid cell of said biological sample; and
  sequencing said at least one nucleotide sequence to obtain at least one first list of characters reading from left to right;
(b) amplifying by polymerase chain reaction using the same primers as in step (a), at least one nucleotide sequence in a biological sample obtained from said subject prior to treatment for said disease; and
  sequencing said at least one nucleotide sequence to obtain at least one second list of characters reading from left to right;
(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined either by:
  (i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
  (ii) excluding the character or longest continuous sequence of characters selected in step (i) from subsequent steps of selecting a character or longest continuous sequence of characters which is the same in the first list of characters and the second list of characters;
  (iii) selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
  selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;
  (iv) excluding each character and/or each longest continuous sequence of characters selected in step (iii) from subsequent steps of selecting a character or longest continuous sequence of characters which is the same in the first list of characters and the second list of characters;
  (v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and
  selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;
  (vi) excluding each character and/or each longest continuous sequences of characters selected in step (v) from subsequent steps of selecting a character or longest continuous sequence of characters which is the same in the first list of characters and the second list of characters;
  (vii) repeating steps (v) and (vi) until no character or longest continuous sequence of characters which is the same in the first list of characters and the second list of characters is selected;
  (viii) adding up
    the number of characters in the first list of characters which were excluded in any of the steps (i) to (vii); and
    the number of characters in the second list of characters which were excluded in any of the steps (i) to (vii)
  to obtain the total number of characters, $C_c$, in the first and second lists of characters which are the same as in the second and first lists of characters, respectively;
  (ix) adding up
    $C_c$; and
    the number of characters in the first list of characters which are located between the characters and/or longest continuous sequences of characters that were excluded from the first list of characters, and which were not excluded in any of the steps (i) to (vii) of step (c); and
    the number of characters in the second list of characters which are located between the characters and/or longest continuous sequences of characters that were excluded from the second list of characters, and which were not excluded in any of the to obtain the total number of characters, $C_t$, in the first and second lists of characters; and (x) calculating DS according to the following formula:

$$DS = C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up the number of characters in the first list of characters which were excluded in any of the steps (xi) to (xv); and the number of characters in the second list of characters which were excluded in any of the steps (xi) to (xv)

to obtain the total number of characters, $C_c$, in the first and second lists of characters which are the same as in the second and first lists of characters, respectively;

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters; and (xviii) calculating DS according to the following formula:

$$DS = C_c/C_t$$

(d) selecting, for each first list of characters obtained in step (a), the DS of highest value, $DS_{HV}$;

(e) adding up the number of first lists of characters which have a $DS_{HV}$ that is greater than a threshold value, T, to obtain the total number of first lists of characters, $L_c$, which are the same as a second list of characters;

(f) adding up $L_c$; and the number of first lists of characters which do not have a $DS_{HV}$ that is greater than T, to obtain the total number of first lists of characters, $L_t$; and (g) calculating the level of minimal residual disease (MRD) according to any of the following formulae:

$$MRD = (L_c \times k)/(L_t \times D)$$

or $$MRD = L_c/L_t$$

or $$MRD = L_c \times (D/k)/L_t^2.$$

In addition, the present invention discloses a kit and a system, each for quantifying the level of minimal residual disease (MRD) in a subject who has been treated for said disease, which each comprises:

(a)—means for amplifying by polymerase chain reaction using primers, at least one nucleotide sequence comprised in an amount, D, of genomic DNA of a biological sample obtained from said subject after treatment for said disease, wherein the genomic DNA has an average weight, k, per diploid cell of said biological sample; and means for sequencing said at least one nucleotide sequence to obtain at least one first list of characters reading from left to right;

(b) means for amplifying by polymerase chain reaction using the same primers as in step (a), at least one nucleotide sequence in a biological sample obtained from said subject prior to treatment for said disease; and means for sequencing said at least one nucleotide sequence to obtain at least one second list of characters reading from left to right;

(c) means for determining, for each first list of characters obtained in step (a), the degree of similarity with each second list of characters obtained in step (b), wherein a degree of similarity, DS, of a first list of characters obtained in step (a) with a second list of characters obtained in step (b) is determined either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(ii) excluding the character or longest continuous sequence of characters selected in step (i) from subsequent steps of selecting a character or longest continuous sequence of characters which is the same in the first list of characters and the second list of characters;

(iii) selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;

(iv) excluding each character and/or each longest continuous sequence of characters selected in step (iii) from subsequent steps of selecting a character or longest continuous sequence of characters which is the same in the first list of characters and the second list of characters;

(v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up
the number of characters in the first list of characters which were excluded in any of the steps (i) to (vii); and
the number of characters in the second list of characters which were excluded in any of the steps (i) to (vii) to obtain the total number of characters, $C_c$, in the first and second lists of characters which are the same as in the second and first lists of characters, respectively;

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c), to obtain the total number of characters, $C_t$, in the first and second lists of characters; and (x) calculating DS according to the following formula:

$$DS = C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;
(xv) repeating steps (xiii) and (xiv) until no character or longest continuous sequence of characters which is the same in the first list of characters and the second list of characters is selected;
(xvi) adding up
the number of characters in the first list of characters which were excluded in any of the steps (xi) to (xv); and
the number of characters in the second list of characters which were excluded in any of the steps (xi) to (xv)
to obtain the total number of characters, $C_c$, in the first and second lists of characters which are the same as in the second and first lists of characters, respectively;
(xvii) adding up
$C_c$; and
the number of characters in the first list of characters which are located between the characters and/or longest continuous sequences of characters that were excluded from the first list of characters, and which were not excluded in any of the steps (xi) to (xv) of step (c); and
the number of characters in the second list of characters which are located between the characters and/or longest continuous sequences of characters that were excluded from the second list of characters, and which were not excluded in any of the steps (xi) to (xv) of step (c),
to obtain the total number of characters, $C_t$, in the first and second lists of characters; and
(xviii) calculating DS according to the following formula:

$$DS=C_c/C_t$$

(d) means for selecting, for each first list of characters obtained in step (a), the DS of highest value, $DS_{HV}$;
(e) means for adding up the number of first lists of characters which have a $DS_{HV}$ that is greater than a threshold value, T, to obtain the total number of first lists of characters, $L_c$, which are the same as a second list of characters;
(f) means for adding up
$L_c$; and
the number of first lists of characters which do not have a $DS_{HV}$ that is greater than T,
to obtain the total number of first lists of characters, $L_t$; and
(g) means for calculating the level of minimal residual disease (MRD) according to any of the following formulae:

$$MRD=(L_c \times k)/(L_t \times D)$$

or $$MRD=L_c/L_t$$

or $$MRD=L_c \times (D/k)/L_t^2.$$

Furthermore, the present invention discloses a use of the method of treatment disclosed herein for treating a subject with said disease. Similarly, the present invention discloses a use of the method for quantifying the level of minimal residual disease disclosed herein or the kit or system disclosed herein in quantifying the level of minimal residual disease (MRD) in a subject who has been treated for said disease.

Moreover, the present invention relates to a method for quantifying the level of minimal residual disease (MRD) in a subject who has been treated for said disease, which comprises:
(a) amplifying by polymerase chain reaction using primers, at least one nucleotide sequence comprised in an amount, D, of genomic DNA of a biological sample obtained from said subject after treatment for said disease, wherein the genomic DNA has an average weight, k, per diploid cell of said biological sample; and
sequencing said at least one nucleotide sequence to obtain at least one first list of characters reading from left to right;
(b) amplifying by polymerase chain reaction using the same primers as in step (a), at least one nucleotide sequence in a biological sample obtained from said subject prior to treatment for said disease; and
sequencing said at least one nucleotide sequence to obtain at least one second list of characters reading from left to right;
(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined either by:
(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
(ii) excluding the character or longest continuous sequence of characters selected in step (i) from subsequent steps of selecting a character or longest continuous sequence of characters which is the same in the first list of characters and the second list of characters;
(iii) selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;
(iv) excluding each character and/or each longest continuous sequence of characters selected in step (iii) from subsequent steps of selecting a character or longest continuous sequence of characters which is the same in the first list of characters and the second list of characters;
(v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up the number of characters in the first list of characters which were excluded in any of the steps (i) to (vii); and the number of characters in the second list of characters which were excluded in any of the steps (i) to (vii)

to obtain the total number of characters, $C_c$, in the first and second lists of characters which are the same as in the second and first lists of characters, respectively;

(ix) adding up $C_c$; and the number of characters in the first list of characters which are located between the characters and/or longest continuous sequences of characters that were excluded from the first list of characters, and which were not excluded in any of the steps (i) to (vii) of step (c); and the number of characters in the second list of characters which are located between the characters and/or longest continuous sequences of characters that were excluded from the second list of characters, and which were not excluded in any of the steps (i) to (vii) of step (c), to obtain the total number of characters, $C_t$, in the first and second lists of characters; and (x) calculating DS according to the following formula:

$DS=C_c/C_t$ or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up the number of characters in the first list of characters which were excluded in any of the steps (xi) to (xv); and the number of characters in the second list of characters which were excluded in any of the steps (xi) to (xv)

to obtain the total number of characters, $C_c$, in the first and second lists of characters which are the same as in the second and first lists of characters, respectively;

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters; and (xviii) calculating DS according to the following formula:

$DS=C_c/C_t$ (d) amplifying by polymerase chain reaction using primers, each at least one nucleotide sequence which is the reverse complementary sequence complementary to the at least one nucleotide sequence in step (a), and sequencing said at least one reverse complementary nucleotide sequence to obtain at least one reverse complementary first list of characters reading from left to right; and amplifying by polymerase chain reaction using the same primers as in the previous step, each at least one nucleotide sequence which is the reverse complementary sequence complementary to the at least one nucleotide sequence in step (b), and sequencing said at least one reverse complementary nucleotide sequence to obtain at least one reverse complementary second list of characters reading from left to right; and determining, for each reverse complementary first list of characters obtained in step (a), the degree of similarity with each reverse complementary second list of characters obtained in step (b), wherein a degree of similarity, $DS_{rcs}$, of a reverse complementary first list of characters obtained in step (a) with a reverse complementary second list of characters obtained in step (b) is determined either by:

(xix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;

(xx) excluding the character or longest continuous sequence of characters selected in step (xix) from subsequent steps of selecting a character or longest continuous sequence of characters which is the same in the reverse complementary first list of characters and the reverse complementary second list of characters;

(xxi)—selecting the character or longest continuous sequence of characters which is located to the left of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxii) excluding each character and/or each longest continuous sequence of characters selected in step (xxi) from subsequent steps of selecting a character or longest continuous sequence of characters which is the same in the reverse complementary first list of characters and the reverse complementary second list of characters;

(xxiii)—selecting the character or longest continuous sequence of characters which is located in the continuous sequence of characters to the immediate left of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located in the continuous sequence of characters to the immediate right of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxiv) excluding each character and/or each longest continuous sequences of characters selected in step (xxiii) from subsequent steps of selecting a character or longest continuous sequence of characters which is the same in the reverse complementary first list of characters and the reverse complementary second list of characters;

(xxv) repeating steps (xxiii) and (xxiv) until no character or longest continuous sequence of characters which is the same in the reverse complementary first list of characters and the reverse complementary second list of characters is selected;

(xxvi) adding up the number of characters in the reverse complementary first list of characters which were excluded in any of the steps (xix) to (xxv); and the number of characters in the reverse complementary second list of characters which were excluded in any of the steps (xix) to (xxv)

to obtain the total number of characters, $C_c$, in the reverse complementary first and second lists of characters which are the same as in the reverse complementary second and first lists of characters, respectively;

(xxvii) adding up $C_c$; and the number of characters in the reverse complementary first list of characters which are located between the characters and/or longest continuous sequences of characters that were excluded from the reverse complementary first list of characters, and which were not excluded in any of the steps (xix) to (xxv) of step (c); and the number of characters in the reverse complementary second list of characters which are located between the characters and/or longest continuous sequences of characters that were excluded from the reverse complementary second list of characters, and which were not excluded in any of the steps (xix) to (xxv) of step (c), to obtain the total number of characters, $C_t$, in the reverse complementary first and second lists of characters; and (xxviii) calculating DS according to the following formula:

$$DS_{rcs}=C_c/C_t$$

or by:
(xxix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;
(xxx) excluding the character or longest continuous sequence of characters selected in step (xxix) from subsequent steps of selecting a character or longest continuous sequence of characters which is the same in the reverse complementary first list of characters and the reverse complementary second list of characters;
(xxxi)—selecting the character or longest continuous sequence of characters which is located to the left of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and
selecting the character or longest continuous sequence of characters which is located to the right of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;
(xxxii) excluding each character and/or each longest continuous sequence of characters selected in step (xxxi) from subsequent steps of selecting a character or longest continuous sequence of characters which is the same in the reverse complementary first list of characters and the reverse complementary second list of characters;
(xxxiii) repeating steps (xxxi) and (xxxii) until no character or longest continuous sequence of characters which is the same in the reverse complementary first list of characters and the reverse complementary second list of characters is selected;
(xxxiv) adding up
the number of characters in the reverse complementary first list of characters which were excluded in any of the steps (xxix) to (xxxiii); and
the number of characters in the reverse complementary second list of characters which were excluded in any of the steps (xxix) to (xxxiii)
to obtain the total number of characters, $C_c$, in the reverse complementary first and second lists of characters which are the same as in the reverse complementary second and first lists of characters, respectively;
(xxxv) adding up
$C_c$; and
the number of characters in the reverse complementary first list of characters which are located between the characters and/or longest continuous sequences of characters that were excluded from the reverse complementary first list of characters, and which were not excluded in any of the steps (xxix) to (xxxiii) of step (c); and
the number of characters in the reverse complementary second list of characters which are located between the characters and/or longest continuous sequences of characters that were excluded from the reverse complementary second list of characters, and which were not excluded in any of the steps (xxix) to (xxxiii) of step (c), to obtain the total number of characters, $C_t$, in the reverse complementary first and second lists of characters; and
(xxxvi) calculating DS according to the following formula:

$$DS_{rcs}=C_c/C_t$$

wherein when DS is determined for each first list of characters obtained in step (a) using sub-steps (i) to (x), $DS_{rcs}$ is determined for each corresponding reverse complementary first list of characters using sub-steps (xix) to (xxviii), and when DS is determined for each first list of characters obtained in step (a) using sub-steps (xi) to (xviii), $DS_{rcs}$ is determined for each corresponding reverse complementary first list of characters using sub-steps (xxix) to (xxxvi); and
selecting, for each first list of characters obtained in step (a) and its corresponding reverse complementary first list of characters, the DS or $DS_{rcs}$ of highest value, $DS_{HV}$;
(e) adding up the number of first lists of characters which have a $DS_{HV}$ that is greater than a threshold value, T, to obtain the total number of first lists of characters, $L_c$, which are the same as a second list of characters;
(f) adding up
$L_c$; and
the number of first lists of characters which do not have a $DS_{HV}$ that is greater than T,
to obtain the total number of first lists of characters, $L_t$; and
(g) calculating the level of minimal residual disease (MRD) according to any of the following formulae:

$$MRD=(L_c \times k)/(L_t \times D)$$

or $$MRD=L_c/L_t$$

or $$MRD=L_c \times (D/k)/L_t^2;$$

wherein in sub-steps (iii) and (xiii) of step (c), and sub-steps (xxi) and (xxxi) of step (d) of the present invention, selection is preferably repeated simultaneously for the continuous sequence of characters which is located to the left of the character or longest continuous sequence of characters excluded in sub-steps (ii) and (xii) of step (c), and sub-steps (xx) and (xxx) of step (d), respectively, and for the continuous sequence of characters which is located to the right of the character or longest continuous sequence of characters excluded in sub-steps (ii) and (xii), and sub-steps (xx) and (xxx) of step (d), respectively; and
wherein in sub-step (v) of step (c) and sub-step (xxiii) of step (d) of the present invention, selection is preferably repeated simultaneously for the continuous sequence of characters to the immediate left of each character or each longest continuous sequence of characters excluded in the previous step, and for the continuous sequence of characters to the immediate right of each character or each longest continuous sequence of characters excluded in the previous step.

Moreover, the present invention also relates to a method for treatment of disease in a subject, wherein said disease is a haematological cancer which is selected from multiple myeloma or acute myeloid leukaemia, comprising the steps of:
(A) administering therapy to a subject, wherein said therapy is chemotherapy, which consists of:
    between 9 and 18 cycles of treatment, each cycle comprising administration of bortezomib plus melphalan and prednisone (VMP) and lenalidomide plus dexamethasone (Rd), when said disease is multiple myeloma, or
    either:
        1 or 2 cycles of treatment, each cycle comprising administration of cytarabine over 7 days and subsequent administration of an anthracycline antibiotic or an anthracenedione over 3 days; or
        1 or 2 cycles of treatment, each cycle comprising administration of cytarabine over 7 days and subsequent administration of an anthracycline antibiotic or an anthracenedione over 3 days, followed by 1 or 2 cycles of treatment each comprising administration of cytarabine,
when said disease is acute myeloid leukemia; and
(B) quantifying the level of minimal residual disease (MRD) in said subject who has been treated for said disease, without the need to access an external database comprising data obtained from a population of subjects, which comprises:
(a) amplifying by polymerase chain reaction using a PCR instrument and primers, at least one nucleotide sequence comprised in an amount, D, of genomic DNA of a biological sample obtained from said subject after treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease; and
    sequencing said at least one nucleotide sequence on a massively parallel sequencing platform to obtain at least one first list of characters reading from left to right, wherein said sequencing is massively parallel sequencing;
(b) amplifying by polymerase chain reaction using a PCR instrument and the same locus-specific forward primer and the same locus-specific reverse primer as in step (a), at least one nucleotide sequence in a biological sample obtained from said subject prior to treatment for said disease; and
    sequencing said at least one nucleotide sequence on a massively parallel sequencing platform to obtain at least one second list of characters reading from left to right, wherein said sequencing is massively parallel sequencing;
(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined using at least one computer program product, either by:
    (i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
    (ii) excluding the character or longest continuous sequence of characters selected in step (i) from subsequent steps of selecting a character or longest continuous sequence of characters which is the same in the first list of characters and the second list of characters;
    (iii) selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
    selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;
    (iv) excluding each character and/or each longest continuous sequence of characters selected in step (iii) from subsequent steps of selecting a character or longest continuous sequence of characters which is the same in the first list of characters and the second list of characters;
    (v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and
    selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;
    (vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;
(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;
(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters; and
(x) calculating DS according to the following formula:

$$DS = C_c / C_t$$

or by:
(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
(xii) excluding the character or longest continuous sequence of characters selected in step (xi) from subsequent steps of selecting a character or longest continuous sequence of characters which is the same in the first list of characters and the second list of characters;
(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;
(xv) repeating steps (xiii) and (xiv) until no character or longest continuous sequence of characters which is the same in the first list of characters and the second list of characters is selected;
(xvi) adding up
the number of characters in the first list of characters which were excluded in any of the steps (xi) to (xv); and
the number of characters in the second list of characters which were excluded in any of the steps (xi) to (xv)
to obtain the total number of characters, $C_c$, in the first and second lists of characters which are the same as in the second and first lists of characters, respectively;
(xvii) adding up
$C_c$; and
the number of characters in the first list of characters which are located between the characters and/or longest continuous sequences of characters that were excluded from the first list of characters, and which were not excluded in any of the steps (xi) to (xv) of step (c); and
the number of characters in the second list of characters which are located between the characters and/or longest continuous sequences of characters that were excluded from the second list of characters, and which were not excluded in any of the steps (xi) to (xv) of step (c),
to obtain the total number of characters, $C_t$, in the first and second lists of characters; and
(xviii) calculating DS according to the following formula:

$$DS = C_c / C_t$$

(d) amplifying by polymerase chain reaction using a PCR instrument and primers, each at least one nucleotide sequence which is the reverse complementary sequence complementary to the at least one nucleotide sequence in step (a), and sequencing on a massively parallel sequencing platform said at least one reverse complementary nucleotide sequence to obtain at least one reverse complementary first list of characters reading from left to right, wherein said primers comprise a locus-specific forward primer and a locus-specific reverse primer, and said primers identify one specific variant of a nucleotide sequence present in said biological sample, wherein said one variant or the absence of said one variant is indicative of disease, and wherein said sequencing is massively parallel sequencing; and
amplifying by polymerase chain reaction using a PCR instrument and the same locus-specific forward primer and the same locus-specific reverse primer as in the previous step, each at least one nucleotide sequence which is the reverse complementary sequence complementary to the at least one nucleotide sequence in step (b), and sequencing on a massively parallel sequencing platform said at least one reverse complementary nucleotide sequence to obtain at least one reverse complementary second list of characters reading from left to right, wherein said sequencing is massively parallel sequencing; and
determining, for each reverse complementary first list of characters obtained in step (a), the degree of similarity with each reverse complementary second list of characters obtained in step (b), wherein a degree of similarity, $DS_{rcs}$, of a reverse complementary first list of characters obtained in step (a) with a reverse complementary second list of characters obtained in step (b) is determined using at least one computer program product, either by:

(xix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;

(xx) excluding the character or longest continuous sequence of characters selected in step (xix) from subsequent steps of selecting a character or longest continuous sequence of characters which is the same in the reverse complementary first list of characters and the reverse complementary second list of characters;

(xxi)—selecting the character or longest continuous sequence of characters which is located to the left of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxii) excluding each character and/or each longest continuous sequence of characters selected in step (xxi) from subsequent steps of selecting a character or longest continuous sequence of characters which is the same in the reverse complementary first list of characters and the reverse complementary second list of characters;

(xxiii)—selecting the character or longest continuous sequence of characters which is located in the continuous sequence of characters to the immediate left of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located in the continuous sequence of characters to the immediate right of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxiv) excluding each character and/or each longest continuous sequences of characters selected in step (xxiii) from subsequent steps of selecting a character or longest continuous sequence of characters which is the same in the reverse complementary first list of characters and the reverse complementary second list of characters;

(xxv) repeating steps (xxiii) and (xxiv) until no character or longest continuous sequence of characters which is the same in the reverse complementary first list of characters and the reverse complementary second list of characters is selected;

(xxvi) adding up the number of characters in the reverse complementary first list of characters which were excluded in any of the steps (xix) to (xxv); and the number of characters in the reverse complementary second list of characters which were excluded in any of the steps (xix) to (xxv)

to obtain the total number of characters, $C_c$, in the reverse complementary first and second lists of characters which are the same as in the reverse complementary second and first lists of characters, respectively;

(xxvii) adding up $C_c$; and the number of characters in the reverse complementary first list of characters which are located between the characters and/or longest continuous sequences of characters that were excluded from the reverse complementary first list of characters, and which were not excluded in any of the steps (xix) to (xxv) of step (c); and the number of characters in the reverse complementary second list of characters which are located between the characters and/or longest continuous sequences of characters that were excluded from the reverse complementary second list of characters, and which were not excluded in any of the steps (xix) to (xxv) of step (c), to obtain the total number of characters, $C_t$, in the reverse complementary first and second lists of characters; and (xxviii) calculating DS according to the following formula:

$$DS_{rcs}=C_c/C_t$$

or by:

(xxix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;

(xxx) excluding the character or longest continuous sequence of characters selected in step (xxix) from subsequent steps of selecting a character or longest continuous sequence of characters which is the same in the reverse complementary first list of characters and the reverse complementary second list of characters;
(xxxi)—selecting the character or longest continuous sequence of characters which is located to the left of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and
selecting the character or longest continuous sequence of characters which is located to the right of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;
(xxxii) excluding each character and/or each longest continuous sequence of characters selected in step (xxxi) from subsequent steps of selecting a character or longest continuous sequence of characters which is the same in the reverse complementary first list of characters and the reverse complementary second list of characters;
(xxxiii) repeating steps (xxxi) and (xxxii) until no character or longest continuous sequence of characters which is the same in the reverse complementary first list of characters and the reverse complementary second list of characters is selected;
(xxxiv) adding up
the number of characters in the reverse complementary first list of characters which were excluded in any of the steps (xxix) to (xxxiii); and
the number of characters in the reverse complementary second list of characters which were excluded in any of the steps (xxix) to (xxxiii) to obtain the total number of characters, $C_c$, in the reverse complementary first and second lists of characters which are the same as in the reverse complementary second and first lists of characters, respectively;
(xxxv) adding up
$C_c$; and
the number of characters in the reverse complementary first list of characters which are located between the characters and/or longest continuous sequences of characters that were excluded from the reverse complementary first list of characters, and which were not excluded in any of the steps (xxix) to (xxxiii) of step (c); and
the number of characters in the reverse complementary second list of characters which are located between the characters and/or longest continuous sequences of characters that were excluded from the reverse complementary second list of characters, and which were not excluded in any of the steps (xxix) to (xxxiii) of step (c),
to obtain the total number of characters, $C_t$, in the reverse complementary first and second lists of characters; and (xxxvi) calculating DS according to the following formula:

$$DS_{rcs}=C_c/C_t$$

wherein when DS is determined for each first list of characters obtained in step (a) using sub-steps (i) to (x), $DS_{rcs}$ is determined for each corresponding reverse complementary first list of characters using sub-steps (xix) to (xxviii), and when DS is determined for each first list of characters obtained in step (a) using sub-steps (xi) to (xviii), $DS_{rcs}$ is determined for each corresponding reverse complementary first list of characters using sub-steps (xxix) to (xxxvi); and
selecting, using at least one computer program product, for each first list of characters obtained in step (a) and its corresponding reverse complementary first list of characters, the DS or $DS_{rcs}$ of highest value, $DS_{HV}$;
(e) adding up using at least one computer program product, the number of first lists of characters which have a $DS_{HV}$ that is greater than a threshold value, T, to obtain the total number of first lists of characters, $L_c$, which are the same as a second list of characters;
(f) adding up, using at least one computer program product, $L_c$; and
the number of first lists of characters which do not have a $DS_{HV}$ that is greater than T,
to obtain the total number of first lists of characters, $L_t$; and
(g) calculating using at least one computer program product, the level of minimal residual disease (MRD) according to either of the following formulae:

$$MRD=(L_c \times k)/(L_t \times D)$$

or $$MRD=L_c \times (D/k)/L_t^2,$$

or $$MRD=L_c \times (D/k)/L_t^2,$$

when said disease is multiple myeloma,
or calculating using at least one computer program product, the level of minimal residual disease (MRD) according to the following formula:

$$MRD=L_c/L_t$$

when said disease is acute myeloid leukaemia,
wherein
when said disease is multiple myeloma and the level of MRD is $>10^{-6}$; or
when said disease is acute myeloid leukemia and the level of MRD is $>10^{-5}$:
steps A and B are repeated,
wherein each repetition of step A comprises administering the same chemotherapy as previously administered to said subject or chemotherapy different to that previously administered to said subject.

BRIEF DESCRIPTION OF THE FIGURES

FIG. 3. Schematic diagram representing sub-steps (xi) to (xv) of step (c) according to the invention, wherein the narrow grey line (--------) represents a first character list and the narrow black line (———) represents a second character list. Selection of a character or longest continuous sequence of characters which are the same in the first list of characters and the second list of characters is represented by broader lines (▦▦▦▦) and (■■■■), respectively, that are subsequently excluded from the aforementioned character lists.

DFS for all data sets; (panel C) OS for the induction set; (panel D) DFS for the induction set; (panel E) OS for the consolidation set; and (panel F) DFS for the induction set. Number of censored patients with respect to the stratified groups and the number at risk is indicated. *p-values are considered significant (<0.05), ** (<0.01).

Figure 17:
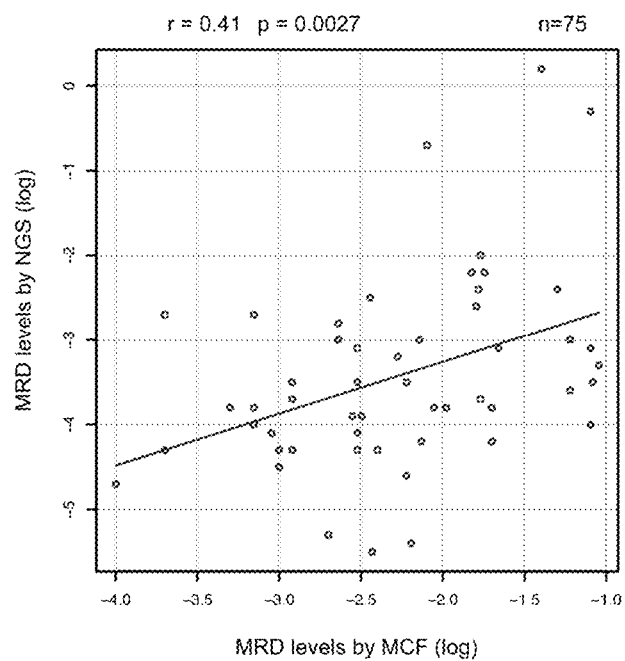
Figure 17:
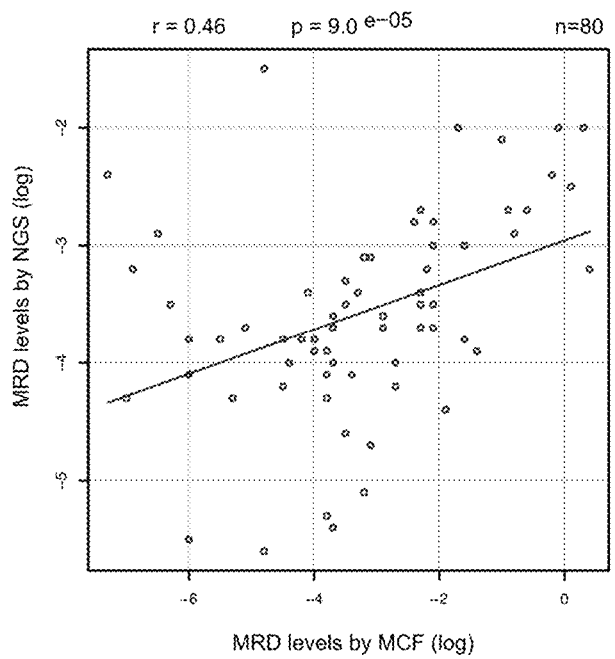

FIG. 17. Correlation of levels of MRD measured by NGS and conventional methods. Correlation between NGS vs MFC (panel A) and correlation between NGS vs q-PCR (panel B) detected by Spearman test. A significant positive correlation was found in both cases: NGS vs MFC (r=0.47, p=0.005), and NGS vs q-PCR (r=0.62, p<0.001).

Figure 18:
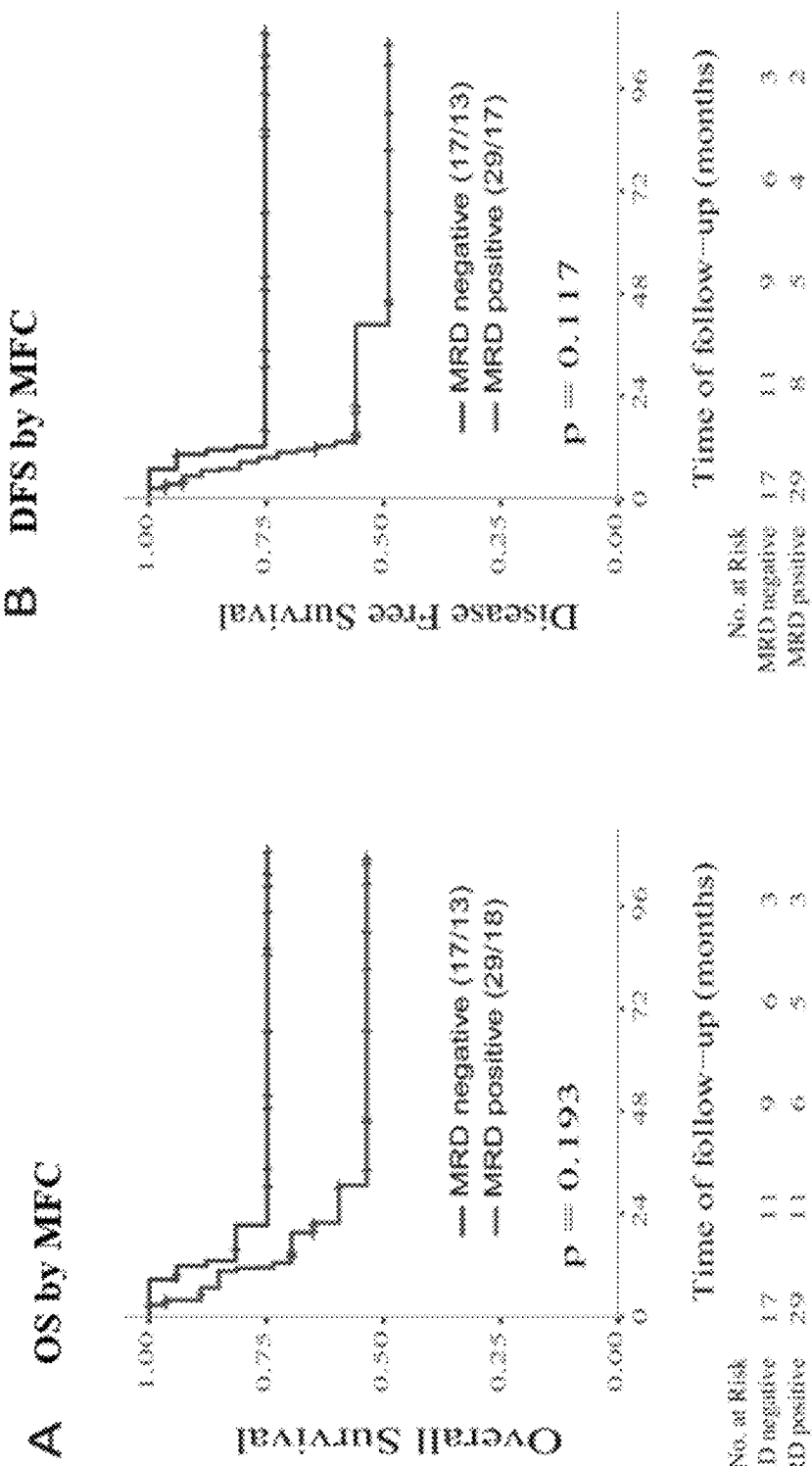
Figure 18:
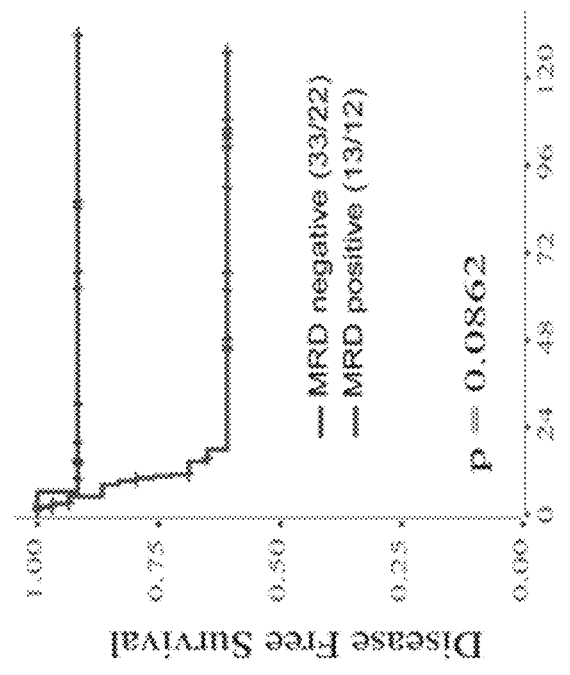
Figure 18:
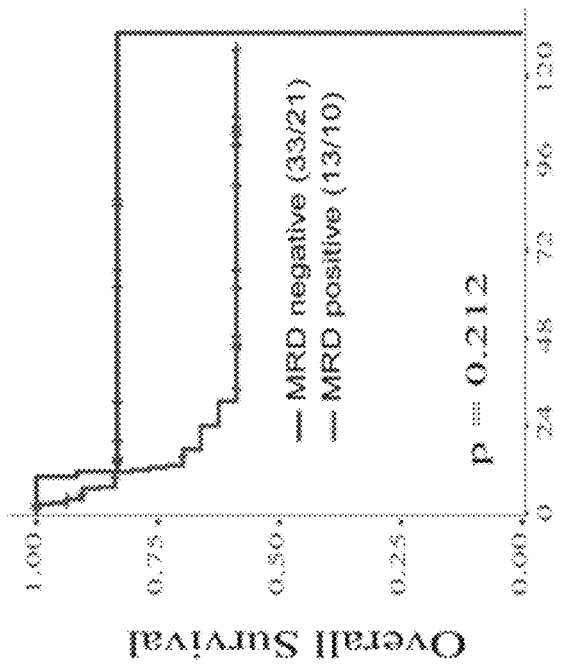

FIG. 18. Prognosis analysis of overall survival (OS, left-hand panels A and C) and disease-free survival (DFS, right-hand panels B and D) in AML patients stratified according to MRD levels by conventional methods. Kaplan-Meier plots of (panel A) OS and (panel B) DFS with respect to MFC analysis and (panel C) OS and (panel D) DFS with respect to q-PCR analysis. Number of censored patients with respect to each stratified group and number at risk is indicated. *p-values are considered significant (<0.05), ** (<0.01).

Figure 19:
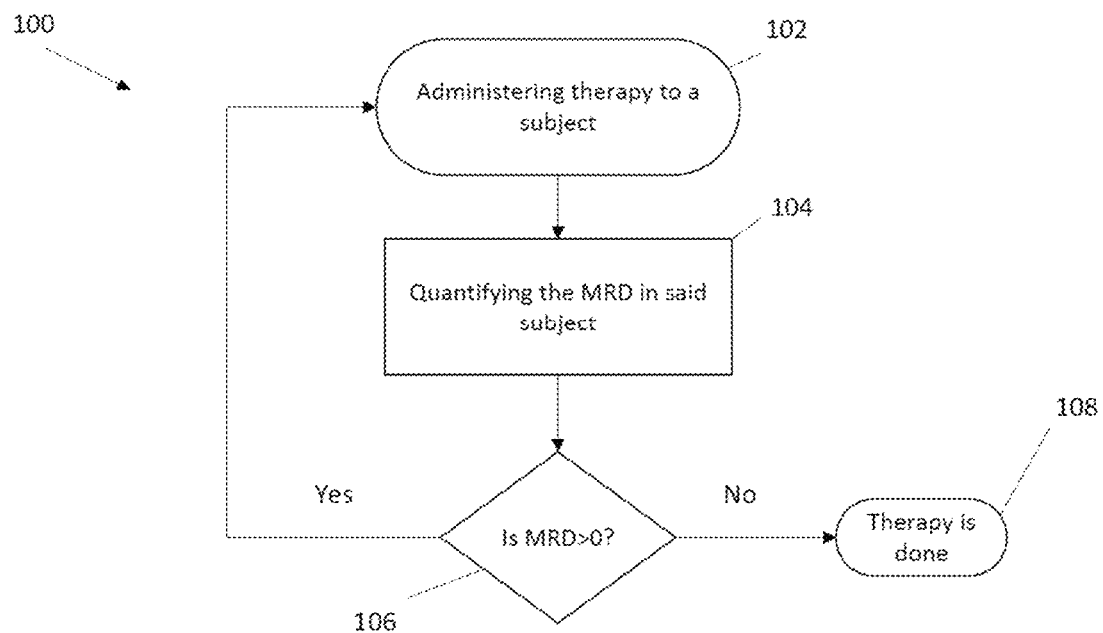

FIG. 19. Flowchart of an example of a method for treatment of disease in a subject in accordance with an embodiment of the present invention.

Figure 20:
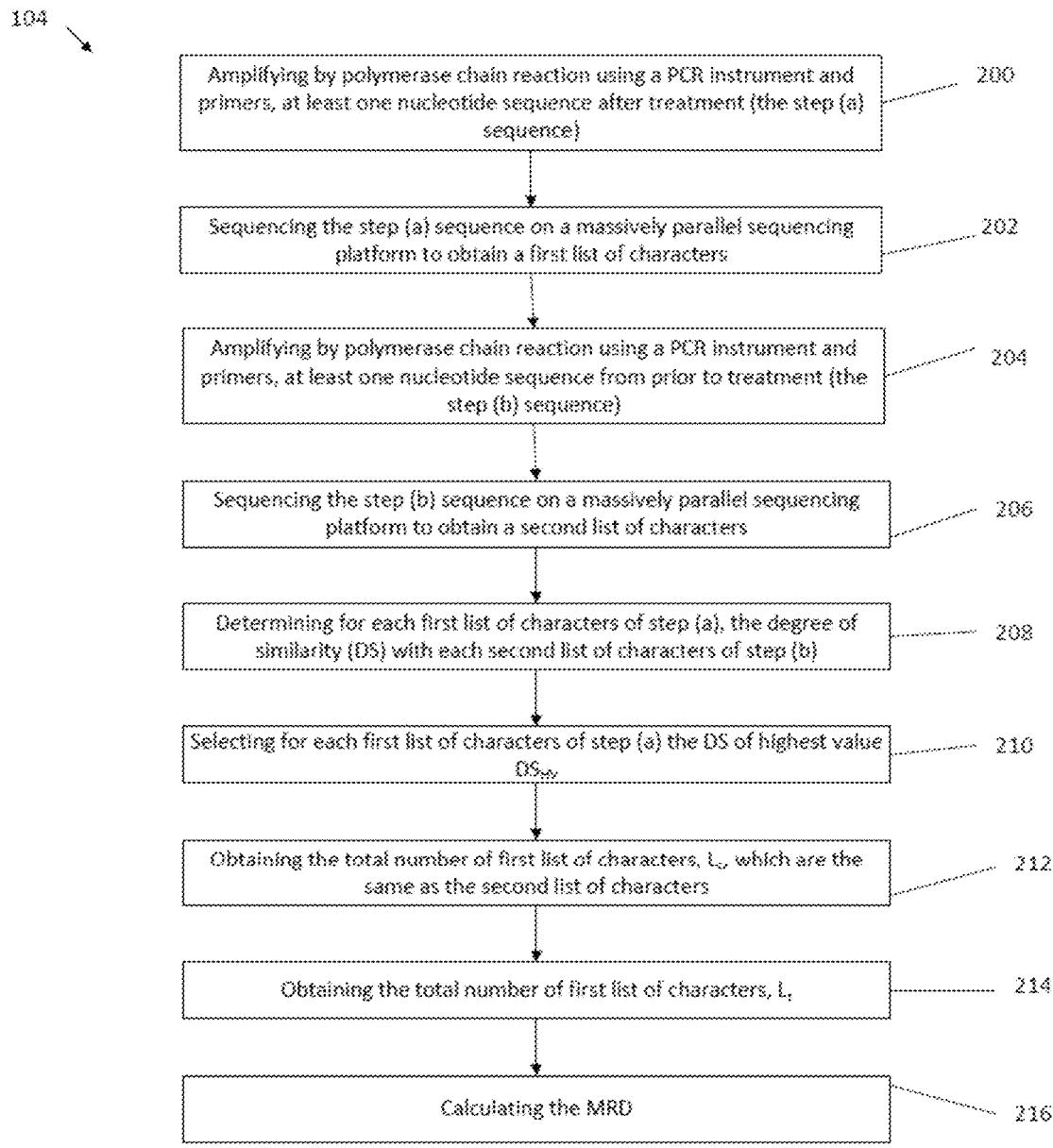

FIG. 20. Flowchart of an example of a method for quantifying the minimum residual disease (MRD) in accordance with an embodiment of the present invention.

Figure 21A:
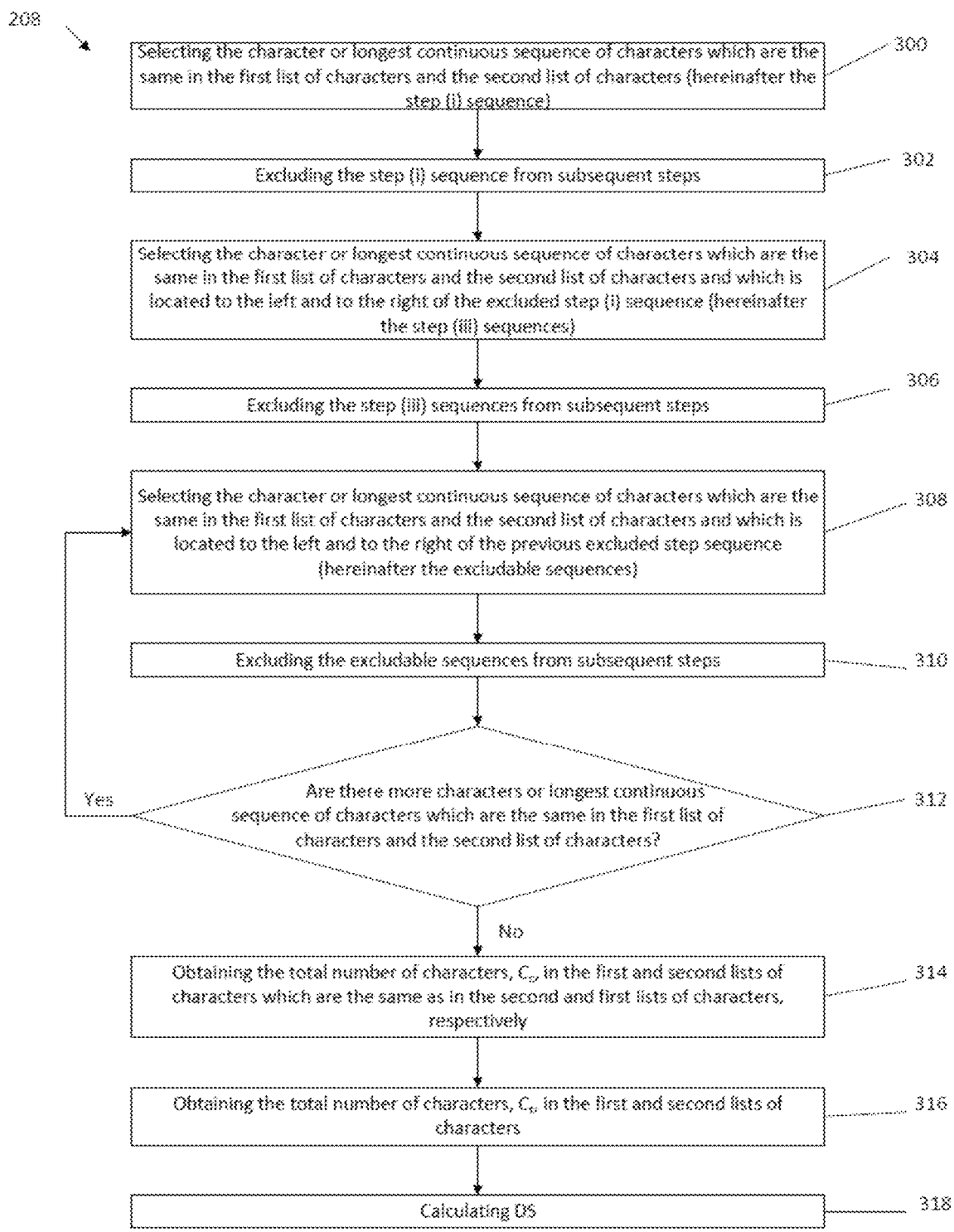

FIG. 21A. Flowchart of an example of a step for determining the degree of similarity (DS) in accordance with an embodiment of the present invention.

Figure 21B:
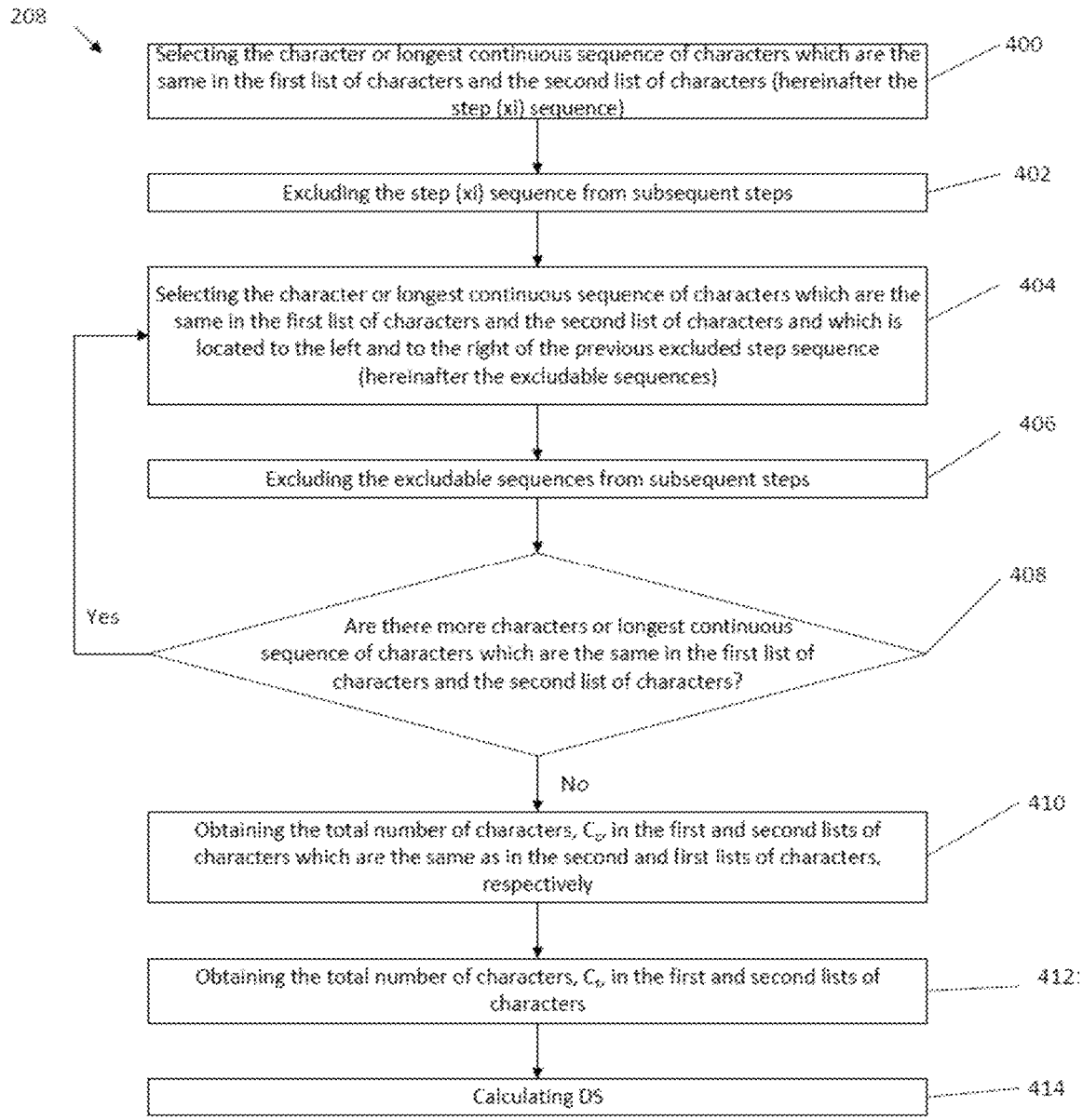

FIG. 21B. Flowchart of an example of a step for determining the degree of similarity (DS) in accordance with another embodiment of the present invention.

Figure 22:
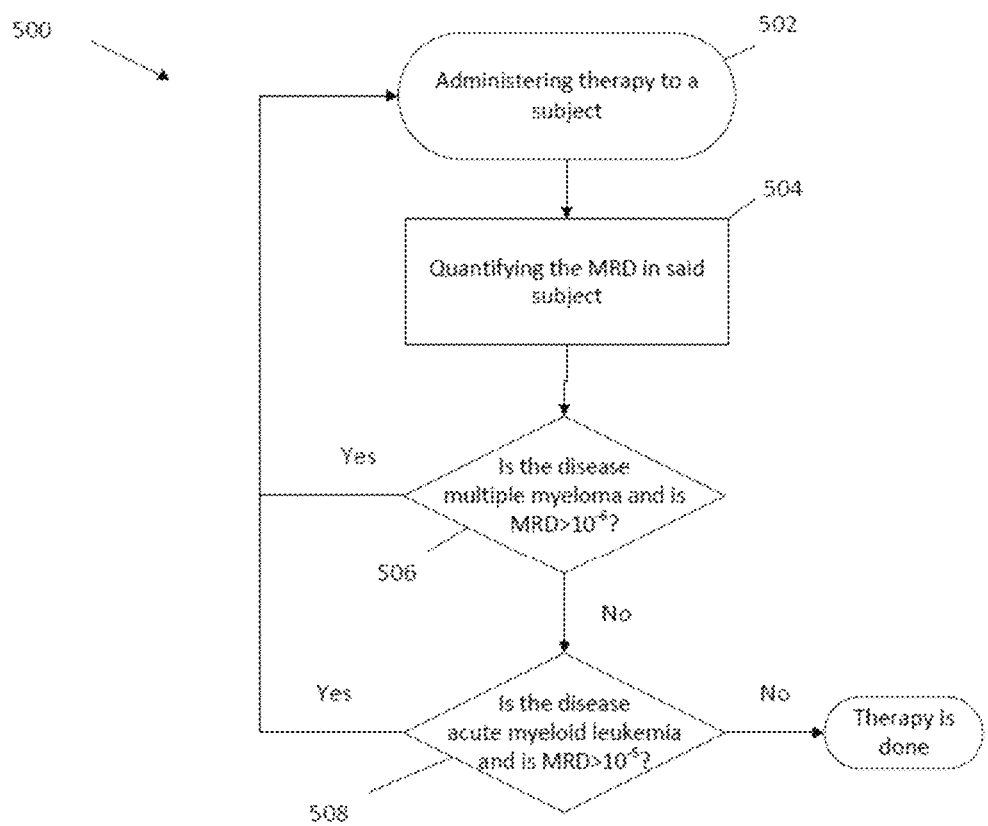

FIG. 22. Flowchart of an example of a method for treatment of disease in a subject, wherein said disease is a haematological cancer selected from multiple myeloma or acute myeloid leukaemia, in accordance with an embodiment of the present invention.

Figure 23:
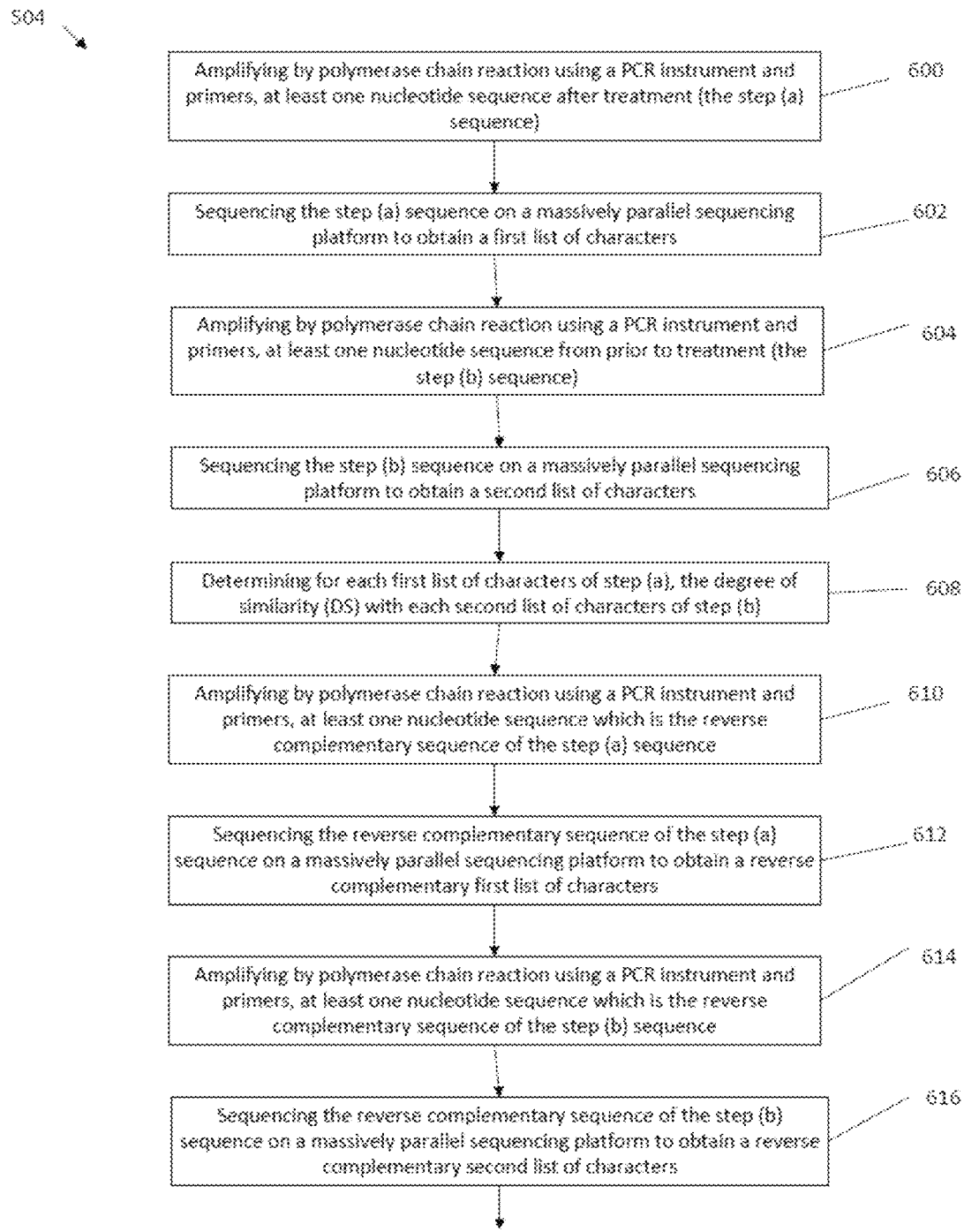
Figure 23:
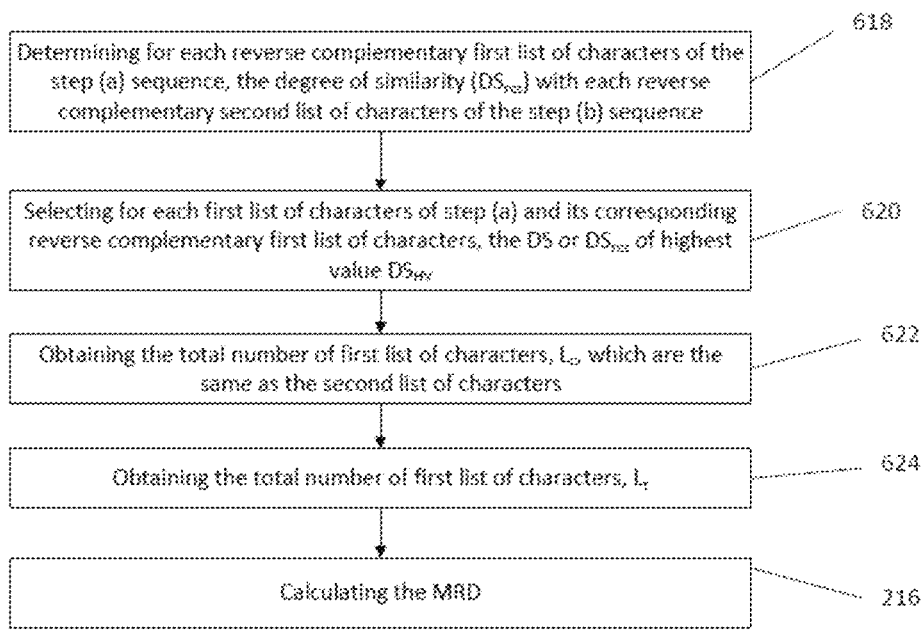

FIG. 23. Flowchart of an example of a method for quantifying the minimum residual disease (MRD) in accordance with an embodiment of the present invention.

Figure 24A:
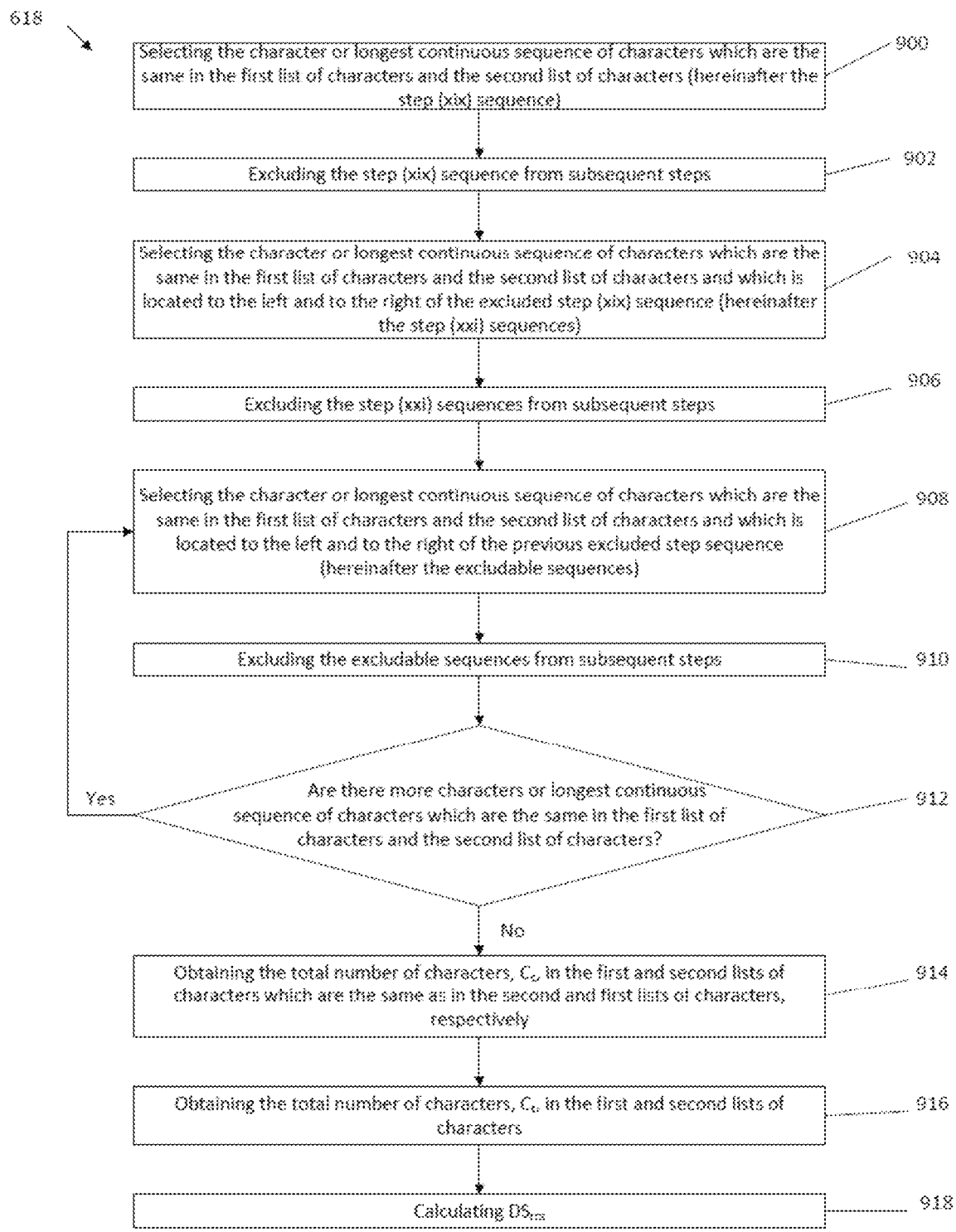

FIG. 24A. Flowchart of an example of a step for determining the reverse complementary degree of similarity ($DS_{rcs}$) in accordance with an embodiment of the present invention.

Figure 24B:
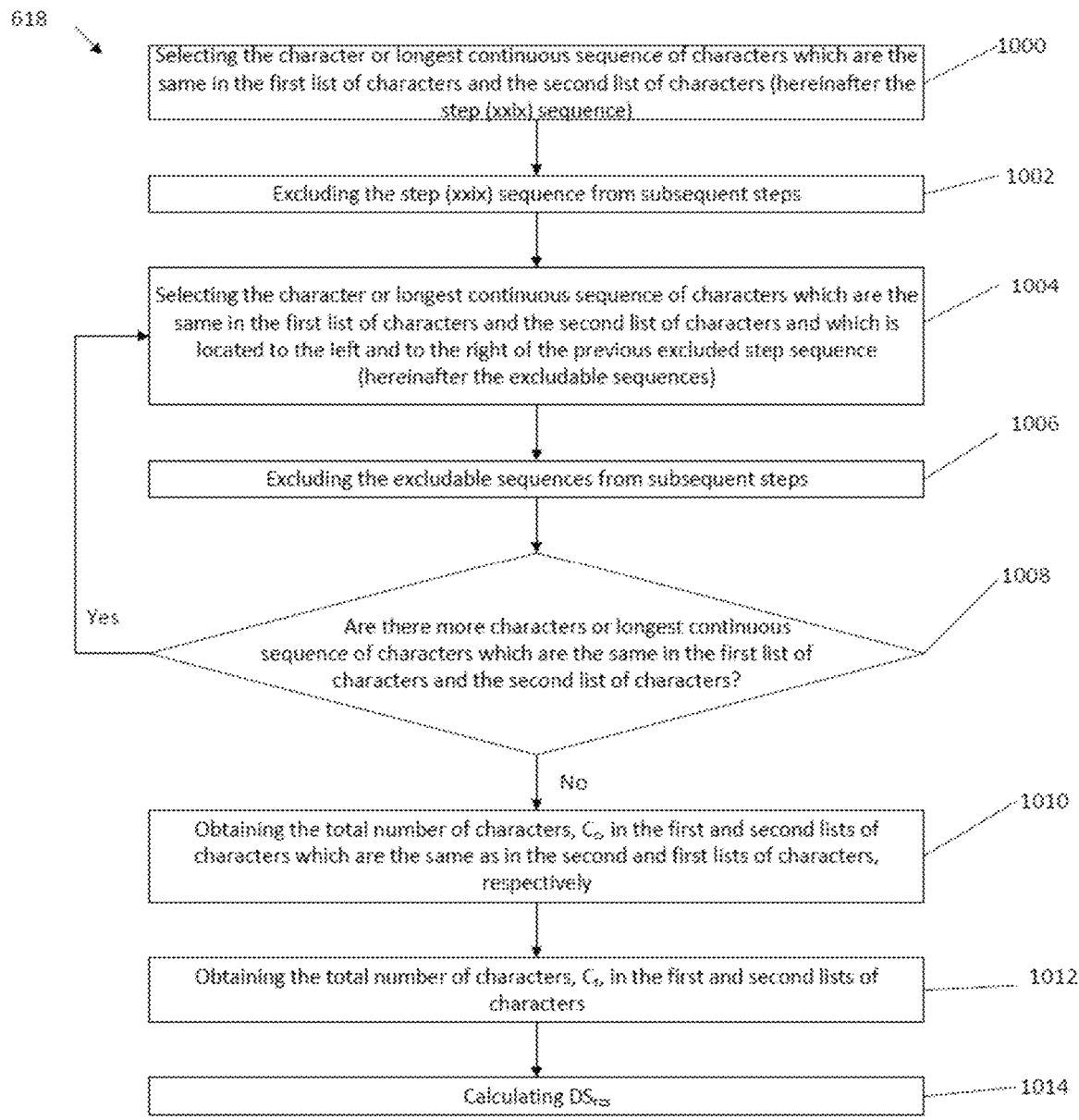

FIG. 24B. Flowchart of an example of a step for determining the reverse complementary degree of similarity ($DS_{rcs}$) in accordance with another embodiment of the present invention.

DETAILED DESCRIPTION OF THE INVENTION

The present invention relates to a method for quantifying the level of disease. In particular, the present invention relates to a method for quantifying the level of minimal residual disease (MRD) using biological techniques and a computer program product (exemplified in FIGS. 20 and 23). The present invention also relates to a method for treating said disease which comprises a step of administering therapy to a subject followed by a step using said method for quantifying the level of disease using biological techniques and a computer program product (exemplified in FIGS. 19 and 22).

In particular, in one embodiment the present invention relates to a method for quantifying the level of minimal residual disease (MRD). This method forms the basis for step (B) of the method for treatment of the present invention. MRD is the name given to the disease that remains in a subject after treatment of said disease. Thus, quantifying the level of MRD, as also described in the method of treatment, kit and system of the present invention, means quantifying the number of diseased cells in a subject or quantifying the amount of genetic material that is associated with disease in a subject after treatment of said disease. Preferably, quantifying the level of MRD means quantifying the number of diseased cells in a biological sample or tissue from a subject after treatment of said disease, or quantifying the level of MRD means quantifying the amount of genetic material that is associated with disease in a biological sample or tissue from a subject, after treatment of said disease. A diseased cell may be identified based on the expression or lack of expression of a biological marker on the diseased cell surface and/or inside said diseased cell, or based on the presence of at least one molecule foreign to the cell on the diseased cell surface and/or inside said diseased cell.

In the present invention, the disease is a genetic disease. Said genetic disease is characterised by at least one variant or the absence of said at least one variant in a nucleotide sequence, wherein said variant is preferably a clonotypic nucleotide sequence for immunoglobulin gene rearrangements, high allelic load, a point mutation (SNV), a multiple mutation (MNV), an indel, a long insertion, a long deletion and/or a translocation. More preferably said disease is characterised by high allelic load and/or at least one tumor clonotypic nucleotide sequence for at least one immunoglobulin gene rearrangement, at least one point mutation (SNV), at least one multiple mutation (MNV), at least one indel, at least one long insertion, at least one long deletion and/or at least one translocation. In one preferred embodiment of the invention, the disease is selected from cancer or leukaemia. In a further preferred embodiment of the invention, said disease is selected from a lymphoproliferative disease or a myeloid neoplasia (myeloproliferative neoplasm or myeloproliferative disease), wherein said lymphoproliferative disease is preferably selected from any of multiple myeloma, follicular lymphoma, chronic lymphocytic leukemia, acute lymphoblastic leukemia, hairy cell leukemia, B-cell lymphoma, T-cell lymphoma, Waldenstrom's macroglobulinemia, Wiskott-Aldrich syndrome, lymphocyte-variant hypereosinophilia, pityriasis lichenoides (PL, PLC, PLVA), post-transplant lymphoproliferative disorder, autoimmune lymphoproliferative syndrome (ALPS), more preferably a lymphoproliferative disease selected from multiple myeloma, non-Hodgkin's high- and low-grade lymphoma, and acute or chronic lymphoblastic leukemia, and said myeloid neoplasia is preferably selected from any of chronic myelogenous leukemia (BCR-ABL1—positive), chronic neutrophilic leukemia, polycythemia vera, primary myelofibrosis, essential thrombocythemia, chronic eosinophilic leukemia, mastocytosis and acute myeloid leukaemia, more preferably a myeloid neoplasm selected from acute myeloid leukemia, myelodysplastic syndrome, myeloproliferative (myeloid) neoplasia and myeloproliferative myelodysplastic syndrome. In another further preferred embodiment of the invention, said disease is selected from multiple myeloma, follicular lymphoma, mantle cell lymphoma, Hodgkin's lymphoma, non-Hodgkin's lymphoma, Burkitt's lymphoma, acute lymphoblastic leukaemia, acute myeloid leukaemia, chronic lymphocytic leukaemia, chronic myelogenous leukaemia, acute monocytic leukemia, atypical chronic myeloid leukemia, juvenile myelomonocytic leukaemia, myelodysplastic syndrome, myeloproliferative neoplasm and myeloproliferative myelodysplastic syndrome. Even more preferably, said disease is selected from acute lymphoblastic leukaemia, acute myeloid leukaemia, chronic lymphocytic leukaemia, chronic myelogenous (or myeloid) leukemia, follicular lymphoma, mantle cell lymphoma, multiple myeloma, breast cancer or neuroblastoma. Most preferably, said disease is selected from multiple myeloma or acute myeloid leukemia.

Said disease is preferably characterised by:
- a point mutation (SNV), multiple mutation (MNV), and/or indel;
- a long insertion and/or translocation; or
- a patient-specific immunoglobulin rearrangement. Furthermore preferably, said disease is characterised by:
- a point mutation (SNV), multiple mutation (MNV), and/or indel selected from a FLT3 internal tandem duplication (FLT3-ITD) or a nucleophosmin1 (NMP1) mutation in acute myeloid leukaemia;
- a long insertion and/or translocation selected from t(9;22) BCR-Abl or t(12;21) ETV6-RUNX1 (TEL-AML1) in acute lymphoblastic leukaemia; t(15;17) PML-RARa, t(8;21) AML1-RUNX1T1 (AML-ETO) or inv(16) CBFb/MYH11 in acute myeloid leukaemia; t(9;22) BCR-Abl in chronic myeloid leukaemia, t(14;18) IgH/BCL2 in follicular lymphoma; t(11;14) IgH/CCND1 (IgH/BCL1) in mantle cell lymphoma, or t(4;14) in multiple myeloma; or
- a patient-specific immunoglobulin rearrangement in acute lymphoblastic leukaemia, multiple myeloma, mantle cell lymphoma, follicular lymphoma, chronic lymphocytic leukaemia or acute lymphoblastic leukaemia. Further, the method of the present invention may be applied to any of the haematological neoplasias disclosed in Hauwel M., Matthes T. "*Minimal residual disease monitoring: the new standard for treatment evaluation of haematological malignancies?*"; Swiss Med Wkly. (2014) 144:w13907].

In an alternative embodiment, the method for quantifying the level of MRD of the invention is therefore a method for quantifying the level of allelic load and/or at least one clonotypic nucleotide sequence for at least one immunoglobulin gene rearrangement, at least one point mutation (SNV), at least one multiple mutation (MNV), at least one indel, at least one long insertion, at least one long deletion and/or at least one translocation in a subject who has been treated for a disease, preferably a subject who has been treated for the disease according to the method of treatment of the present invention.

Treatment of disease in a subject comprises administering therapy to a subject (block 102 of FIG. 19). Said therapy is selected from chemotherapy, immunotherapy or radiotherapy, or combinations thereof. Preferably, said therapy is chemotherapy. More preferably, said chemotherapy comprises administration of:
- bortezomib plus melphalan and prednisone (VMP) and lenalidomide plus dexamethasone (Rd), and/or
- administration of cytarabine and an anthracycline antibiotic or an anthracenedione, optionally followed by administration of cytarabine.

In an even more preferred embodiment, said chemotherapy consists of:
- between 9 and 18 cycles of treatment, each cycle comprising administration of bortezomib plus melphalan and prednisone (VMP) and lenalidomide plus dexamethasone (Rd), or
- 1 or 2 cycles of treatment, each cycle comprising administration of cytarabine over 7 days and subsequent administration of an anthracycline antibiotic or an anthracenedione over 3 days (post-induction treatment), or
- 1 or 2 cycles of treatment, each cycle comprising administration of cytarabine over 7 days and subsequent administration of an anthracycline antibiotic or an anthracenedione over 3 days (postinduction treatment), optionally followed by 1 or 2 cycles of treatment each comprising administration of cytarabine (post-consolidation treatment).

In a furthermore preferred embodiment of the present invention, said chemotherapy consists of between 9 and 18 cycles of treatment, each cycle comprising administration of bortezomib plus melphalan and prednisone (VMP) and lenalidomide plus dexamethasone (Rd), when said disease is multiple myeloma or any lymphoproliferative disease. In another furthermore preferred embodiment of the present invention, said chemotherapy consists of 1 or 2 cycles of treatment (with between 30 and 35 days between cycles), each cycle comprising administration of cytarabine over 7 days and subsequent administration of an anthracycline antibiotic or an anthracenedione over 3 days (post-induction treatment), when said disease is acute myeloid leukemia or any myeloid neoplasia. In yet another furthermore preferred embodiment of the present invention, said chemotherapy consists of 1 or 2 cycles of treatment (with between 30 and 35 days between cycles), each cycle comprising administration of cytarabine over 7 days and subsequent administration of an anthracycline antibiotic or an anthracenedione over 3 days, followed by 1 or 2 cycles of treatment each comprising administration of cytarabine (post-consolidation treatment), when said disease is acute myeloid leukemia or any myeloid neoplasia. In one embodiment of the method of treatment of the present invention the anthracycline antibiotic or anthracenedione is idarubicin.

In the present invention, the level of MRD is quantified in a subject who has been treated for said disease by a method comprising seven steps, (a) to (g) [collectively exemplified in block 104 of FIG. 19, and further exemplified for a method 104 comprising step (a) in blocks 200 and 202, step (b) in blocks 204 and 206, step (c) in block 208, step (d) in block 210, step (e) in block 212, step (f) in block 214 and step (g) in block 216 of FIG. 20]. These seven steps are preferably performed without the need to access an external database comprising data obtained from a population of subjects. Said steps are performed using biological techniques and at least one computer program product.

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may include, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and kits according to embodiments and/or steps of the invention. It will be understood that each square or diamond-shaped block of the flowchart illustrations and/or block diagrams, and combinations of blocks in the flowchart illustrations and/or block diagrams, can be implemented by biological techniques or computer readable program instructions, or combinations thereof.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The step (a) comprises the sequential steps (biological techniques) of:
amplifying by polymerase chain reaction using primers, at least one nucleotide sequence comprised in an amount, D, of genomic DNA of a biological sample obtained from said subject after treatment for said disease, wherein the genomic DNA has an average weight, k, per diploid cell of said biological sample (block 200 of FIG. 20); and
sequencing said at least one nucleotide sequence to obtain at least one first list of characters reading from left to right (block 202 of FIG. 20).

In an analogous manner, the step (b) comprises the sequential steps of:
amplifying by polymerase chain reaction using the same primers as in step (a), at least one nucleotide sequence in a biological sample obtained from said subject prior to treatment for said disease (block 204 of FIG. 20); and
sequencing said at least one nucleotide sequence to obtain at least one second list of characters reading from left to right (block 206 of FIG. 20). Step (a) may be performed simultaneously with step (b), or step (a) may be performed before or after step (b). Preferably, step (b) is performed before step (a).

The biological sample in steps (a) and (b) comprises a sample of biological matter taken from a subject. Said biological sample comprises at least one nucleotide sequence in at least one cell. Preferably said biological sample comprises at least one nucleotide sequence in the genomic DNA of at least one cell in a tissue, blood, urine, faeces, saliva, mucus, sperm, bone, hair and/or nails. The biological sample in step (a) is a test (or follow-up) sample diagnostic for minimal residual disease. The biological sample in step (b) is a diagnosis (or calibration or control) sample diagnostic for the disease prior to a treatment. Preferably, the biological sample in step (b) is a sample with high allelic or clonal load which was taken before treatment of the disease from the same subject as the biological sample in step (a). The biological sample in step (a) has an average weight, k, of genomic DNA per diploid cell.

Each nucleotide sequence in the genomic DNA is amplified by PCR using primers, whereby said primers comprise a forward primer and a reverse primer which bind to different complementary sequences on the Watson and Crick strands adjacent to said nucleotide sequence, thereby identifying the 5' and 3' limits of said nucleotide sequence. In particular, the 3' end of the nucleotide sequence of the Watson strand begins with the nucleotide which is adjacent to the nucleotide at the 5' end of the sequence that is annealed with the forward primer. Conversely, the 5' end of the nucleotide sequence of the Watson strand begins with the nucleotide complementary to the nucleotide which is adjacent to the nucleotide at the 5' end of the sequence that is annealed with the reverse primer. Likewise, the 3' end of the nucleotide sequence of the Crick strand begins with the nucleotide which is adjacent to the nucleotide at the 5' end of the sequence that is annealed with the reverse primer. Conversely, the 5' end of the nucleotide sequence of the Crick strand begins with the nucleotide complementary to the nucleotide which is adjacent to the nucleotide at the 5' end of the sequence that is annealed with the forward primer. Accordingly, a DNA polymerase attaches to the 5' end of the aforementioned primers and replicates the nucleotide sequence multiple times.

Figure 1:
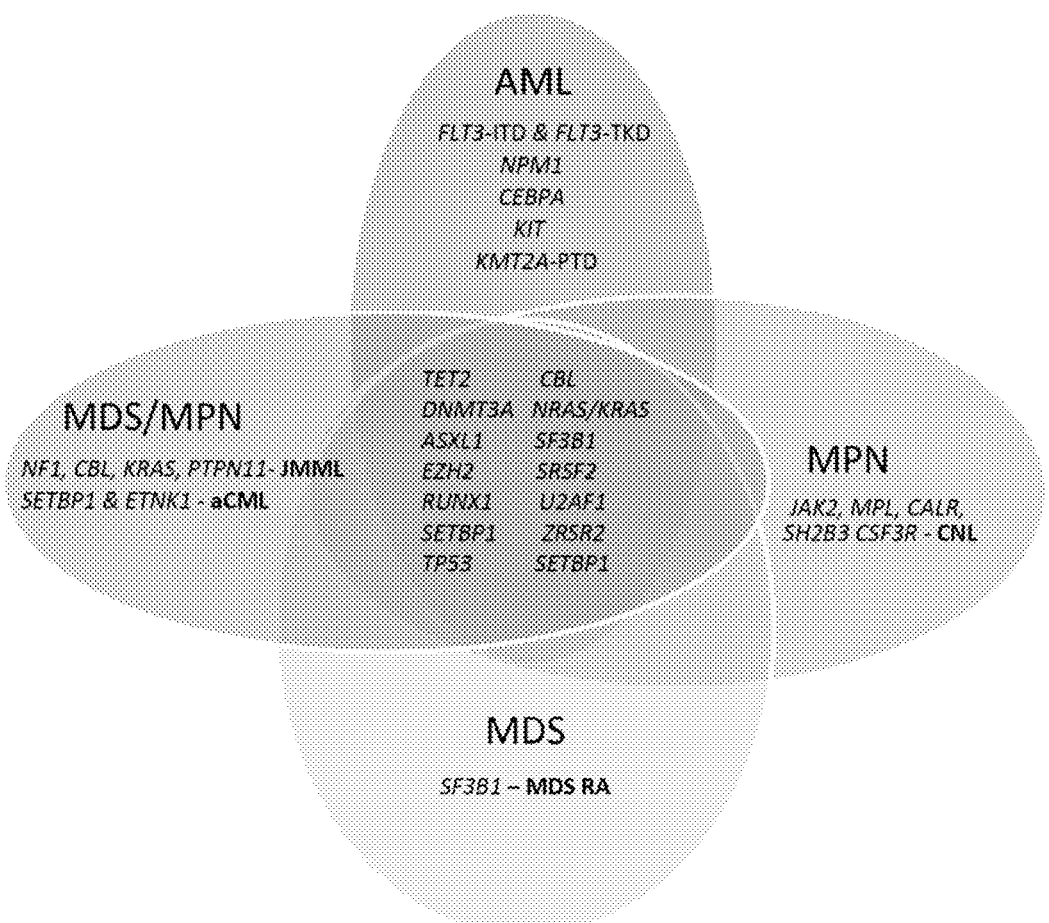
FIG. 1. Overlapping nature of recurrent gene mutations in myeloid neoplasms. Minimal residual disease is detectable through following said gene mutations for, among other diseases, acute myeloid leukemia, myelodysplastic syndrome, myeloproliferative (myeloid) neoplasia and myeloproliferative myelodysplastic syndrome. Genes listed in italics. aCML=atypical chronic myeloid leukemia, AML=acute myeloid leukemia, ITD=internal tandem duplications, JMML=juvenile myelomonocytic leukaemia, MDS=myelodysplastic syndrome, MPN myeloproliferative neoplasms, RA=refractory anaemia, TKD=tyrosine kinase domain.

Preferably the primers are locus-specific primers chosen so as to identify at least one specific variant of a nucleotide sequence present in the biological sample in step (b), wherein said at least one variant or the absence of said at least one variant is indicative of disease. In particular, said at least one variant preferably comprises at least one clonotypic nucleotide sequence for at least one immunoglobulin gene rearrangement, at least one point mutation (SNV), at least one multiple mutation (MNV), at least one indel, at least one long insertion and/or at least one translocation. The at least one specific variant of a nucleotide sequence present in the biological sample obtained from the subject prior to treatment for the disease is the at least one specific variant of a nucleotide sequence which is indicative of said disease and identified in said biological sample in greatest proportion. In this way, determination of B-cell clonality using biological techniques, such as that shown in Example 1 of the present invention for detection of minimal residual disease in a patient treated for multiple myeloma, also finds utility in detection of minimal residual disease in a patient treated for any other lymphoproliferative disease such as follicular lymphoma, chronic lymphocytic leukemia, acute lymphoblastic leukemia, hairy cell leukemia, B-cell lymphoma, T-cell lymphoma, Waldenstrom's macroglobulinemia, Wiskott-Aldrich syndrome, lymphocyte-variant hypereosinophilia, pityriasis lichenoides (PL, PLC, PLVA), post-transplant lymphoproliferative disorder, autoimmune lymphoproliferative syndrome (ALPS), preferably a lymphoproliferative disease selected from multiple myeloma, non-Hodgkin's high- and low-grade lymphoma, and acute or chronic lymphoblastic leukemia. On the other hand, the overlapping nature of some recurrent gene mutations in myeloid neoplasms means that determining the degree of mutation in a gene such as DNMT3A (as shown for the detection of minimal residual disease in patients treated with acute myeloid leukemia in Example 5, below) using biological techniques not only allows detection of minimal residual disease in a patient who has been treated for acute myeloid leukemia, but also allows detection of minimal residual disease in other patients who have been treated for any other myeloid neoplasm which results from a mutation in the same gene such as chronic myelogenous leukemia (BCR-ABL1—positive), chronic neutrophilic leukemia, polycythemia vera, primary myelofibrosis, essential thrombocythemia, chronic eosinophilic leukemia, mastocytosis, preferably a myeloid neoplasm selected from acute myeloid leukemia, myelodysplastic syndrome, myeloproliferative (myeloid) neoplasia and myeloproliferative myelodysplastic syndrome, as shown in FIG. 1. Thus, each specific variant indicative of said disease is identified using biological techniques and the proportion of each specific variant is compared, with the specific variant or specific variants which is or are ranked in greatest proportion respectively being that or those which locus-specific primers are chosen to identify using a computer program product. It should be noted that in one embodiment the process of ranking is a step which is carried out by the FrequencyRank.java script.

Preferably, the primers for quantifying the level of MRD in patients with diseases listed in the present invention are selected from primers that can be used to detect B-cell clonality or mutations in any of the genes listed in FIG. 1. More preferably, said primers are selected from any of the sequences of SEQ.ID.NO. 1 to SEQ.ID.NO. 153 disclosed in Tables 1, 2, 3, 4 or 7. In a preferred embodiment, said primers are selected from any of SEQ.ID.NO. 39 to SEQ.ID.NO. 137, SEQ.ID.NO. 138 and 139, SEQ.ID.NO. 140 and 141, SEQ.ID.NO. 148 and 149, SEQ.ID.NO. 150 and 151, or SEQ.ID.NO. 152 and 153. In a more preferred embodiment, wherein said primers are selected from:
 any of SEQ.ID.NO. 150 and 151 or SEQ.ID.NO. 152 and 153 when said disease is any myeloid neoplasm; or
 any of SEQ.ID.NO. 39 to SEQ.ID.NO. 137 when said disease is multiple myeloma; or
 any of SEQ.ID.NO. 138 and 139, SEQ.ID.NO. 140 and 141, SEQ.ID.NO. 148 and 149, SEQ.ID.NO. 150 and 151 or SEQ.ID.NO. 152 and 153 when said disease is acute myeloid leukemia.

In one embodiment, the primers for quantifying the level of MRD in patients with lymphoproliferative diseases such as multiple myeloma, Hodgkin's high- and low-grade lymphoma or acute and chronic lymphoblastic leukemia are preferably selected from primers that can be used to detect B-cell clonality. More preferably, these primers are selected from any of the primer sequences of SEQ.ID.NO. 1 to SEQ.ID.NO. 137 disclosed in Tables 1, 2, 3 and 4. Even more preferably, these primers are selected from any of the primer sequences of SEQ.ID.NO. 39 to SEQ.ID.NO. 137 disclosed in Tables 3 and 4, preferably when said disease is multiple myeloma.

In another embodiment, the primers for quantifying the level of MRD in patients with myeloid neoplasias such as acute myeloid leukemia, myelodysplastic syndrome, myeloproliferative (myeloid) neoplasia and myeloproliferative myelodysplastic syndrome are preferably selected from primers that can be used to detect mutations in any of the genes listed in FIG. 1. More preferably, these primers are selected from any of the primer sequences of TIB MOLBIOL, Roche Diagnostics, SL, or those manufactured specifically for use with the Ion AmpliSeq™, Thermo Fisher Scientific, Inc kits, specifically the Ion AmpliSeq™ AML Panel, but may contain proprietary modifications. Even more preferably, these primers are selected from any of the primer sequences of SEQ.ID.NO. 138 to SEQ.ID.NO. 153 disclosed in Table 7. Most preferably, these primers are selected from any of the primer sequences of SEQ.ID.NO. 138 and 139, SEQ.ID.NO. 140 and 141, SEQ.ID.NO. 148 and 149, SEQ.ID.NO. 150 and 151 or SEQ.ID.NO. 152 and 153 disclosed in Table 7 when said disease is acute myeloid leukemia or from any of the primer sequences of SEQ.ID.NO. 150 and 151 or SEQ.ID.NO. 152 and 153 disclosed in Table 7 when said disease is any myeloid neoplasm.

As a consequence of the fact that at least one specific variant of a nucleotide sequence is thus identified in steps (a) and (b), and/or more than one type of primer may be used in steps (a) and (b), the steps (a) and (b) involves identifying, amplifying and sequencing at least one nucleotide sequence (i.e. one or more nucleotide sequences) in a biological sample using biological techniques, thus affording at least one list of characters (i.e. one or more lists of characters) corresponding thereto. However, in a more preferred embodiment, the primers used in steps (a) and (b) are a locus-specific forward primer and locus specific reverse primer chosen so as to identify one specific variant of a nucleotide sequence present in the biological samples, wherein said one variant or the absence of said one variant is indicative of disease. Thus, in this preferred embodiment, the step (b) comprises the sequential steps of:

amplifying by polymerase chain reaction using the same locus-specific forward primer and locus specific reverse primer used in step (a), a nucleotide sequence in a biological sample obtained from said subject prior to treatment for said disease of said nucleotide sequence; and sequencing said nucleotide sequence to obtain a second list of characters reading from left to right.

Thus, amplification of at least one nucleotide sequence present in each biological sample is performed with specific primers identifying at least one region of interest (i.e. at least one specific variant indicative of the disease for which a subject has been treated), before processing each on a massively parallel sequencing platform. Accordingly, the test sample on this at least one region of interest was amplified and sequenced with higher, or equal to, expected sensitivity coverage. For amplification of the test sample, an amount, D, of genomic DNA (gDNA) from said test (follow-up) sample is used in PCR, and amplification is preferably repeated until a quantity sufficient for sequencing with a desired sensitivity is obtained. Preferably, an amount, D, of gDNA from said test sample is used in PCR to ensure that a sensitivity equivalent to that obtainable from sampling a given number of cells is obtained. The sensitivity is determined in every instance for application to the study of disease and residual circulating tumor cells.

The amount, D, of the genomic DNA from the test (follow-up) sample which is used in PCR for sequencing with a desired sensitivity (S) is established first by measuring the concentration of DNA ([DNA], pg/µL) in the biological sample obtained from a subject after treatment for said disease (test sample). This value is then used to determine the number of equivalent cells per microliter (N) of the test sample according to the following formula:

$$N=[DNA]/k$$

wherein N and [DNA] are as defined above, and k is the average weight of the genomic DNA per diploid cell of the test sample, whereby k preferably assumes a value of 6.49 picograms per cell. The number of equivalent cells per microliter (N) of the test sample subsequently allows calculation of the volume of sample (V, µL) which it is necessary to use in the PCR in order to reach a desired sensitivity (S) according to the following formula:

$$V=1/(N \times S)$$

A sensitivity of $10^{-5}$ equates with that achievable from use of genomic DNA from at least 100,000 equivalent cells. The volume of test sample (V) determines the number of PCR experiments necessary to obtain a sufficient amount (D, pg) of genomic DNA for sequencing and, in addition, is used to calculate the amount (D) of the genomic DNA from the test sample which is used in PCR according to the following formula:

$$D=[DNA] \times V$$

Amplification may be performed using a PCR instrument and the aforementioned primers by any one of the following PCR biological techniques selected from multiplex-PCR, and single PCR using a pair of primers. Preferably amplification is performed by multiplex-PCR.

Optionally, steps (a) and (b) may comprise a further step of isolating said at least one amplified nucleotide sequence prior to the step of sequencing using routine methods in the art. Thus, the first step of steps (a) and (b) comprises amplification of at least one nucleotide sequence obtained from at least one longer nucleotide sequence by selective amplification of said at least one nucleotide sequence over said at least one longer nucleotide sequence, wherein each longer nucleotide sequence comprises a polynucleotide, wherein said polynucleotide is preferably selected from double- or single-stranded DNA or RNA, more preferably double-stranded DNA, furthermore preferably double stranded genomic DNA. When said polynucleotide is single-stranded DNA, a complementary sequence is synthesised therefrom prior to carrying out steps (a) or (b) to afford double-stranded DNA. When said polynucleotide is RNA, a complementary double-stranded DNA is synthesised (retrotranscribed) therefrom prior to carrying out steps (a) or (b).

The at least one nucleotide sequence of each of steps (a) and (b), thus amplified and optionally isolated using biological techniques, is subsequently sequenced. Sequencing of a nucleotide sequence of step (a) using the biological techniques herein described, affords a first list of characters reading from left to right corresponding thereto, wherein each first list of characters has a total number of characters, $C_f$. Moreover, the total number of first lists of characters (Li) corresponds to the total number of different nucleotide sequences in step (a). Sequencing of a nucleotide sequence of step (b) using the biological techniques herein described, likewise affords a second list of characters reading from left to right, corresponding thereto.

The sequencing performed in each of steps (a) and (b), is a multiplex and/or high-throughput nucleotide sequencing biological technique. Preferably, the sequencing is performed by a next-generation sequencing (NGS) technique, more preferably massively parallel sequencing [e.g. massively parallel signature sequencing (MPSS)] on a massively parallel sequencing platform. In one embodiment of the present invention, when multiple primers are used in sequencing, the sequencing steps in steps (a) and (b) are performed using barcodes to identify between the different primers used. In one especially preferred embodiment of the present invention, the sequencing is performed by massively parallel sequencing using emulsion-PCR.

Each of the separate steps of amplifying and sequencing said at least one nucleotide sequence in steps (a) and (b) are biological techniques and may be performed by separate means (i.e. by separate instruments). Alternatively, two or all of these separate steps may be performed by the same instrument.

Sequencing of a nucleotide sequence in steps (a) and (b) affords a corresponding list of characters, whereby each character in each list of characters comprises a letter. In one embodiment of the present invention, sequencing of a nucleotide sequence in steps (a) and (b) affords a corresponding list of characters, whereby each character in each list of characters comprises a letter associated with a number (or symbol). More preferably, each letter represents the nucleotide that is identified at the corresponding position in the nucleotide sequence which has the highest quality (Q) within the limits of the sequencing method, and the number or symbol associated therewith is the quality (Q), wherein Q is an integer mapping of the probability that the letter which represents a nucleotide that is identified at the corresponding position in the nucleotide sequence is incorrect. Thus, each of the lists of characters obtained in steps (a) and (b) of the present invention is preferably comprised in a sequence format file, more preferably a FASTQ file.

Alternatively, each character more preferably represents the nucleotide that is identified at the corresponding position in the nucleotide sequence in greatest proportion. In one furthermore preferred embodiment of this alternative, the letter associated with said character represents the nucleotide that is identified at the corresponding position in the nucleotide sequence in highest proportion and the number or symbol associated therewith is the proportion (e.g. as a percentage, fraction or ratio) of said nucleotide that is identified therein.

A continuous sequence of characters is a list which is unbroken by another character or absence of a character, wherein said continuous sequence of characters represents an unbroken continuous sequence of nucleotides. Analogous with that described above, each character in the continuous sequence of characters comprises one or more letter, preferably one or more letter associated with a number or symbol, more preferably wherein each letter represents the nucleotide that is identified at the corresponding position in the nucleotide sequence which has the highest quality (Q) within the limits of the sequencing method, and the number or symbol associated therewith is the quality (Q), wherein Q is an integer mapping of the probability that the letter which represents a nucleotide that is identified at the corresponding position in the nucleotide sequence is incorrect. As such, in this more preferred embodiment of the invention, said continuous sequence of characters comprises a continuous sequence of letters representing a continuous sequence of nucleotides, when each character in the continuous sequence of characters represents the nucleotide that is identified at the corresponding position which has the highest quality (Q) within the limits of the sequencing method.

Alternatively, each character in the continuous sequence of characters preferably comprises a letter associated with a number or symbol, more preferably wherein each letter represents the nucleotide that is identified at the corresponding position in the nucleotide sequence in greatest proportion. In one embodiment of this more preferred alternative, the letter associated with said character in the continuous sequence of characters represents the nucleotide that is identified at the corresponding position in the nucleotide sequence in highest proportion and the number or symbol associated therewith is the proportion (e.g. as a percentage, fraction or ratio) of said nucleotide that is identified therein. As such, in this more preferred alternative embodiment, said continuous sequence of characters comprises a continuous sequence of letters representing a continuous sequence of nucleotides, when each character in the continuous sequence of characters represents the nucleotide that is identified at the corresponding position in the continuous sequence of nucleotides in greatest proportion.

Each character in each list of characters corresponds to one nucleotide in said nucleotide sequence and the order of characters in said list corresponds to the order of nucleotides in said nucleotide sequence. Thus, the character at the left-hand end of said list corresponds to the nucleotide or proportion of nucleotides at the 3' end of the Watson strand of said nucleotide sequence and the character at the right-hand end of said list corresponds to the nucleotide or proportion of nucleotides at the 5' end of the Watson strand of said nucleotide sequence. Analogously, a complementary (or partly complementary) list of characters is obtained representing each Crick strand of said nucleotide sequence, whereby the character at the left-hand end of said list corresponds to the nucleotide or proportion of nucleotides at the 3' end of the Crick strand of said nucleotide sequence and the character at the right-hand end of said list corresponds to the nucleotide or proportion of nucleotides at the 5' end of the Crick strand of said nucleotide sequence.

Subsequently, comparison of each first list of characters obtained in step (a) is made with each second list of characters obtained in step (b). Said comparison is made so as to ultimately determine the total number of first lists of characters, $L_c$, which are the same as a second list of characters. In other words, the comparison is made so as to determine the $L_c$ which are identical with (i.e. match) a second list of characters. In order to determine $L_c$, it is necessary to determine the degree of similarity of each first list of characters obtained in step (a) with each second list of characters obtained in step (b), wherein a degree of similarity, DS, is determined for a first list of characters obtained in step (a) with a second list of characters obtained in step (b). Although methods adapted to bioinformatics are known which access external data (e.g. genetic databases derived from populations) in order to carry out the comparison step and somehow implement "biological knowledge" the method of the present invention works without the need to access external data. To this end, the first feature that is considered essential to implement is a fuzzy logic. The rate of failure of sequencers using a classical binary logic—in which sequences can only be equal or different—is so high that it is not useful. A high proportion (nearly all) of nucleotide sequences that evaluate as different, are equal but appear as different because of an error in the sequencer. Therefore, a comparison process to evaluate the degree of similarity between any two lists of characters is implemented.

In one embodiment of the invention, each character in a list of characters comprises a letter, such that a character in the first list of characters is determined as the same as a character in the second list of characters, when the letter is the same in the first and second lists of characters (i.e. a character in one list of characters is determined as the same as a character in another list of characters when the letters are the same in each list). In one preferred embodiment of the invention, each character in a list of characters comprises a letter associated with a number or symbol, more preferably wherein each letter represents the nucleotide that is identified at the corresponding position in the nucleotide sequence in the highest quality (Q) within the limits of the sequencing method and wherein each number or symbol represents the quality (Q). Thus, in said more preferred embodiment of the method of the invention, wherein each character in a first list of characters and each character in a second list of characters comprises a letter associated with a number or symbol, wherein said number or symbol represents quality (Q) and wherein said letter represents the nucleotide that is identified at the corresponding position in the nucleotide sequence having the highest quality (Q), a character in the first list of characters is determined as the same as a character in the second list of characters, when the letter having the highest quality is the same in the first and second lists of characters (i.e. a character in one list of characters is determined as the same as a character in another list of characters when the letters are the same in each list). Further to this, not only the letters but also the numbers or symbols associated therewith may be compared between lists, preferably by comparing the letter and the number or symbol representing the quality (Q) associated therewith for each character in each list. Thus, in a yet more preferred embodiment of the method of the invention, a character in one list of characters which comprises a letter associated with a quality (Q) is determined as the same as a character in another list of characters which comprises a letter associated with a quality (Q'), when the letter having the highest quality is the same in each list, and the quality (Q) of letters is the same in each list within a cut-off limit or an error, more preferably a cut-off limit. For example, a character at a given position which is assigned as T with a quality of 1.00 (i.e. 100%) may be considered the same as a character at a given position which is assigned as T with a quality of 0.99 (i.e. 99%), when the cut-off limit is set at 0.99 (i.e. the error is set at 1%). Thus, in the following step (c), each step of selecting the character or longest continuous sequence of characters which are the same, within a cut-off limit, in the first and second lists of characters or parts thereof, comprises firstly making the aforementioned comparison between the first list of characters and the second list of characters or parts thereof, and secondly choosing the character or longest continuous sequence of characters based on the criteria given in the following, when one or more characters or one or more continuous sequences of characters are identified as longest from said comparison. In this method, the cut-off limit is preferably set at a quality (Q) of 0.99, more preferably at 0.999, furthermore preferably at 0.9999, most preferably 0.99999, and/or the error is set at a maximum of 1%, more preferably 0.1%, furthermore preferably 0.01%, most preferably 0.001%. In one yet more preferred embodiment of the method of the invention, a character in a first list of characters is determined as the same as a character in a second list of characters, when the letter having the highest quality (Q) is the same in the first and second lists of characters, and the quality of the letter in the first list of characters is within 0.01 (1%) of the quality of the letter in the second list of characters, furthermore preferably within 0.001 (0.1%), still more preferably within 0.0001 (0.01%), most preferably within 0.00001 (0.001%).

Alternatively, comparison is performed by comparing the letter comprising each character which is present in greatest quality (Q) or in greatest proportion in each list of characters. Thus, in the method of the invention, a character in one list of characters is determined as the same as a character in another list of characters preferably when the letters are the same.

Alternatively, comparison is performed by comparing the proportion of each one or more letter comprising each character. Thus, comparison is performed by comparing the proportion of each one or more nucleotide that is identified at each position in the nucleotide sequence. In this method, a character in one list of characters is determined as the same as a character in another list of characters when the proportion of letters is the same within error. For example, a character for which the proportion of A at a given position is 0.11 and the proportion of T at said given position is 0.89 (i.e. the ratio of A:T is 0.11:0.89) may be considered the same as a character for which the proportion of A at a given position is 0.1 and the proportion of T at said given position is 0.9 (i.e. the ratio of A:T is 0.1:0.9), when the error is set at 5% error. Thus, in the following step (c), each step of selecting the character or longest continuous sequence of characters which are the same in the first list of characters and second list of characters or parts thereof comprises firstly making the aforementioned comparison between the first list of characters and second list of characters or parts thereof, and secondly choosing the character or longest continuous sequence of characters based on the criteria given in the following, when one or more characters or one or more continuous sequences of characters are identified as longest from said comparison. In this method, the error is set at a maximum of 1%, more preferably 0.1%, furthermore preferably 0.01%, most preferably 0.001%.

Figure 2:
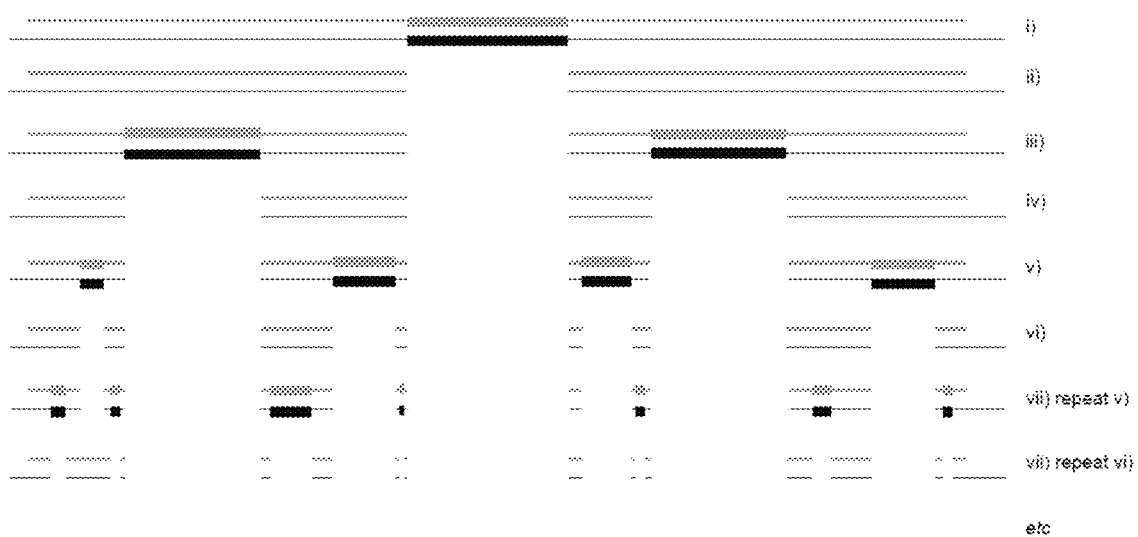
FIG. 2. Schematic diagram representing sub-steps (i) to (vii) of step (c) according to the invention, wherein the narrow grey line (--------) represents a first character list and the narrow black line (———) represents a second character list. Selection of a character or longest continuous sequence of characters which are the same in the first list of characters and the second list of characters is represented by broader lines (▦▦▦▦) and (■■■■), respectively, that are subsequently excluded from the aforementioned character lists.
Figure 3:
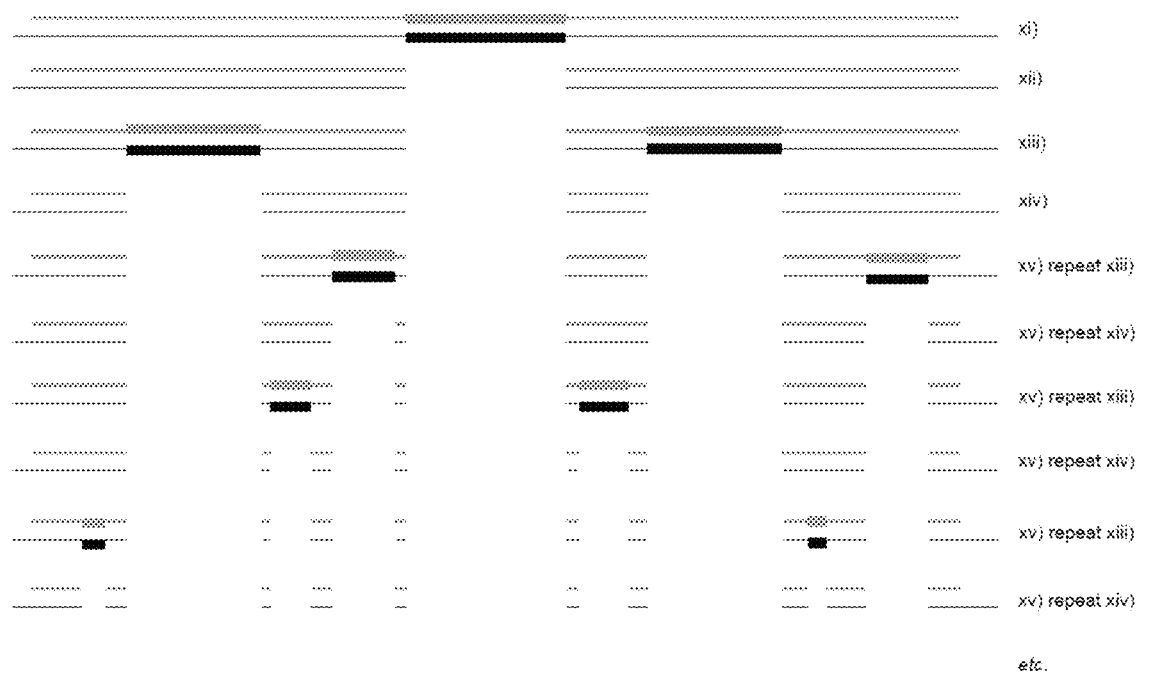

Thus, for each first list of characters obtained in step (a), the degree of similarity with each second list of characters obtained in step (b) is subsequently determined in step (c) (block 208 of FIG. 20), wherein a degree of similarity, DS, of a first list of characters obtained in step (a) with a second list of characters obtained in step (b) is determined either by sub-steps (i) to (x) [sub-steps (i) to (vii) of which are represented schematically in FIG. 2] or (xi) to (xviii) [sub-steps (xi) to (xv) of which are represented schematically in FIG. 3]. FIGS. 21A and 21B disclose flowcharts of examples of a step (method) 208 for determining the degree of similarity (DS) in accordance with an embodiment of the present invention.

In particular, a degree of similarity, DS, of a first list of characters obtained in step (a) with a second list of characters obtained in step (b) is determined either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 300 of FIG. 21A);

(ii) excluding the character or longest continuous sequence of characters selected in step (i) from subsequent steps of selecting a character or longest continuous sequence of characters which is the same in the first list of characters and the second list of characters (block 302 of FIG. 21A);

(iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected (block 304 of FIG. 21A);

(iv) excluding each character and/or each longest continuous sequence of characters selected in step (iii) from subsequent steps of selecting a character or longest continuous sequence of characters which is the same in the first list of characters and the second list of characters (block 306 of FIG. 21A);

(v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected (block 308 of FIG. 21A);

(vi) excluding each character and/or each longest continuous sequences of characters selected in step (v) from subsequent steps of selecting a character or longest continuous sequence of characters which is the same in the first list of characters and the second list of characters (block 310 of FIG. 21A);

(vii) repeating steps (v) and (vi) until no character or longest continuous sequence of characters which is the same in the first list of characters and the second list of characters is selected (decided in block 312 of FIG. 21A);

(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively (block 314 of FIG. 21A);

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters (block 316 of FIG. 21A); and (x) calculating DS according to the following formula:

$$DS = C_c/C_t$$

(block 318 of FIG. 21A)

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 400 of FIG. 21B);

(xii) excluding the character or longest continuous sequence of characters selected in step (xi) from subsequent steps of selecting a character or longest continuous sequence of characters which is the same in the first list of characters and the second list of characters (block 402 of FIG. 21B);

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected (block 404 of FIG. 21B);

(xiv) excluding each character and/or each longest continuous sequence of characters selected in step (xiii) from subsequent steps of selecting a character or longest continuous sequence of characters which is the same in the first list of characters and the second list of characters (block 406 of FIG. 21B);

(xv) repeating steps (xiii) and (xiv) until no character or longest continuous sequence of characters which is the same in the first list of characters and the second list of characters is selected (decided in block 408 of FIG. 21B);

(xvi) adding up
the number of characters in the first list of characters which were excluded in any of the steps (xi) to (xv); and
the number of characters in the second list of characters which were excluded in any of the steps (xi) to (xv)
to obtain the total number of characters, $C_c$, in the first and second lists of characters which are the same as in the second and first lists of characters, respectively (block 410 of FIG. 21B);

(xvii) adding up
$C_c$; and
the number of characters in the first list of characters which are located between the characters and/or longest continuous sequences of characters that were excluded from the first list of characters, and which were not excluded in any of the steps (xi) to (xv) of step (c); and
the number of characters in the second list of characters which are located between the characters and/or longest continuous sequences of characters that were excluded from the second list of characters, and which were not excluded in any of the steps (xi) to (xv) of step (c),
to obtain the total number of characters, $C_t$, in the first and second lists of characters (block 412 of FIG. 21B); and (xviii) calculating DS according to the following formula:

$$DS = C_c/C_t$$

(block 414 of FIG. 21B).

In step (c), the sub-steps (i) and (xi) of selecting the character which is the same in the first and second lists of characters involve comparing individual characters in the first and second lists of characters according to the foregoing criteria for comparison. Moreover, the sub-steps (i) and (xi) of selecting the longest continuous sequence of characters which is the same in the first and second lists of characters involve comparing consecutive individual characters in the first and second lists of characters according to the foregoing criteria for comparison. It should be noted that sub-steps (i) to (iv) and (xi) to (xiv) are identical.

In step (c), after each step of selecting the character or longest continuous sequence of characters which are the same in the first and second lists of characters or parts thereof, a step of excluding said character or longest continuous sequence of characters, thus selected, takes place, wherein each step of excluding comprises removing the character or longest continuous sequence of characters, thus selected, from consideration in subsequent steps of selecting the character or longest continuous sequence of characters which is the same in the first and second lists of characters. It should be noted that each step of excluding results in a non-continuous sequence of characters which is broken at the point between each character which flanks the character or longest continuous sequence of characters, thus excluded. As such, any subsequent step of selecting the character or longest continuous sequence of characters which are the same in the first and second lists of characters or parts thereof in sub-steps (v) to (vii) of step (c) does not consider a sequence which extends beyond a previously excluded character or longest continuous sequence of characters, but instead considers the continuous sequence of characters located adjacent to each character or each longest continuous sequence of characters excluded in the previous step. Moreover, any subsequent step of selecting the character or longest continuous sequence of characters which are the same in the first and second lists of characters or parts thereof in sub-steps (xiii) to (xv) will not consider a sequence which bridges the characters on either side of the excluded character or longest continuous sequence of characters.

Each cycle of selecting and excluding a character or longest continuous sequence of characters which is the same in the first and second lists of characters is repeated until no character or longest continuous sequence of characters which is the same in the first and second lists of characters is selected. In sub-steps (iii) and (xiii) of step (c) of the present invention, selection is preferably repeated simultaneously for the continuous sequence of characters which is located to the left of the character or longest continuous sequence of characters excluded in sub-steps (ii) and (xii), respectively, and for the continuous sequence of characters which is located to the right of the character or longest continuous sequence of characters excluded in sub-steps (ii) and (xii), respectively. Alternatively, this may be repeated first for the continuous sequence of characters which is located to the left of the character or longest continuous sequence of characters excluded in sub-steps (ii) and (xii), respectively, and then for the continuous sequence of characters which is located to the right of the character or longest continuous sequence of characters excluded in sub-steps (ii) and (xii), respectively. Alternatively, this may be repeated first for the continuous sequence of characters which is located to the right of the character or longest continuous sequence of characters excluded in sub-steps (ii) and (xii), respectively, and then for the continuous sequence of characters which is located to the left of the character or longest continuous sequence of characters excluded in sub-steps (ii) and (xii), respectively.

Analogously, in sub-step (v) of step (c) of the present invention, selection is preferably repeated simultaneously for the continuous sequence of characters to the immediate left of each character or each longest continuous sequence of characters excluded in the previous step, and for the continuous sequence of characters to the immediate right of each character or each longest continuous sequence of characters excluded in the previous step. Alternatively, this may be repeated first for the continuous sequence of characters to the immediate left of each character or each longest continuous sequence of characters excluded in the previous step, and then for the continuous sequence of characters to the immediate right of each character or each longest continuous sequence of characters excluded in the previous step. Alternatively, this may be repeated first for the continuous sequence of characters to the immediate right of each character or each longest continuous sequence of characters excluded in the previous step, and then for the continuous sequence of characters to the immediate left of each character or each longest continuous sequence of characters excluded in the previous step.

Each of these approaches is novel compared to standard implementations and generates a marginally more compact comparison result.

Moreover, in a preferred embodiment of step (c), each step of selecting the character or longest continuous sequence of characters is a step of selecting the longest continuous sequence of characters, wherein said longest continuous sequence of characters comprises a minimum of two characters. As such, each cycle of selecting and excluding a character or longest continuous sequence of characters which is the same in the first and second lists of characters is repeated in step (c) until no longest continuous sequence of characters having a minimum of two characters which is the same in the first and second lists of characters is selected. More preferably, said longest continuous sequence of characters comprises a minimum of 3 characters, furthermore preferably a minimum of 4 characters.

Once it is not possible to select a character or longest continuous sequence of characters which is the same in the first list of characters and second list of characters (because all characters or longest continuous sequences of characters which are the same in the first list of characters and second list of characters have been excluded), the total number of characters, $C_c$, which were excluded in the first list of characters and excluded in the second list of characters is obtained by sub-steps (viii) and/or (xvi) of step (c), wherein the number of characters in the first list of characters which were respectively excluded in any of the sub-steps (i) to (vii) and (xi) to (xv) and the number of characters in the second list of characters which were respectively excluded in any of the sub-steps (i) to (vii) and (xi) to (xv) is added up. The total number of characters, $C_c$, which were excluded in the first and second lists of characters may also be thought of as 2×(the number of characters which were excluded in the first list of characters), or as 2×(the number of characters which were excluded in the second list of characters). Analogously, the total number of characters, $C_t$, in the first list of characters is obtained by sub-steps (ix) and/or (xvii) of step (c), wherein $C_c$, plus the number of characters in the first list of characters which are located between the characters and/or longest continuous sequences of characters that were excluded from the first list of characters which were not excluded in any of the sub-steps (i) to (vii) and (xi) to (xv) of step (c), plus the number of characters in the second list of characters which are located between the characters and/or longest continuous sequences of characters that were excluded from the second list of characters which were not excluded in any of the sub-steps (i) to (vii) and (xi) to (xv) of step (c), is added up.

The degree of similarity, DS, of a first list of characters obtained in step (a) with a second list of characters obtained in step (b) is preferably determined in step (c) of the invention using at least one computer program product. Thus, the method of the present invention is intended to detect a list of characters representing a specific nucleotide sequence, which is supplied as an argument to the method, within a data file that contains a mix of lists of characters each representing a nucleotide sequence fragmented in places that, from an informatics point of view are considered random. Therefore, the at least one lists of characters in the mix have random lengths and it is not known in advance where a list of characters representing a specific nucleotide sequence [in step (b)] can be found in each at least one list of characters. Thus, the method of the present invention comprises a combination of alignment and comparison. Since it comprises a mix of alignment and comparison, it is considered that in the invention, comparison is made only from the first character or longest continuous sequence of characters which is the same in the first list of characters and the second list of characters and the last character or longest continuous sequence of characters which is the same in the first and second lists of characters (i.e. including and between the matching characters or longest continuous sequences of characters closest to the extremes of the first and second lists of characters), whereby $C_c$ and $C_t$ are determined over that portion of the first and second lists of characters which is from the first character or longest continuous sequence of characters which is the same in the first and second lists of characters and the last character or longest continuous sequence of characters which is the same in the first and second lists of characters. Accordingly, in a preferred embodiment, each of the characters or longest continuous sequences of characters which are eliminated in either of sub-steps (i) to (vii) or (xi) to (xv) of step (c) are placed in a .dna file and sub-steps (viii) and (xvi) may use the data in a .dna file to calculate $C_c$ using a -trim option, such that comparison is made only between the first and the last character or longest continuous sequence of characters in the first list which are the same as in the second list.

Subsequent to step (c), a step (d) is carried out, in which for each first list of characters obtained in step (a), the DS of highest value, $DS_{HV}$, is selected (block 210 of FIG. 20). However, by virtue of the fact that each nucleotide sequence in steps (a) and (b) (arbitrarily herein defined as the Watson strand) has a complementary nucleotide sequence (in particular the reverse complementary sequence, arbitrarily herein defined as the Crick strand), such that first list of characters obtained in step (a) and a second list of characters obtained in step (b) also have a corresponding reverse complementary first list of characters and a corresponding reverse complementary second list of characters, respectively, in a preferred embodiment, not only the aforementioned nucleotide sequence in steps (a) and (b) but also the complementary nucleotide sequence may be subjected to steps (a), (b) and (c) of the method of the invention. FIGS. 24A and 24B disclose flowcharts of a step 618 of determining the reverse complementary degree of similarity ($DS_{rcs}$), thereby exemplifying the alternatives of said step of determining the reverse complementary degree of similarity in the following particularly preferred embodiment of the present invention. Thus, in said preferred embodiment, the step (d) comprises:

amplifying by polymerase chain reaction using primers, each at least one nucleotide sequence which is the reverse complementary sequence complementary to the at least one nucleotide sequence in step (a), and sequencing said at least one reverse complementary nucleotide sequence to obtain at least one reverse complementary first list of characters reading from left to right; and amplifying by polymerase chain reaction using the same primers as in the previous step, each at least one nucleotide sequence which is the reverse complementary sequence complementary to the at least one nucleotide sequence in step (b), and sequencing said at least one reverse complementary nucleotide sequence to obtain at least one reverse complementary second list of characters reading from left to right; and determining, for each reverse complementary first list of characters obtained in step (a), the degree of similarity with each reverse complementary second list of characters obtained in step (b), wherein a degree of similarity, $DS_{rcs}$, of a reverse complementary first list of characters obtained in step (a) with a reverse complementary second list of characters obtained in step (b) is determined either by:

(xix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected (block 900 of FIG. 24A);

(xx) excluding the character or longest continuous sequence of characters selected in step (xix) from subsequent steps of selecting a character or longest continuous sequence of characters which is the same in the reverse complementary first list of characters and the reverse complementary second list of characters (block 902 of FIG. 24A);

(xxi)—selecting the character or longest continuous sequence of characters which is located to the left of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 904 of FIG. 24A);

(xxii) excluding each character and/or each longest continuous sequence of characters selected in step (xxi) from subsequent steps of selecting a character or longest continuous sequence of characters which is the same in the reverse complementary first list of characters and the reverse complementary second list of characters (block 906 of FIG. 24A);

(xxiii)—selecting the character or longest continuous sequence of characters which is located in the continuous sequence of characters to the immediate left of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located in the continuous sequence of characters to the immediate right of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 908 of FIG. 24A);

(xxiv) excluding each character and/or each longest continuous sequences of characters selected in step (xxiii) from subsequent steps of selecting a character or longest continuous sequence of characters which is the same in the reverse complementary first list of characters and the reverse complementary second list of characters (block 910 of FIG. 24A);

(xxv) repeating steps (xxiii) and (xxiv) until no character or longest continuous sequence of characters which is the same in the reverse complementary first list of characters and the reverse complementary second list of characters is selected (decided in block 912 of FIG. 24A);

(xxvi) adding up
the number of characters in the reverse complementary first list of characters which were excluded in any of the steps (xix) to (xxv); and
the number of characters in the reverse complementary second list of characters which were excluded in any of the steps (xix) to (xxv)
to obtain the total number of characters, $C_c$, in the reverse complementary first and second lists of characters which are the same as in the reverse complementary second and first lists of characters, respectively (block 914 of FIG. 24A);

(xxvii) adding up
$C_c$; and
the number of characters in the reverse complementary first list of characters which are located between the characters and/or longest continuous sequences of characters that were excluded from the reverse complementary first list of characters, and which were not excluded in any of the steps (xix) to (xxv) of step (c); and
the number of characters in the reverse complementary second list of characters which are located between the characters and/or longest continuous sequences of characters that were excluded from the reverse complementary second list of characters, and which were not excluded in any of the steps (xix) to (xxv) of step (c),
to obtain the total number of characters, $C_t$, in the reverse complementary first and second lists of characters (block 916 of FIG. 24A); and (xxviii) calculating DS according to the following formula:

$$DS_{res} = C_c/C_t$$

(block 918 of FIG. 24A)
or by:

(xxix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected (block 1000 of FIG. 24B);

(xxx) excluding the character or longest continuous sequence of characters selected in step (xxix) from subsequent steps of selecting a character or longest continuous sequence of characters which is the same in the reverse complementary first list of characters and the reverse complementary second list of characters (block 1002 of FIG. 24B);

(xxxi)—selecting the character or longest continuous sequence of characters which is located to the left of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 1004 of FIG. 24B);

(xxxii) excluding each character and/or each longest continuous sequence of characters selected in step (xxxi) from subsequent steps of selecting a character or longest continuous sequence of characters which is the same in the reverse complementary first list of characters and the reverse complementary second list of characters (block 1006 of FIG. 24B);

(xxxiii) repeating steps (xxxi) and (xxxii) until no character or longest continuous sequence of characters which is the same in the reverse complementary first list of characters and the reverse complementary second list of characters is selected (decided in block 1008 of FIG. 24B);

(xxvi) adding up
the number of characters in the reverse complementary first list of characters which were excluded in any of the steps (xix) to (xxv); and
the number of characters in the reverse complementary second list of characters which were excluded in any of the steps (xix) to (xxv)
to obtain the total number of characters, $C_c$, in the reverse complementary first and second lists of characters which are the same as in the reverse complementary second and first lists of characters, respectively (block 1010 of FIG. 24B);

(xxvii) adding up
$C_c$; and
the number of characters in the reverse complementary first list of characters which are located between the characters and/or longest continuous sequences of characters that were excluded from the reverse complementary first list of characters, and which were not excluded in any of the steps (xix) to (xxv) of step (c); and
the number of characters in the reverse complementary second list of characters which are located between the characters and/or longest continuous sequences of characters that were excluded from the reverse complementary second list of characters, and which were not excluded in any of the steps (xix) to (xxv) of step (c), to obtain the total number of characters, $C_t$, in the reverse complementary first and second lists of characters (block 1012 of FIG. 24B); and (xxviii) calculating DS according to the following formula:

$$DS_{rcs}=C_c/C_t$$

(block 1014 of FIG. 24B)

wherein when DS is determined for each first list of characters obtained in step (a) using sub-steps (i) to (x), $DS_{rcs}$ is determined for each corresponding reverse complementary first list of characters using sub-steps (xix) to (xxviii), and when DS is determined for each first list of characters obtained in step (a) using sub-steps (xi) to (xviii), $DS_{rcs}$ is determined for each corresponding reverse complementary first list of characters using sub-steps (xxix) to (xxxvi); and selecting, for each first list of characters obtained in step (a) and its corresponding reverse complementary first list of characters, the DS or $DS_{rcs}$ of highest value, $DS_{HV}$ (following on from block 1014 of FIG. 24B but not shown therein).

Thus, a DS or $DS_{rcs}$ of 0.0 means that no characters in a first list of characters are the same as in a second list of characters, whereas a DS or $DS_{rcs}$ of 1.0 means that all characters in a first list of characters are the same as in a second list of characters (i.e. a nucleotide sequence from a biological sample from a subject after treatment for said disease is strictly equal with a nucleotide sequence from a biological sample obtained from a subject prior to treatment for said disease). Therefore, the method of the present invention provides information on how many nucleotide sequences in the biological sample from a subject contain the argument sequence (the nucleotide sequence from a biological sample obtained from a subject with said disease), either in its original (Watson) form or in its reverse complement (Crick) version. The degree of similarity of highest value, $DS_{HV}$, is preferably selected in step (d) of the invention using at least one computer program product.

Having determined $DS_{HV}$ for each of the at least one first list of characters obtained in step (a), the number of first lists of characters obtained in step (a) which have a $DS_{HV}$ that is greater than a threshold value, T, is subsequently added up in a step (e) to obtain the total number of first lists of characters, $L_c$, which are the same as a second list of characters (block 212 of FIG. 20). Similarly, in a step (f), $L_c$ and the number of first lists of characters which do not have a $DS_{HV}$ that is greater than T are added up to obtain Li (block 214 of FIG. 20). Li corresponds to the total number of first lists of characters. Preferably said threshold value, T, for the DS and $DS_{rcs}$ is set at 0.99, more preferably at 0.999, furthermore preferably at 0.9999, most preferably at 0.99999. Steps (e) and (f) may be performed simultaneously or step (e) may be performed before or after step (f), preferably step (f) is performed after step (e). Moreover, the total number of first lists of characters, $L_c$, which are the same as a second list of characters and the total number of first lists of characters, Li, are each preferably obtained in steps (e) and (f) of the invention, respectively, using at least one computer program product.

Finally, a step (g) is performed to calculate the level of MRD (block 216 of FIG. 20). Calculating the level of MRD is performed according to either of the following formulae:

$$MRD=(L_c \times k)/(L_t \times D)$$

or $$MRD=L_c/L_t$$

or $$MRD=L_c \times (D/k)/L_t^2$$

wherein $L_c$, D, k and $L_t$ are as previously defined, and as defined below:

$L_c$=total number of first lists of characters which are the same as a second list of characters;

D=amount, D, of genomic DNA from a biological sample obtained from a subject after treatment for a disease (from which said at least one first list of characters is obtained by sequencing);

k=average weight, k, of genomic DNA per diploid cell from a biological sample obtained from a subject after treatment for a disease;

$L_t$=total number of first lists of characters. The level of minimal residual disease, MRD, is preferably calculated in step (g) of the invention using at least one computer program product.

In one embodiment of the invention, an MRD of 1 is 100% indicative of disease in said subject and an MRD of 0 is 0% indicative of disease in said subject. In other words, an MRD of 1 indicates that said subject is suffering from said disease, whereas an MRD of 0 indicates that the subject is free of any disease (at least in the cells or tissue of the biological sample). As such, the MRD may be used to diagnose the presence of said disease in said subject and/or to determine the best therapeutic approach (if needed).

In particular, in the method of treatment of the present invention, when the level of MRD is >0 (decided in block 106 of FIG. 19) steps A and B are repeated, until the level of MRD measured at the end of each cycle of steps A and B=0 and therapy is considered complete (block 108 of FIG. 19). In other words, the method of treatment of the present invention involves a step A of treating the subject for the disease and a step B of quantifying the level of MRD following said treatment and, if said disease persists in said subject following said treatment, the step A of treating the subject for the disease and the subsequent step B of quantifying the level of MRD following said treatment, are repeated until the disease no longer persists in said subject. In the method of treatment of the present invention, each repetition of step A comprises administering the same therapy as previously administered to said subject or administering therapy different to that previously administered to said subject. Preferably, the same therapy as previously administered to said subject is re-administered in all subsequent repetitions of step A.

In the method of treatment of the present invention, steps A and B are repeated until the level of MRD measured at the end of each cycle of steps A and B=0. However, steps A and B are preferably repeated for a maximum of 4 cycles of steps A and B, more preferably for 3 cycles of steps A and B, even more preferably for a maximum of two cycles of steps A and B, provided that the level of MRD is >0 at the end of each cycle of steps A and B.

The disease is considered to no longer persist in said subject, the level of MRD=0. In a preferred embodiment, when the level of MRD is >$10^{-6}$ said disease is considered to persist in said subject. More preferably, when said disease is a lymphoproliferative disease and the level of MRD is >$10^{-6}$; or when said disease is a myeloid neoplasia and the level of MRD is >$10^{-5}$, said disease is considered to persist in said subject. In one even more preferred embodiment of the method for treatment of the present invention [exemplified by the flowchart of FIG. 22, with a method 500 for treatment of disease in a subject, wherein said disease is a haematological cancer selected from multiple myeloma or acute myeloid leukaemia, following administration of therapy (block 502 of FIG. 22) and quantifying the level of MRD in said subject according to the method disclosed herein (block 504 of FIG. 22)], when the therapy is chemotherapy and:

when said disease is multiple myeloma and the level of MRD is $>10^{-6}$ (decided in block 506 of FIG. 22), preferably $>10^{-5}$; or when said disease is acute myeloid leukemia and the level of MRD is $>10^{-5}$ (decided in block 508 of FIG. 22), preferably $>2.5 \times 10^{-4}$:

minimal residual disease is considered to persist in the subject and steps A (block 502 of FIG. 22) and B (block 504 of FIG. 22) are repeated.

In a furthermore-preferred embodiment, when said disease is multiple myeloma and said therapy is chemotherapy which consists of between 9 and 18 cycles of treatment, each cycle comprising administration of bortezomib plus melphalan and prednisone (VMP) and lenalidomide plus dexamethasone (Rd), and the level of MRD is calculated according to either of the following formulae:

$$MRD=(L_c \times k)/(L_t \times D)$$

or $$MRD=L_c \times (D/k)/L_t^2$$

and is $>10^{-5}$, minimal residual disease (multiple myeloma) is considered to persist in the subject and steps A and B are repeated, wherein each repetition of step A preferably comprises administering the same chemotherapy as previously administered. Similarly, in another furthermore-preferred embodiment, when said disease is acute myeloid leukemia and said therapy is chemotherapy which consists of 1 or 2 cycles of treatment, each cycle comprising administration of cytarabine over 7 days and subsequent administration of an anthracycline antibiotic or an anthracenedione over 3 days, and the level of MRD is calculated according to the following formula:

$$MRD=L_c/L_t$$

and is $>10^{-3}$, minimal residual disease (acute myeloid leukemia) is considered to persist in the subject and steps A and B are repeated, wherein each repetition of step A preferably comprises administering the same chemotherapy as previously administered. Likewise, in another furthermore-preferred embodiment, when said disease is acute myeloid leukemia and said therapy is chemotherapy which consists of 1 or 2 cycles of treatment, each cycle comprising administration of cytarabine over 7 days and subsequent administration of an anthracycline antibiotic or an anthracenedione over 3 days, followed by 1 or 2 cycles of treatment each comprising administration of cytarabine, and the level of MRD is calculated according to the following formula:

$$MRD=L_c/L_t$$

and is $>2.5 \times 10^{-4}$, minimal residual disease (acute myeloid leukemia) is considered to persist in the subject and steps A and B are repeated steps A and B are repeated, wherein each repetition of step A preferably comprises administering the same chemotherapy as previously administered. The level of MRD equates with the sensitivity of the method for quantifying the level of MRD, namely the presence of disease with the capacity to develop relapse versus the absence of disease with the capacity to develop relapse. Thus, the method of quantifying the level of MRD [equivalent to a step (B) of the method of treatment, as disclosed herein], the kit and the system of the present invention provide a level of MRD which, when greater than the aforementioned threshold values, diagnose the presence of disease in said subject with the capacity to develop relapse and, hence, the need for further treatment. Conversely, the method of quantifying the level of MRD [equivalent to a step (B) of the method of treatment, as disclosed herein], the kit and the system of the present invention provide a level of MRD which, when less than the aforementioned threshold values, diagnose the absence of said disease in said subject and, hence, avoid further treatment being administered. Consequently, the present invention provides a method of treatment that is specific to the requirements of the patient and ensures that the disease is treated sufficiently as to eliminate all minimal residual disease yet avoid unnecessarily subjecting said patient to therapy beyond that which is required to treat the disease.

In one embodiment, the MRD is produced as an output (preferably in the form of a file, or on a screen or piece of paper) after step (d) has been performed. Preferably, the MRD, together with at least one first list of characters is produced as an output (preferably in the form of a file, or on a screen or piece of paper) detailing the character or longest continuous sequence of characters which is the same in the first and second lists of characters. Optionally, said output details the $C_c$, $C_t$, DS, $DS_{HV}$, D, k, $L_c$ and/or Li, where relevant with the $DS_{rcs}$.

In a particularly preferred embodiment, the present invention relates to a method for quantifying the level of minimal residual disease (MRD) in a subject, equivalent to a step (B) of a particularly preferred embodiment of the method of treatment of the present invention, wherein said subject has been treated for said disease using chemotherapy, wherein said disease is selected from a lymphoproliferative disease or a myeloid neoplasia, which comprises:

(a)—amplifying by polymerase chain reaction using a PCR instrument and primers, at least one nucleotide sequence comprised in an amount, D, of genomic DNA of a biological sample obtained from said subject after treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease; and sequencing said at least one nucleotide sequence on a massively parallel sequencing platform to obtain at least one first list of characters reading from left to right, wherein said sequencing is massively parallel sequencing;

(b)—amplifying by polymerase chain reaction using a PCR instrument and the same locus-specific forward primer and the same locus-specific reverse primer as in step (a), at least one nucleotide sequence in a biological sample obtained from said subject prior to treatment for said disease; and sequencing said at least one nucleotide sequence on a massively parallel sequencing platform to obtain at least one second list of characters reading from left to right, wherein said sequencing is massively parallel sequencing;

(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined using at least one computer program product, either by:
(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
(ii) excluding the character or longest continuous sequence of characters selected in step (i) from subsequent steps of selecting a character or longest continuous sequence of characters which is the same in the first list of characters and the second list of characters;
(iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;
(iv) excluding each character and/or each longest continuous sequence of characters selected in step (iii) from subsequent steps of selecting a character or longest continuous sequence of characters which is the same in the first list of characters and the second list of characters;
(v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;
(vi) excluding each character and/or each longest continuous sequences of characters selected in step (v) from subsequent steps of selecting a character or longest continuous sequence of characters which is the same in the first list of characters and the second list of characters;
(vii) repeating steps (v) and (vi) until no character or longest continuous sequence of characters which is the same in the first list of characters and the second list of characters is selected;
(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;
(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters; and
(x) calculating DS according to the following formula:

$$DS=C_c/C_t$$

or by:
(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
(xii) excluding the character or longest continuous sequence of characters selected in step (xi) from subsequent steps of selecting a character or longest continuous sequence of characters which is the same in the first list of characters and the second list of characters;
(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and
selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up the number of characters in the first list of characters which were excluded in any of the steps (xi) to (xv); and the number of characters in the second list of characters which were excluded in any of the steps (xi) to (xv)

to obtain the total number of characters, $C_c$, in the first and second lists of characters which are the same as in the second and first lists of characters, respectively;

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters; and (xviii) calculating DS according to the following formula:

$$DS=C_c/C_t$$

(d) selecting using at least one computer program product, for each first list of characters obtained in step (a), the DS of highest value, $DS_{HV}$;

(e) adding up using at least one computer program product, the number of first lists of characters which have a $DS_{HV}$ that is greater than a threshold value, T, to obtain the total number of first lists of characters, $L_c$, which are the same as a second list of characters;

(f) adding up, using at least one computer program product, $L_c$; and the number of first lists of characters which do not have a $DS_{HV}$ that is greater than T, to obtain the total number of first lists of characters, $L_t$; and (g) calculating using at least one computer program product, the level of minimal residual disease (MRD) according to either of the following formulae:

$$MRD=(L_c \times k)/(L_t \times D)$$

or $$MRD=L_c \times (D/k)/L_t^2,$$

when said disease is a lymphoproliferative disease, or calculating using at least one computer program product, the level of minimal residual disease (MRD) according to the following formula:

$$MRD=L_c/L_t$$

when said disease is a myeloid neoplasia, wherein when said disease is a lymphoproliferative disease and the level of MRD is $>10^{-6}$; or when said disease is a myeloid neoplasia and the level of MRD is $>10^{-5}$: steps A and B are repeated, wherein each repetition of step A comprises administering the same chemotherapy as previously administered to said subject or chemotherapy different to that previously administered to said subject.

FIG. 23 discloses a flowchart of a method 504 of quantifying the level of minimal residual disease in a subject, exemplifying the following particularly preferred embodiment of the present invention. In said especially preferred embodiment, the present invention relates to a method for quantifying the level of minimal residual disease (MRD) in a subject, equivalent to a step (B) of an especially preferred embodiment of the method of treatment of the present invention, wherein said subject has been treated for said disease, without the need to access an external database comprising data obtained from a population of subjects, wherein said disease is selected from a lymphoproliferative disease or a myeloid neoplasia, which comprises:

(a)—amplifying by polymerase chain reaction using a PCR instrument and primers, at least one nucleotide sequence comprised in an amount, D, of genomic DNA of a biological sample obtained from said subject after treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease (block 600 of FIG. 23); and sequencing said at least one nucleotide sequence on a massively parallel sequencing platform to obtain at least one first list of characters reading from left to right, wherein said sequencing is massively parallel sequencing (block 602 of FIG. 23);

(b)—amplifying by polymerase chain reaction using a PCR instrument and the same locus-specific forward primer and the same locus-specific reverse primer as in step (a), at least one nucleotide sequence in a biological sample obtained from said subject prior to treatment for said disease (block 604 of FIG. 23); and sequencing said at least one nucleotide sequence on a massively parallel sequencing platform to obtain at least one second list of characters reading from left to right, wherein said sequencing is massively parallel sequencing (block 606 of FIG. 23);

(c) determining, for each first list of characters obtained in step (a), the degree of similarity with each second list of characters obtained in step (b) (block 608 of FIG. 23), wherein a degree of similarity, DS, of a first list of characters obtained in step (a) with a second list of characters obtained in step (b) is determined using at least one computer program product, either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 300 of FIG. 21A);

(ii) excluding the character or longest continuous sequence of characters selected in step (i) from subsequent steps of selecting a character or longest continuous sequence of characters which is the same in the first list of characters and the second list of characters (block 302 of FIG. 21A);

(iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected (block 304 of FIG. 21A);

(iv) excluding each character and/or each longest continuous sequence of characters selected in step (iii) from subsequent steps of selecting a character or longest continuous sequence of characters which is the same in the first list of characters and the second list of characters (block 306 of FIG. 21A);

(v) selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected (block 308 of FIG. 21A);

(vi) excluding each character and/or each longest continuous sequences of characters selected in step (v) from subsequent steps of selecting a character or longest continuous sequence of characters which is the same in the first list of characters and the second list of characters (block 310 of FIG. 21A);

(vii) repeating steps (v) and (vi) until no character or longest continuous sequence of characters which is the same in the first list of characters and the second list of characters is selected (decided in block 312 of FIG. 21A);

(viii) adding up the number of characters in the first list of characters which were excluded in any of the steps (i) to (vii); and the number of characters in the second list of characters which were excluded in any of the steps (i) to (vii)

to obtain the total number of characters, $C_c$, in the first and second lists of characters which are the same as in the second and first lists of characters, respectively (block 314 of FIG. 21A);

(ix) adding up $C_c$; and the number of characters in the first list of characters which are located between the characters and/or longest continuous sequences of characters that were excluded from the first list of characters, and which were not excluded in any of the steps (i) to (vii) of step (c); and the number of characters in the second list of characters which are located between the characters and/or longest continuous sequences of characters that were excluded from the second list of characters, and which were not excluded in any of the steps (i) to (vii) of step (c), to obtain the total number of characters, $C_t$, in the first and second lists of characters (block 316 of FIG. 21A); and (x) calculating DS according to the following formula:

$$DS=C_c/C_t$$

(block 318 of FIG. 21A)

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 400 of FIG. 21B);

(xii) excluding the character or longest continuous sequence of characters selected in step (xi) from subsequent steps of selecting a character or longest continuous sequence of characters which is the same in the first list of characters and the second list of characters (block 402 of FIG. 21B);

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected (block 404 of FIG. 21B);

(xiv) excluding each character and/or each longest continuous sequence of characters selected in step (xiii) from subsequent steps of selecting a character or longest continuous sequence of characters which is the same in the first list of characters and the second list of characters (block 406 of FIG. 21B);

(xv) repeating steps (xiii) and (xiv) until no character or longest continuous sequence of characters which is the same in the first list of characters and the second list of characters is selected (decided in block 408 of FIG. 21B);

(xvi) adding up the number of characters in the first list of characters which were excluded in any of the steps (xi) to (xv); and the number of characters in the second list of characters which were excluded in any of the steps (xi) to (xv)

to obtain the total number of characters, $C_c$, in the first and second lists of characters which are the same as in the second and first lists of characters, respectively (block 410 of FIG. 21B);

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters (block 412 of FIG. 21B); and (xviii) calculating DS according to the following formula:

$$DS = C_c/C_t$$

(block 414 of FIG. 21B)

(d)—amplifying by polymerase chain reaction using a PCR instrument and primers, each at least one nucleotide sequence which is the reverse complementary sequence complementary to the at least one nucleotide sequence in step (a), and sequencing on a massively parallel sequencing platform said at least one reverse complementary nucleotide sequence to obtain at least one reverse complementary first list of characters reading from left to right, wherein said primers comprise a locus-specific forward primer and a locus-specific reverse primer, and said primers identify one specific variant of a nucleotide sequence present in said biological sample, wherein said one variant or the absence of said one variant is indicative of disease (blocks 610 and 612 of FIG. 23); and amplifying by polymerase chain reaction using a PCR instrument and the same locus-specific forward primer and the same locus-specific reverse primer as in the previous step, each at least one nucleotide sequence which is the reverse complementary sequence complementary to the at least one nucleotide sequence in step (b), and sequencing on a massively parallel sequencing platform said at least one reverse complementary nucleotide sequence to obtain at least one reverse complementary second list of characters reading from left to right (blocks 614 and 616 of FIG. 23); and determining, for each reverse complementary first list of characters obtained in step (a), the degree of similarity with each reverse complementary second list of characters obtained in step (b) (block 618 of FIG. 23), wherein a degree of similarity, $DS_{rcs}$, of a reverse complementary first list of characters obtained in step (a) with a reverse complementary second list of characters obtained in step (b) is determined using at least one computer program product, either by:

(xix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;

(xx) excluding the character or longest continuous sequence of characters selected in step (xix) from subsequent steps of selecting a character or longest continuous sequence of characters which is the same in the reverse complementary first list of characters and the reverse complementary second list of characters;

(xxi)—selecting the character or longest continuous sequence of characters which is located to the left of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxii) excluding each character and/or each longest continuous sequence of characters selected in step (xxi) from subsequent steps of selecting a character or longest continuous sequence of characters which is the same in the reverse complementary first list of characters and the reverse complementary second list of characters;

(xxiii)—selecting the character or longest continuous sequence of characters which is located in the continuous sequence of characters to the immediate left of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located in the continuous sequence of characters to the immediate right of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxiv) excluding each character and/or each longest continuous sequences of characters selected in step (xxiii) from subsequent steps of selecting a character or longest continuous sequence of characters which is the same in the reverse complementary first list of characters and the reverse complementary second list of characters;

(xxv) repeating steps (xxiii) and (xxiv) until no character or longest continuous sequence of characters which is the same in the reverse complementary first list of characters and the reverse complementary second list of characters is selected;

(xxvi) adding up
the number of characters in the reverse complementary first list of characters which were excluded in any of the steps (xix) to (xxv); and
the number of characters in the reverse complementary second list of characters which were excluded in any of the steps (xix) to (xxv)
to obtain the total number of characters, $C_c$, in the reverse complementary first and second lists of characters which are the same as in the reverse complementary second and first lists of characters, respectively;

(xxvii) adding up
$C_c$; and
the number of characters in the reverse complementary first list of characters which are located between the characters and/or longest continuous sequences of characters that were excluded from the reverse complementary first list of characters, and which were not excluded in any of the steps (xix) to (xxv) of step (c); and
the number of characters in the reverse complementary second list of characters which are located between the characters and/or longest continuous sequences of characters that were excluded from the reverse complementary second list of characters, and which were not excluded in any of the steps (xix) to (xxv) of step (c), to obtain the total number of characters, $C_t$, in the reverse complementary first and second lists of characters; and (xxviii) calculating DS according to the following formula:

$$DS_{res}=C_c/C_t$$

or by:

(xxix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected;

(xxx) excluding the character or longest continuous sequence of characters selected in step (xxix) from subsequent steps of selecting a character or longest continuous sequence of characters which is the same in the reverse complementary first list of characters and the reverse complementary second list of characters;

(xxxi)—selecting the character or longest continuous sequence of characters which is located to the left of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected;

(xxxii) excluding each character and/or each longest continuous sequence of characters selected in step (xxxi) from subsequent steps of selecting a character or longest continuous sequence of characters which is the same in the reverse complementary first list of characters and the reverse complementary second list of characters;

(xxxiii) repeating steps (xxxi) and (xxxii) until no character or longest continuous sequence of characters which is the same in the reverse complementary first list of characters and the reverse complementary second list of characters is selected;

(xxxiv) adding up
the number of characters in the reverse complementary first list of characters which were excluded in any of the steps (xxix) to (xxxiii); and
the number of characters in the reverse complementary second list of characters which were excluded in any of the steps (xxix) to (xxxiii)
to obtain the total number of characters, $C_c$, in the reverse complementary first and second lists of characters which are the same as in the reverse complementary second and first lists of characters, respectively;

(xxxv) adding up
$C_c$; and
the number of characters in the reverse complementary first list of characters which are located between the characters and/or longest continuous sequences of characters that were excluded from the reverse complementary first list of characters, and which were not excluded in any of the steps (xxix) to (xxxiii) of step (c); and
the number of characters in the reverse complementary second list of characters which are located between the characters and/or longest continuous sequences of characters that were excluded from the reverse complementary second list of characters, and which were not excluded in any of the steps (xxix) to (xxxiii) of step (c), to obtain the total number of characters, $C_t$, in the reverse complementary first and second lists of characters; and (xxxvi) calculating DS according to the following formula:

$$DS_{res} = C_e/C_t$$

wherein when DS is determined for each first list of characters obtained in step (a) using sub-steps (i) to (x), $DS_{rcs}$ is determined for each corresponding reverse complementary first list of characters using sub-steps (xix) to (xxviii), and when DS is determined for each first list of characters obtained in step (a) using sub-steps (xi) to (xviii), $DS_{rcs}$ is determined for each corresponding reverse complementary first list of characters using sub-steps (xxix) to (xxxvi); and selecting, using at least one computer program product, for each first list of characters obtained in step (a) and its corresponding reverse complementary first list of characters, the DS or $DS_{rcs}$ of highest value, $DS_{HV}$;

(e) adding up, using at least one computer program product the number of first lists of characters which have a $DS_{HV}$ that is greater than a threshold value, T, to obtain the total number of first lists of characters, $L_c$, which are the same as a second list of characters (block 622 of FIG. 23);

(f) adding up, using at least one computer program product:
$L_c$; and
the number of first lists of characters which do not have a $DS_{HV}$ that is greater than T,
to obtain the total number of first lists of characters, $L_t$ (block 624 of FIG. 23); and (g) calculating, using at least one computer program product, the level of minimal residual disease (MRD) according to either of the following formulae:

$$MRD = (L_c \times k)/(L_t \times D)$$

or $$MRD = L_c/L_t$$

or $$MRD = L_c \times (D/k)/L_t^2$$

(block 216 of FIG. 23);
wherein in sub-steps (iii) and (xiii) of step (c), and sub-steps (xxi) and (xxxi) of step (d) of the present invention, selection is preferably repeated simultaneously for the continuous sequence of characters which is located to the left of the character or longest continuous sequence of characters excluded in sub-steps (ii) and (xii) of step (c), and sub-steps (xx) and (xxx) of step (d), respectively, and for the continuous sequence of characters which is located to the right of the character or longest continuous sequence of characters excluded in sub-steps (ii) and (xii), and sub-steps (xx) and (xxx) of step (d), respectively; and
wherein in sub-step (v) of step (c) and sub-step (xxiii) of step (d), selection is preferably repeated simultaneously for the continuous sequence of characters to the immediate left of each character or each longest continuous sequence of characters excluded in the previous step, and for the continuous sequence of characters to the immediate right of each character or each longest continuous sequence of characters excluded in the previous step.

Moreover, a particularly more preferred embodiment of the present invention relates to a method for treatment of disease in a subject, wherein said disease is a haematological cancer selected from multiple myeloma or acute myeloid leukaemia, comprising the steps of:

(A) administering therapy to a subject, wherein said therapy is chemotherapy, which consists of:

between 9 and 18 cycles of treatment, each cycle comprising administration of bortezomib plus melphalan and prednisone (VMP) and lenalidomide plus dexamethasone (Rd), when said disease is multiple myeloma, or either:
1 or 2 cycles of treatment, each cycle comprising administration of cytarabine over 7 days and subsequent administration of an anthracycline antibiotic or an anthracenedione over 3 days; or 1 or 2 cycles of treatment, each cycle comprising administration of cytarabine over 7 days and subsequent administration of an anthracycline antibiotic or an anthracenedione over 3 days, followed by 1 or 2 cycles of treatment each comprising administration of cytarabine, when said disease is acute myeloid leukemia (B) quantifying the level of minimal residual disease (MRD) in said subject who has been treated for said disease, without the need to access an external database comprising data obtained from a population of subjects, which comprises:

(a)—amplifying by polymerase chain reaction using a PCR instrument and primers, at least one nucleotide sequence comprised in an amount, D, of genomic DNA of a biological sample obtained from said subject after treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease; and sequencing said at least one nucleotide sequence on a massively parallel sequencing platform to obtain at least one first list of characters reading from left to right, wherein said sequencing is massively parallel sequencing;

(b)—amplifying by polymerase chain reaction using a PCR instrument and the same locus-specific forward primer and the same locus-specific reverse primer as in step (a), at least one nucleotide sequence in a biological sample obtained from said subject prior to treatment for said disease; and sequencing said at least one nucleotide sequence on a massively parallel sequencing platform to obtain at least one second list of characters reading from left to right, wherein said sequencing is massively parallel sequencing;

(c) determining, for each first list of characters obtained in step (a), the degree of similarity with each second list of characters obtained in step (b), wherein a degree of similarity, DS, of a first list of characters obtained in step (a) with a second list of characters obtained in step (b) is determined using at least one computer program product, either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(ii) excluding the character or longest continuous sequence of characters selected in step (i) from subsequent steps of selecting a character or longest continuous sequence of characters which is the same in the first list of characters and the second list of characters;

(iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;

(iv) excluding each character and/or each longest continuous sequence of characters selected in step (iii) from subsequent steps of selecting a character or longest continuous sequence of characters which is the same in the first list of characters and the second list of characters;

(v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters; and (x) calculating DS according to the following formula:

$$DS=C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up the number of characters in the first list of characters which were excluded in any of the steps (xi) to (xv); and the number of characters in the second list of characters which were excluded in any of the steps (xi) to (xv)

to obtain the total number of characters, $C_c$, in the first and second lists of characters which are the same as in the second and first lists of characters, respectively;

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters; and (xviii) calculating DS according to the following formula:

$$DS=C_c/C_t$$

(d) selecting using at least one computer program product, for each first list of characters obtained in step (a), the DS of highest value, $DS_{HV}$;

(e) adding up using at least one computer program product, the number of first lists of characters which have a $DS_{HV}$ that is greater than a threshold value, T, to obtain the total number of first lists of characters, $L_c$, which are the same as a second list of characters;

(f) adding up, using at least one computer program product, $L_c$; and the number of first lists of characters which do not have a $DS_{HV}$ that is greater than T, to obtain the total number of first lists of characters, $L_t$; and (g) calculating using at least one computer program product, the level of minimal residual disease (MRD) according to either of the following formulae:

$$MRD=(L_c \times k)/(L_t \times D)$$

or $$MRD=L_c \times (D/k)/L_t^2,$$

when said disease is multiple myeloma, or calculating using at least one computer program product, the level of minimal residual disease (MRD) according to the following formula:

$$MRD=L_c/L_t$$

when said disease is acute myeloid leukaemia, wherein when said disease is multiple myeloma and the level of MRD is $>10^{-6}$ (more preferably the level of MRD is $>10^{-5}$); or when said disease is acute myeloid leukemia and the level of MRD is $>10^{-5}$ (more preferably the level of MRD is $>10^{-3}$):

steps A and B are repeated, wherein each repetition of step A comprises administering the same chemotherapy as previously administered to said subject or chemotherapy different to that previously administered to said subject, preferably the same chemotherapy as previously administered to said subject.

Another embodiment of the invention discloses a kit and a further embodiment of the invention discloses a system, each for quantifying the level of MRD in a subject who has been treated for said disease. In accordance with the foregoing, said kit and said system each comprises:

means for amplifying by polymerase chain reaction using primers, at least one nucleotide sequence comprised in an amount, D, of genomic DNA of a biological sample obtained from said subject after treatment for said disease, wherein the genomic DNA has an average weight, k, per diploid cell of said biological sample; and means for sequencing said at least one nucleotide sequence to obtain at least one first list of characters reading from left to right.

Analogously, said kit and said system each comprises:

means for amplifying by polymerase chain reaction using the same primers as in step (a), at least one nucleotide sequence in a biological sample obtained from said subject prior to treatment for said disease; and means for sequencing said at least one nucleotide sequence to obtain at least one second list of characters reading from left to right.

The means for amplifying a nucleotide sequence by polymerase chain reaction comprises a PCR instrument which operates according to any of the aforementioned biological techniques (preferably an emulsion PCR instrument) and primers according to the aforementioned disclosure. Likewise, the means for sequencing at least one nucleotide sequence to obtain at least one first list of characters reading from left to right comprise a nucleotide sequencing instrument which operates according to any of the aforementioned biological techniques (preferably a massively parallel sequencing instrument). Each of the means for amplifying and sequencing said nucleotide sequence in (a) and (b) may be comprised in different instruments. Alternatively, these means may be comprised within the same instrument.

In addition, the kit of the present invention and the system of the present invention each comprises means (c) for determining, for each first list of characters obtained in step (a), the degree of similarity with each second list of characters obtained in step (b), wherein a degree of similarity, DS, of a first list of characters obtained in step (a) with a second list of characters obtained in step (b) is determined either by:

(i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(ii) excluding the character or longest continuous sequence of characters selected in step (i) from subsequent steps of selecting a character or longest continuous sequence of characters which is the same in the first list of characters and the second list of characters;

(iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;

(iv) excluding each character and/or each longest continuous sequence of characters selected in step (iii) from subsequent steps of selecting a character or longest continuous sequence of characters which is the same in the first list of characters and the second list of characters;

(v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c),
to obtain the total number of characters, $C_t$, in the first and second lists of characters; and (x) calculating DS according to the following formula:

$$DS = C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up
the number of characters in the first list of characters which were excluded in any of the steps (xi) to (xv); and the number of characters in the second list of characters which were excluded in any of the steps (xi) to (xv) to obtain the total number of characters, $C_c$, in the first and second lists of characters which are the same as in the second and first lists of characters, respectively;

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters; and (xviii) calculating DS according to the following formula:

$$DS=C_c/C_t.$$

Preferably said means (c) determines DS, $C_c$ and $C_t$ by providing instructions for each of the steps (i) to (x) and (xi) to (xviii). Furthermore preferably, said means (c) carries out each of the steps (i) to (x) and (xi) to (xviii) as previously disclosed herein. In one embodiment, said means is preferably using a computer program product or, more preferably, at least one computer, at least one circuit, at least one integrated circuit, at least one chip or at least one microchip.

In addition, the kit of the present invention and the system of the present invention each comprises means (d) for selecting, for each first list of characters obtained in step (a), the DS of highest value, $DS_{HV}$, according to the foregoing. The kit of the present invention and the system of the present invention each also comprises means (e) for adding up the number of first lists of characters which have a $DS_{HV}$ that is greater than a threshold value, T, to obtain the total number of first lists of characters, $L_c$, which are the same as a second list of characters. Moreover, the kit of the present invention and the system of the present invention each comprises means (f) for adding up $L_c$; and the number of first lists of characters which do not have a $DS_{HV}$ that is greater than T, to obtain the total number of first lists of characters, $L_t$. Furthermore, the kit of the present invention and the system of the present invention each comprises means (g) for calculating the level of minimal residual disease (MRD) according to either of the following formulae:

$$MRD=(L_c \times k)/(L_t \times D)$$

or $$MRD=L_c/L_t$$

or $$MRD=L_c \times (D/k)/L_t^2.$$

As for means (c), said means (d) to (g) preferably provide instructions for each of the steps disclosed therein. Thus, preferably the kit of the present invention and the system of the present invention each additionally comprises instructions for calculating the level of MRD. The level of MRD is calculated according to the aforementioned disclosure of steps (c) to (g). Said instructions are preferably carried out by a human operator using a computer program product or, more preferably, at least one computer, at least one circuit, at least one integrated circuit, at least one chip or at least one microchip. In a preferred embodiment, said instructions are carried out by means (c) following input of character lists into said means. In a further preferred embodiment of the method of the invention, steps (a) to (g) are performed by the same means, wherein said means comprises a computer program product or, more preferably, at least one computer, at least one circuit, at least one integrated circuit, at least one chip or at least one microchip. Thus, in a further preferred embodiment of the kit of the invention and in a further preferred embodiment of the system of the present invention each, means (a), (b) and (c) are part of the same means, which optionally comprises instructions (d), (e), (f) and (g).

The present invention also relates to use of the method of the invention, the system of the invention or the kit of the invention, according to the aforementioned disclosure, in quantifying the level of minimal residual disease (MRD) in a subject who has been treated for said disease.

The flowchart and block diagrams in the Figures illustrate the architecture, functionality, and operation of possible implementations of systems, methods, and kits according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to embodiments of the invention in the form disclosed. Many modifications and variations will be apparent to those of ordinary skill in the art without departing from the scope and spirit of embodiments of the invention. The embodiment was chosen and described in order to best explain the principles of embodiments of the invention and the practical application, and to enable others of ordinary skill in the art to understand embodiments of the invention for various embodiments with various modifications as are suited to the particular use contemplated.

EXAMPLES

The following examples illustrate the invention and should not be considered as limiting, but rather illustrative of the invention.

Examples Part I

Materials and Methods i) Samples 16 diagnostic bone marrow samples and 24 follow-up bone marrow samples obtained from subjects with said disease (test samples) were used and the series was expanded to 120 cases included in two consecutive clinical assays of Spanish myeloma patients.

ii) DNA Extraction and Quantification from Sample

DNA samples were obtained from bone marrow biopsies using the kit QIAamp DNA mini kit (Qiagen). The quantity and quality (purity) of DNA was determined using Nano-Drop 1000 (Thermo Scientific).

iii) Calculation of Concentration of DNA Corresponding to a Desired Number of Equivalent Cells Per Sample The concentration of DNA ([DNA], pg/μL) in the biological sample obtained from a subject treated for said disease (follow-up or test sample) was measured using Qubit® dsDNA HS Assay Kit. This value was used to determine the number of equivalent cells per microliter (N) of the test sample according to the following formula:

$$N=[DNA]/k$$

wherein N and [DNA] are as defined above, and k refers to a value of 6.49 pg of DNA per diploid cell.

The number of equivalent cells per microliter (N) of the test sample allowed calculation of the volume of sample (V, μL) which it was necessary to use in the PCR in order to reach a desired sensitivity (S) according to the following formula:

$$V=1/(N\times S)$$

The sensitivity was determined by serial dilutions of samples (starting from 1 μg of DNA which was used to ensure a sensitivity of $10^{-5}$ or more) with known quantification of MRD on a polyclonal background (using a pool of healthy controls). A sensitivity of $10^{-5}$ equates with that achievable from use of DNA from at least 100,000 equivalent cells. The volume of sample (V) determines the number of PCR experiments necessary to obtain sufficient DNA, since each PCR experiment performed in tubes (Eppendorf tubes) with a final volume of 100 μL allows up to 8 μL of sample to be used. For example, if the number of equivalent cells per microliter (N) is 6500 and a sensitivity (S) of $10^{-5}$ is desired, it would be necessary to use $1/(6500\times10^{-5})=15.4$ μL of test sample in the PCR, and because up to 8 μL of sample can be used per PCR experiment, two PCR experiments would be needed.

iv) PCR of the Samples

PCR was performed using Platinum® Taq DNA Polymerase High Fidelity (Life Technologies) and the primers used were those described in BIOMED-2 protocol for IgH (CDR1/CDR2/CDR3 and DH) and IgK (KVJ-JK, KVJ-KDEL, INTR-KDEL), because these fragments cover more than 90% of cases (Van Dongen Leukemia 2003). The primers used to amplify said fragments of the IgH gene are shown in Table 1, while the primers used to amplify said fragments of the IgK gene are shown in Table 2.

TABLE 1

Primers for amplification of fragments of IgH

| Family primers | Tube | Sequence identifier | Primer name | Sequence | Sense |
|---|---|---|---|---|---|
| $V_H$ | Tube A (CDR1) | SEQ ID NO: 1 | $V_H$1-FR1 | GGCCTCAGTGAAGGTCTCCTGCAAG | Forward |
| | | SEQ ID NO: 2 | $V_H$2-FR1 | GTCTGGTCCTACGCTGGTGAAACCC | |
| | | SEQ ID NO: 3 | $V_H$3-FR1 | CTGGGGGGTCCCTGAGACTCTCCTG | |
| | | SEQ ID NO: 4 | $V_H$4-FR1 | CTTCGGAGACCCTGTCCCTCACCTG | |
| | | SEQ ID NO: 5 | $V_H$5-FR1 | CGGGGAGTCTCTGAAGATCTCCTGT | |
| | | SEQ ID NO: 6 | $V_H$6-FR1 | TCGCAGACCCTCTCACTCACCTGTG | |
| | Tube B (CDR2) | SEQ ID NO: 7 | $V_H$1-FR2 | CTGGGTGCGACAGGCCCCTGGACAA | |
| | | SEQ ID NO: 8 | $V_H$2-FR2 | TGGATCCGTCAGCCCCCAGGGAAGG | |
| | | SEQ ID NO: 9 | $V_H$3-FR2 | GGTCCGCCAGGCTCCAGGGAA | |
| | | SEQ ID NO: 10 | $V_H$4-FR2 | TGGATCCGCCAGCCCCCAGGGAAGG | |
| | | SEQ ID NO: 11 | $V_H$5-FR2 | GGGTGCGCCAGATGCCCGGGAAAGG | |
| | | SEQ ID NO: 12 | $V_H$6-FR2 | TGGATCAGGCAGTCCCCATCGAGAG | |
| | | SEQ ID NO: 13 | $V_H$7-FR2 | TTGGGTGCGACAGGCCCCTGGACAA | |
| | Tube C (CDR3) | SEQ ID NO: 14 | $V_H$1-FR3 | TGGAGCTGAGCAGCCTGAGATCTGA | |
| | | SEQ ID NO: 15 | $V_H$2-FR3 | CAATGACCAACATGGACCCTGTGGA | |
| | | SEQ ID NO: 16 | $V_H$3-FR3 | TCTGCAAATGAACAGCCTGAGAGCC | |
| | | SEQ ID NO: 17 | $V_H$4-FR3 | GAGCTCTGTGACCGCCGCGGACACG | |
| | | SEQ ID NO: 18 | $V_H$5-FR3 | CAGCACCGCCTACCTGCAGTGGAGC | |
| | | SEQ ID NO: 19 | $V_H$6-FR3 | GTTCTCCCTGCAGCTGAACTCTGTG | |
| | | SEQ ID NO: 20 | $V_H$7-FR3 | CAGCACGGCATATCTGCAGATCAG | |
| $D_H$ | Tube D | SEQ ID NO: 21 | $D_H$1 | GGCGGAATGTGTGCAGGC | |
| | | SEQ ID NO: 22 | $D_H$2 | GCACTGGGCTCAGAGTCCTCT | |
| | | SEQ ID NO: 23 | $D_H$3 | GTGGCCCTGGGAATATAAAA | |
| | | SEQ ID NO: 24 | $D_H$4 | AGATCCCCAGGACGCAGCA | |
| | | SEQ ID NO: 25 | $D_H$5 | CAGGGGGACACTGTGCATGT | |
| | | SEQ ID NO: 26 | $D_H$6 | TGACCCCAGCAAGGGAAGG | |
| | Tube E | SEQ ID NO: 27 | $D_H$7 | CACAGGCCCCCTACCAGC | |
| $J_H$ | Tubes A-E | SEQ ID NO: 28 | JH57 | CTTACCTGAGGAGACGGTGACC | Reverse |

TABLE 2

Primers for amplification of fragments of IgK

| Family primers | Tube | Sequence identifier | Primer name | Sequence | Sense |
|---|---|---|---|---|---|
| $V_K$ | Tube F, G | SEQ ID NO: 29 | $V_K1f/6$ | TCAAGGTTCAGCGGCAGTGGATCTG | Forward |
| | | SEQ ID NO: 30 | $V_K2f$ | GGCCTCCATCTCCTGCAGGTCTAGTC | |
| | | SEQ ID NO: 31 | $V_K3f$ | CCCAGGCTCCTCATCTATGATGCATCC | |
| | | SEQ ID NO: 32 | $V_K4$ | CAACTGCAAGTCCAGCCAGAGTGTTTT | |
| | | SEQ ID NO: 33 | $V_K5$ | CCTGCAAAGCCAGCCAAGACATTGAT | |
| | | SEQ ID NO: 34 | $V_K6$ | GACCGATTTCACCCTCACAATTAATCC | |
| $J_K$ | Tube F | SEQ ID NO: 35 | $J_K1-4$ | CTTACGTTTGATCTCCACCTTGGTCCC | Reverse |
| | | SEQ ID NO: 36 | $J_K5$ | CTTACGTTTAATCTCCAGTCGTGTCCC | |
| KDEL | Tube G, H | SEQ ID NO: 37 | KDEL | CCTCAGAGGTCAGAGCAGGTTGTCCTA | |
| $J_K$-$C_K$ Intron | Tube H | SEQ ID NO: 38 | INTR | CGTGGCACCGCGAGCTGTAGAC | Forward |

Amplification of the test simple was performed using the number of PCR experiments (i.e. PCR tubes) which were calculated as necessary based on the volume of the test sample (V, μL), the number of equivalent cells per microliter (N) of said sample, the sensitivity (S) which it was desired to reach and the final PCR tube volume. Accordingly, the amounts of each component (per PCR tube) for each PCR reaction mix for the test sample were as follows:

a) PCR CDR1/CDR2/CDR3
   84 μL Platinum HIFI master mix
   4 μL Primers CDR1/CDR2/CDR3 mix (Tubes A, B, C)
   4 μL Primer JH57
   8 μL gDNA
b) PCR KVJ
   80 μL Platinum HIFI master mix
   4 μL Primers KVmix (Tube F)
   4 μL Primer KJ5
   4 μL Primer KJ1-4
   8 μL gDNA
c) PCR DH
   84 μL Platinum HIFI master mix
   4 μL Primers DH 1-6 (Tube D) or DH7 (Tube E)
   4 μL JH57
   8 μL gDNA
d) PCR KDEL
   80 μL Platinum HIFI master mix
   4 μL Primers KVmix (Tube G)
   4 μL INTR (Tube H)
   4 μL KDEL
   8 μL gDNA The diagnostic sample is amplified with the same reactions but using 1 μL of DNA (1 μL of DNA=approximately 20 ng gDNA, i.e. [DNA]=20 μg/mL) because it is not necessary to reach a given sensitivity in the diagnostic sample.

v) Preparation of Amplicon Libraries without Fragmentation

The amplified products of both samples (diagnosis and follow-up) were used to prepare respective amplicon libraries without fragmentation using Ion Plus Fragment Library kit and Agencourt Ampure XP (Thermo-Fisher). It was found possible to use half of the volumes of all reactants using the Ion Plus Fragment Library kit. The final library concentration was determined using qPCR in the GeneRead Library Quant kit (Qiagen). The libraries were generated using specific barcodes for each sample.

vi) Massive Parallel Sequencing

The main clone or clones were identified in the diagnostic sample via massive parallel sequencing of the product of the amplification of CDR1, CDR2, CD3, KVJ, DH and KDEL. Clonal samples with fragments greater than 250 bp were sequenced on the PGM platform (Ion Torrent Personal Genome Machine™ platform) using OneTouch™ Ion v2 Kit Template 400 DL, 400 Ion PGM™ Sequencing Kit v2 and Ion Chip 318™ Kit according to the manufacturers instructions (Thermo-Fisher). Fragments less than 250 bp (mainly from samples with the rearrangements KVJ and KDEL) were sequenced using the PROTON platform: Ion Proton™|emulsion OT2 Template Kit and sequencing Ion Proton™|Sequencing Kit (Thermo-Fisher). All reagents were purchased from Lifetech using their protocols with slight modifications: PGM platform technology sequences fragments up to 250 bp, but it is possible to sequence fragments up to 400 bp with another commercial kit of Lifetech using different chemistry.

vii) Bioinformatic Analysis

After sequencing, FASTQ files of the two samples were obtained from the Torrent Browser according to the corresponding Barcode. Each FASTQ file comprises a list of characters reading from left to right which represents the nucleotide sequence of the DNA comprised in said sample, and additionally comprises the quality score corresponding to each character of said list of characters.

The quantification of each clonotypic sequence or sequences in the diagnostic sample was determined using mathematical and computer methods (IT tools), namely using the FrequencyRank.sh Bourne shell script (frequency_rank.sh) to sort sequences in descending frequency order. Once the clonal sequences which are the same in the diagnostic sample as in the follow-up sample were determined, a .dna file was generated comprising each of said clonal sequences as a list of characters reading from left to right and having a total number of characters The number of clonal sequences (first lists of characters) identified in the diagnostic sample which were considered the same as the argument sequence (second lists of characters was counted using the SeqSearchFastq.java program with the -trim option and a match ratio (degree of similarity) of 0.99, to give a value, $L_c$. $L_t$ was determined from the total number of first lists of characters.

As the method of the invention involves a mixture of alignment and comparison, comparison was made only between the first and the last matching position and the -trim option instructs the process to act in this way, limiting the comparison from the first and last matching positions instead of first and last positions (regardless of matching) in the sample sequence. The output, $L_c$, from the SeqSearchFastq.java program is subsequently used, together with the values for Li, k and D, to calculate the MRD.

Example 1. Quantification of MRD in Multiple Myeloma Using Massively Parallel Sequencing of Genes of Immunoglobulins The following presents a method for quantification of tumor clonotypic sequences within the polyclonal background rearrangements of genes of immunoglobulins (Ig) via massively parallel sequencing (MPS). The detection of clonal rearrangement in B and T cell neoplasms allows the evolution of these pathologies to be monitored. To quantify these rearrangements in B cells, primers disclosed in Tables 1 and 2 for CDR3, VDJ, IgH, IgK, KVJ, KDEL, and IgL were used, because these fragments cover more than 90% of cases (Van Dongen, Leukemia 2003). The selection of these particular rearrangements is due to the design of primers which only amplify short (less than 200 bp) sequences; allowing to sequence these fragments in the PROTON platform, capable of 10 Gb.

Patients negative for VDJ, IgH, GDR3, KVJ, KDEL diagnoses may be sequenced with the rest of the BIOMED primers like IgH, VDJ, CDRI and IgL DJ. As the size of these fragments is between 300 and 400 base pairs (bp), it is necessary to use the PGM platform with reactive kit for 400 bp. The ability of PGM is near 1 Gbase, whereby ability refers to the number of bases that can be read in a PGM run.

Results:

Serial dilutions of clonotypic experimental samples indicated a sensitivity of $10^{-5}$ for 150,000 cells. The correlation of all samples with the data from flow cytometry achieved an R=0.59 (Pearson=0.765, p<0.0001) and R=0.51 (Pearson=0.716, p<0.0001) for follow-up samples. The average of the readings of the BIOMED primers was similar to the frequencies of the different fragments described in multiple myeloma. The reproducibility of the technique was over 90%. Of the 24 follow-ups analyzed, two were positive by massively parallel sequencing and negative by flow cytometry and one was negative by massively parallel sequencing and positive by flow cytometry. In the PGM platform, parallel analysis of 12 follow-ups was achieved in a week with a coverage of 500.000× and at an approximate price of 100 Euros/sample.

Figure 5:
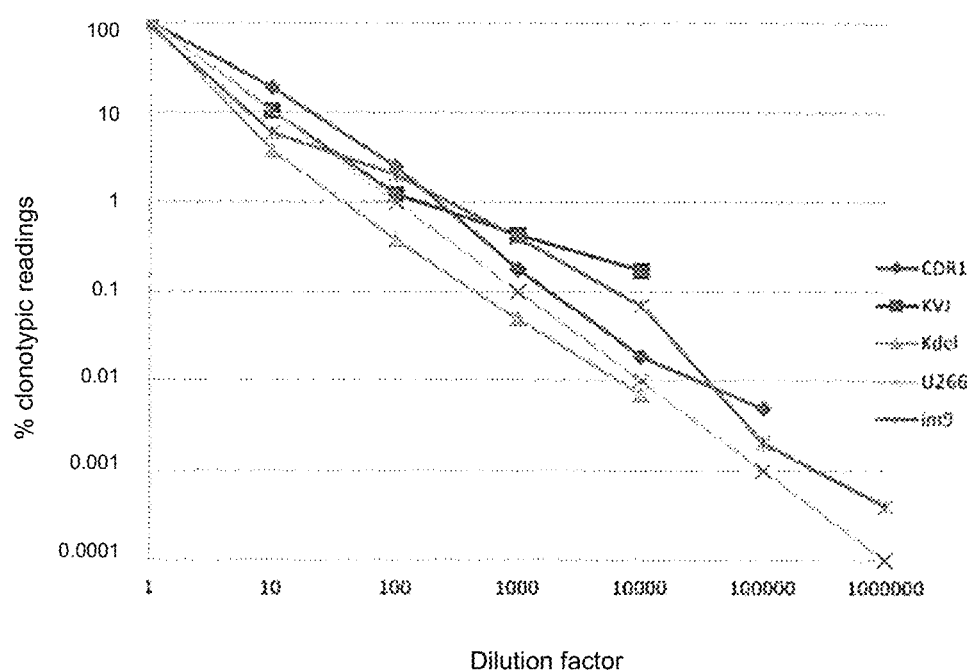
FIG. 5. Sensitivity of the method of the present invention in the characterization of gene rearrangements of immunoglobulins in samples from multiple myeloma patients. The percentage of clonotypic readings is measured by serial dilution of clonal rearrangements on a polyclonal background obtained from healthy patients or from non-B cell lines, wherein the sensitivity depends on the number of variants found in a clonotypic reading.

In FIG. 5, the sensitivity achieved in serial dilutions of multiple myeloma clonal rearrangements on a polyclonal background obtained from healthy patients or from non B cell lines, is shown. The sensitivity in the characterization of gene rearrangements of immunoglobulins is determined by the amount of input DNA, or equivalent cell number. The sensitivity of this technique depends on the number of variants found in a clonal reading and shows that the method of the invention exhibits extremely high sensitivity in detection of MRD.

Figure 6:
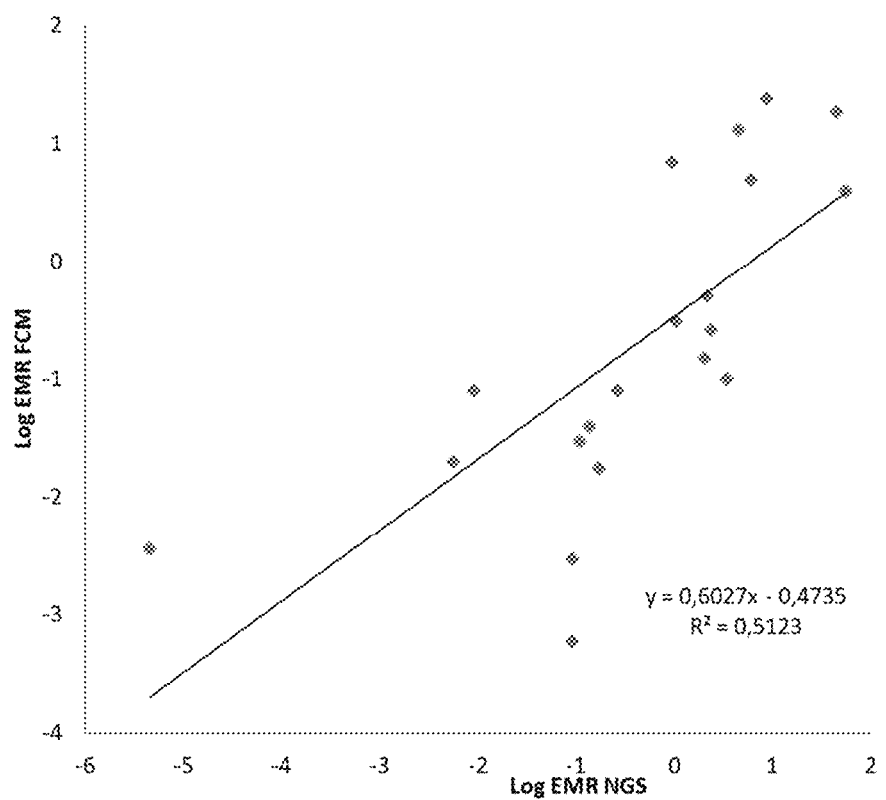
FIG. 6. Correlation ($R^2$=0.51) between MRD data measured with flow cytometry (Log EMR FCM, y axis) and massive parallel sequencing (Log EMR NGS, x axis) for main rearrangements in follow-up samples of patients diagnosed with and treated for multiple myeloma.

FIG. 6 shows the main clonal rearrangement correlation in samples from patients who have been treated for multiple myeloma (follow-up samples) between MRD data measured with flow cytometry (y axis) and massive parallel sequencing according to the present invention (x axis). MRD quantification in multiple myeloma performed by flow cytometry refers to the total cell number, with equivalent equation to that of this invention. The correlation between the two techniques is high, with $R^2$=0.51.

Conclusions:

Deep-sequencing of the rearrangements of Ig genes by Ion Torrent technology is an effective technique to define and quantify the pathological clones in multiple myeloma. This technique is a methodical and economically viable alternative to flow cytometry and other methods of monitoring MRD.

Thus, quantitation with high sensitivity of the specific sequences belonging to the pathological clones that define the condition allows the monitoring of the evolution and cellular response to specific treatments, the definition of new disease foci, and the monitoring of minimal residual disease in patients with defined genetic alterations.

Example 2. Quantification of SNV, MNV and Indels

Figure 7:
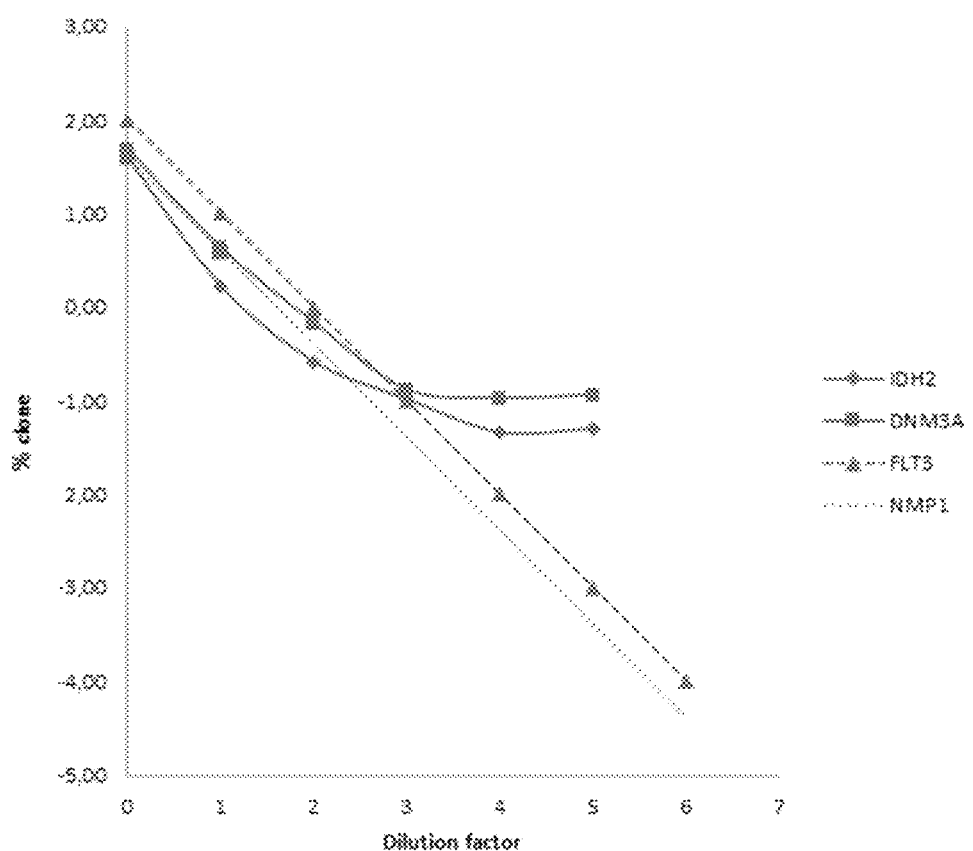
FIG. 7. Quantification of sensitivity of the method of the present invention in the characterization of point mutations (DNM3A, IDH2, FLT3 and NMP1) in acute myeloid leukemia (AML) patients. The percentage of clonotypic readings is measured in serial dilutions of AML mutated genes.

The method described in the foregoing is applicable to the detection of any type of mutation, given some limitations, as follows. The average error based on massive sequencing platforms is 0.5% or, in other words, one erroneous reading in 200 for each position in the genome. The probability that an error happens reading the variant sought is 0.5%/4 bases, or about 0.1%. This theoretical limitation has been verified experimentally for point mutations (SNV: DNM3A and IDH2) in cases of AML (acute myeloid leukemia, FIG. 7), wherein this error is 0.1% for each position. In those mutations that include more than two positions for reading, such as a multiple mutation (MNV) or an indel, the error will be (0.1×n) %, where n is the number of clonal variants present in the reading.

Example 3. Quantification of Long Insertions and Translocations

In this case the sensitivity limit is not reached due to the fact that there is no background against which to compare readings, because primers amplify only those DNA fragments that have a translocation or inversion. To alleviate this problem, a control DNA was used, this being one of the genes involved in the translocation, in its wild-type form. Thus the ratio of clonotypic sequences/total sequences takes into account the number of readings of both.

Examples Part II

Materials and Methods viii) Samples

Bone marrow (BM) samples were obtained from 73 multiple myeloma patients from whom DNA was available for testing (Bioproject PRJNA360043). Patients were enrolled in the phase 2 trial for newly diagnosed elderly MM patients PETHEMA/GEM2010MAS65 study (www dot clinicaltrials dot gov as #NCT01237249); patients were randomized to receive 9 cycles of bortezomib/melphalan/prednisone (VMP) followed by 9 cycles of lenalidomide/dexamethasone (Rd; sequential arm, n=38) vs 18 alternating cycles of VMP/Rd (alternating arm, n=35) (Blood 2016; 127: 420-425). Nighty-five percent (n=69) of the patients experienced a CR according to the International Myeloma Working Group (IMWG) (Lancet Oncol. 2016; 17:e328-e346). Median follow-up of the series was 3 years.

ix) DNA Extraction, DNA Quantification and Calculation of Concentration of DNA

Were performed as per Examples part I, above. Note that this method quantifies MRD in multiple myeloma patients from 1 μg of DNA.

x) PCR of the Samples

PCR was performed as per Examples part I, above. However, the primers used were standardized primers developed by the Biomed-2 concerted action to amplify all IgH or IgK sequences in a patient sample (Leukemia 2003; 17: 2257-2317), or were primers selected from the following Tables 3 and 4. The primers used to amplify said fragments of the IgH gene are shown in Table 3, while the primers used to amplify said fragments of the IgK gene are shown in Table 4.

TABLE 3

Primers for amplification of fragments of IgH

| Family primers | Sequence identifier | Primer name | Sequence | Sense |
|---|---|---|---|---|
| $V_H$ | SEQ ID NO: 39 | $2V_H1$-1 | CAAGGGCTTGAGTGGATGGGA | Forward |
| | SEQ ID NO: 40 | $2V_H1$-2 | CAACGCCTTGAGTGGATAGGATGG | |
| | SEQ ID NO: 41 | $2V_H1$-3 | GACAAGGGCTTGAAAGGATGAGATGG | |
| | SEQ ID NO: 42 | $2V_H2$-1 | GCCCTGGAGTGGCTTGC | |
| | SEQ ID NO: 43 | $2V_H2$-2 | GAAGGCCCTGGAGTGGATTGC | |
| | SEQ ID NO: 44 | $2V_H3$-1 | GGAAGGGGCTGGAGTGGG | |
| | SEQ ID NO: 45 | $2V_H3$-9 | GGGAAGGGTCTGGAGTGGG | |
| | SEQ ID NO: 46 | $2V_H3$-11 | GCTACAGGAAAAGGTCTGGAGTGGG | |
| | SEQ ID NO: 47 | $2V_H3$-12 | GGAAGGGCCTGGAGTGGG | |
| | SEQ ID NO: 48 | $2V_H3$-13 | GGAGAAGGGGCAGGAGTGGG | |
| | SEQ ID NO: 49 | $2V_H3$-14 | GGCAAGGGGCTAGAGTGGG | |
| | SEQ ID NO: 50 | $2V_H3$-16 | GGAAGGGGCTGGTGTGGG | |
| | SEQ ID NO: 51 | $2V_H3$-17 | GGGAAGGGGCTGGAATGGG | |
| | SEQ ID NO: 52 | $2V_H3$-18 | GCTACAGGAAAAGGTCTGGAATGGG | |
| | SEQ ID NO: 53 | $2V_H3$-19 | AGGGAATGGGCTGGAGTTGG | |
| | SEQ ID NO: 54 | $2V_H3$-21 | AGGGAAGGGGCTGGAGTGAG | |
| | SEQ ID NO: 55 | $2V_H3$-22 | GGAAGGGTCCGGAGTGGG | |
| | SEQ ID NO: 56 | $2V_H3$-23 | GCTCCAAGAAAGGGTTTGTAGTGGG | |
| | SEQ ID NO: 57 | $2V_H3$-24 | GGAAGGGGCTGGAGGGAG | |
| | SEQ ID NO: 58 | $2V_H3$-25 | GCTCCAGGGAAGGGACTGGAATATG | |
| | SEQ ID NO: 59 | $2V_H4$-1 | GGAAGGGACTGGAGTGGATTGG | |
| | SEQ ID NO: 60 | $2V_H4$-2 | GAAGGGCCTGGAGTGGATTGG | |
| | SEQ ID NO: 61 | $2V_H4$-3 | GAAGGGGCTGGAGTGGATTGG | |
| | SEQ ID NO: 62 | $2V_H5$-1 | CCTGGAGTGGATGGGGAGG | |
| | SEQ ID NO: 63 | $2V_H5$-2 | GCCTGGAGTGGATGGGGATC | |
| | SEQ ID NO: 64 | $2V_H5$-3 | GAAAGAACTGGAGTGGATGGGGAG | |
| | SEQ ID NO: 65 | $2V_H6$-4 | AGGCAGTCCCCATCGAGAGG | |
| | SEQ ID NO: 66 | $2V_H7$-5 | AGGGCTTTGAGTGGATGTGATGG | |
| | SEQ ID NO: 67 | $2V_H7$-6 | AGGGCTTGAGTGGATGGGATGG | |
| | SEQ ID NO: 68 | $3V_H1$-12 | ACGAGCACAGCCTACATGGAG | |
| | SEQ ID NO: 69 | $3V_H1$-19 | CCACAACCACAGCCTACACAGAC | |
| | SEQ ID NO: 70 | $3V_H1$-20 | CCACGAGCACAGTCTACATGGAG | |
| | SEQ ID NO: 71 | $3V_H1$-21 | TCCCTGAGGACAGCCTACATAGAG | |
| | SEQ ID NO: 72 | $3V_H2$-7 | CTCACCATCTCCAAGGACACCTCC | |
| | SEQ ID NO: 73 | $3V_H2$-8 | CTCACCATCACCAAGGACACCTCC | |
| | SEQ ID NO: 74 | $3V_H2$-9 | CTCATTATCTCCAAGGACACCTCC | |
| | SEQ ID NO: 75 | $3V_H2$-10 | CTCACCATTACCAAGGACACCTCC | |
| | SEQ ID NO: 76 | $3V_H3$-26 | CGCTGTATCTGCAAATGAACAGCCTG | |
| | SEQ ID NO: 77 | $3V_H3$-27 | CTCACTGTATCTGCAAATGAACAGCCTG | |
| | SEQ ID NO: 78 | $3V_H3$-28 | CTGTATCAGCAAATGAACAGCCTG | |
| | SEQ ID NO: 79 | $3V_H3$-30 | CGCTGCATCTTCAAATGAACAGCCTG | |
| | SEQ ID NO: 80 | $3V_H3$-31 | CACGCTGTATCTTCAAATGAACAGCCTG | |
| | SEQ ID NO: 81 | $3V_H3$-32 | CCTCTATCTGCAAGTGAACAGCCTG | |
| | SEQ ID NO: 82 | $3V_H3$-33 | GCTGTATCTGCAAATGAGCAGCCTG | |
| | SEQ ID NO: 83 | $3V_H3$-34 | CGCTGTATCTGCAAATGATCAGCCTG | |
| | SEQ ID NO: 84 | $3V_H3$-35 | CATCACCTATCTGCAAATGAAGAGCCTG | |
| | SEQ ID NO: 85 | $3V_H3$-36 | ACCCTGTATCTGCAAACGAATAGCCTG | |
| | SEQ ID NO: 86 | $3V_H3$-37 | GCTGTATCTTCAAATGGGCAGCCTG | |
| | SEQ ID NO: 87 | $3V_H3$-38 | CAAGAACTCACTGTATTTGCAAATGAACAGTCTG | |
| | SEQ ID NO: 88 | $3V_H3$-39 | CCAAGAACTCACTGTATTTGCTAATGAACAGTCTG | |
| | SEQ ID NO: 89 | $3V_H3$-40 | CACCGTATCTCCAAACGAACAGTCTG | |
| | SEQ ID NO: 90 | $3V_H3$-41 | CACGCTGTATGTTCAAATGAGCAGTCTG | |
| | SEQ ID NO: 91 | $3V_H3$-42 | CCCTGTATCTGCAAAAGAACAGACGG | |
| | SEQ ID NO: 92 | $3V_H3$-43 | TAAGAACTCTCTGTATCTGCAAATGAACAGTCAG | |
| | SEQ ID NO: 93 | $3V_H3$-44 | TAAGAACTCTCTGTATCTGCAAATGAACACTCAG | |
| | SEQ ID NO: 94 | $3V_H3$-45 | GAACACGCTGTATCTTCAAATGAACAACCTG | |
| | SEQ ID NO: 95 | $3V_H4$-17 | ACCTACTACAACCCGTCCCTCAAG | |
| | SEQ ID NO: 96 | $3V_H4$-19 | ACCAACTACAACCCCTCCCTCAAG | |
| | SEQ ID NO: 97 | $3V_H4$-21 | ACCAACAACAACCCGTCCCTCAAG | |
| | SEQ ID NO: 98 | $3V_H4$-24 | CCCAACTACAACCCATCCCTCAAG | |
| | SEQ ID NO: 99 | $3V_H5$-1 | GCAGTGGAGCAGCCTGAAGG | |
| | SEQ ID NO: 100 | $3V_H6$-5 | CAGACACATCCAAGAACCAGTTCTCCC | |
| | SEQ ID NO: 101 | $3V_H7$-8 | GTTTGTCTTCTCCTTGGACACCTCTG | |
| | SEQ ID NO: 102 | $3V_H7$-9 | GTTTGTCTTCTCCATGGACACGTCTG | |
| | SEQ ID NO: 103 | $3V_H7$-10 | GTTTGTCTTCTCCTTGGACACGTCTG | |

TABLE 3-continued

Primers for amplification of fragments of IgH

| Family primers | Sequence identifier | Primer name | Sequence | Sense |
|---|---|---|---|---|
| $J_H$ | SEQ ID NO: 104 | JH2 | ACCTGAGGAGACGGTGACC | Reverse |
| | SEQ ID NO: 105 | JH3 | CCTGAAGAGACGGTGACCATTG | |
| | SEQ ID NO: 106 | JH4 | ACCTGAGGAGACAGTGACCAG | |

TABLE 4

Primers for amplification of fragments of IgK

| Family primers | Sequence identifier | Primer name | Sequence | Sense |
|---|---|---|---|---|
| $V_K$ | SEQ ID NO: 107 | $V_K$1-1 | CCCATCAAGGTTCAGCGGCAG | Forward |
| | SEQ ID NO: 108 | $V_K$1-2 | CCCATCAAAGTTCAGCGGCAG | |
| | SEQ ID NO: 109 | $V_K$1-3 | GGTCCCATCAAGGTTCAGTGGAAG | |
| | SEQ ID NO: 110 | $V_K$1-4 | CCCATCTCGGTTCAGTGGCAG | |
| | SEQ ID NO: 111 | $V_K$1-5 | GTCCCATCAAGGTTCAGTGGCAG | |
| | SEQ ID NO: 112 | $V_K$1-6 | CCCATCCAGGTTCAGTGGCAG | |
| | SEQ ID NO: 113 | $V_K$1-7 | GATTCCCTCTCGGTTCAGTGACAG | |
| | SEQ ID NO: 114 | $V_K$1-8 | CCCTCTCAGTTCAGTGACAG | |
| | SEQ ID NO: 115 | $V_K$1-9 | CCCACTCGGTTCAGTGACAG | |
| | SEQ ID NO: 116 | $V_K$1-10 | CTCATCGAGGTTCAGTGGCAG | |
| | SEQ ID NO: 117 | $V_K$2-1 | AGTGGCAGCGGGTCAGG | |
| | SEQ ID NO: 118 | $V_K$2-2 | TTCAGTGGCAGTGGGTCAGG | |
| | SEQ ID NO: 119 | $V_K$2-3 | GGTTTAGTGGCAGTGGGTCAGG | |
| | SEQ ID NO: 120 | $V_K$2-4 | AGCGGCAGTGGGTCAGG | |
| | SEQ ID NO: 121 | $V_K$2-5 | TTCAGTGGCAGTGGATCAGGC | |
| | SEQ ID NO: 122 | $V_K$2-6 | AGTGGCAGTGGGGCAGG | |
| | SEQ ID NO: 123 | $V_K$2-7 | AGTGGCAGTGGGTCGGG | |
| | SEQ ID NO: 124 | $V_K$2-8 | TTCAGTGGCAGCAGGTCAGG | |
| | SEQ ID NO: 125 | $V_K$3-1 | CCAGGTTCAGTGGCAGTGGG | |
| | SEQ ID NO: 126 | $V_K$3-2 | GACAGGTTCAGTGGCAGTGGG | |
| | SEQ ID NO: 127 | $V_K$3-3 | GCAAGGTTCAGTGGCAGTGGG | |
| | SEQ ID NO: 128 | $V_K$3-4 | GCCAGGTTCAGTGGTAGTGGG | |
| | SEQ ID NO: 129 | $V_K$4-1 | GTCCCTGACCGATTCAGTGGC | |
| | SEQ ID NO: 130 | $V_K$5-1 | TTCAGTGGCAGCGGGTATGG | |
| | SEQ ID NO: 131 | $V_K$6-1 | GTTCAGTGGCAGTGGATCTGGG | |
| | SEQ ID NO: 132 | $V_K$7-1 | AGGTTCAGCGGCAGTGGG | |
| $J_K$ | SEQ ID NO: 133 | $J_K$-1 | ATTTCCACCTTGGTCCCTTGGC | Reverse |
| | SEQ ID NO: 134 | $J_K$-2 | ATCTCCAGCTTGGTCCCCTG | |
| | SEQ ID NO: 135 | $J_K$-3 | ATATCCACTTTGGTCCCAGGGC | |
| | SEQ ID NO: 136 | $J_K$-4 | CTCCACCTTGGTCCCTCCG | |
| | SEQ ID NO: 137 | $J_K$-5 | ATCTCCAGTCGTGTCCCTTGGC | | xi) Preparation of Libraries and Massive Parallel Sequencing

The amplified products of samples (diagnosis and subsequent cycles of follow-up) were used to prepare libraries by ligation of specific adaptor oligos and sequenced either on an Ion S5 (ThermoFisher Scientific, Palo Alto, Calif., USA) or on a MiSeq sequencer (Illumina, San Diego, Calif., USA)

xii) Bioinformatic Analysis

The sequencing data were analyzed with a set of specific mathematical and bioinformatics tools to identify and quantitate the clone-specific sequence (clonotype) present on each sample (code patent pending). A clonotype was identified when at least 400 identical sequencing reads were obtained, or was present at a frequency of 41%.

Statistical analyses were performed with the SPSS program version 21.0 (IBM, Armonk, N.Y., USA). Linear regression was used to compare different dilutions of the DNA samples. The Spearman correlation coefficient was used to compare MFC data with NGS data. Overall survival (OS) and progression-free survival (PFS) were estimated by Kaplan-Meier survival analysis and statistical differences assessed via log-rank and Wilcoxon analyses.

Example 4. Analytical and Clinical Validation of a Deep-Sequencing Method for Minimal Residual Disease Monitoring in a Phase II Trial for Multiple Myeloma The following describes and analytically validates a simplified in-house deep-sequencing method to identify and quantify MRD in MM patients from 1 μg of DNA.

Figure 8:
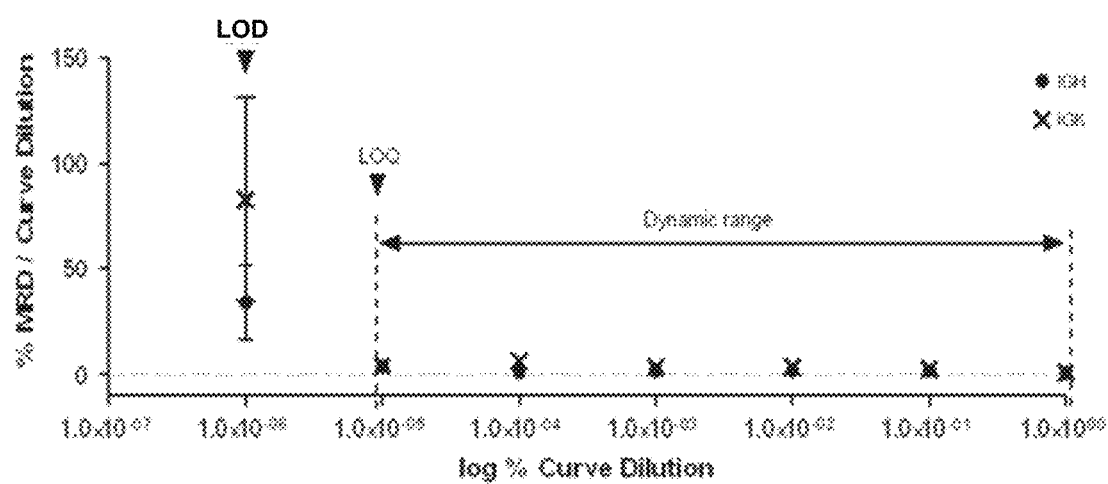
FIG. 8. Performance characteristics of the NGS assay. Plot of the dynamic range, limit of quantification (LOQ) and limit of detection (LOD) of the method from a 10-fold dilution curve. The vertical axis represents the ratio of MRD values to curve dilution and the horizontal axis represents the logarithm value for curve dilution. $R^2$=0.98 and 0.96 for IgH and IgK genes, respectively, P<0.0001. The threshold for negative values was $10^{-5}$.

Results:

In this deep sequencing approach, a clonotype was detected in 97% (71 out of 73) of multiple myeloma patients, indicating a specificity higher than the clinical specificity reported in the previously described NGS assay for IG quantification (91%) (Blood 2014; 123: 3073-3079). Clonotypes were not detected in normal tonsil and bone marrow samples, indicating the high specificity of the assay. This method also presents a very good analytical sensitivity of at least 10-5, as determined from a 10-fold dilution curve of commercial control monoclonal and polyclonal DNAs (FIG. 8). With the same primer combinations, the analytical sensitivity of Biomed-2 amplification to detect a clonal population was $10^{-2}$ for IgH and IgK (Leukemia 2003; 17: 2257-2317) consequently, applying deep-sequencing technologies to the Biomed-2 design highly improves the sensitivity of clonal identification. In addition, the method also shows high reproducibility between runs and different NGS platforms (99.2%, 91 samples tested in duplicate in different sequencing runs) and is very precise for samples with MRD-negative values (median CV 8.1%, range 3.9-39).

As demonstrated in several trials, a prolonged therapy is an effective approach to improve survival in elderly patients. This was the basis for the 18 cycles explored in the GEM10mas65 clinical trial (VMP+Ld combination), which yielded excellent clinical results (Blood 2016; 127:420-425; Clin. Lymphoma Myeloma Leuk. 2013; 13(Suppl 2): S349-S354). When the molecular response in these multiple myeloma patients was analysed it was found that the proportion of patients achieving an MRD-negative status is significantly higher after 18 cycles of treatment (27% (n=19) vs 11.5% (n=8) after 18 and 9 cycles, respectively, P=0.04), confirming that a prolonged treatment improves the rate of molecular responses. The patients achieving an MRD-negative status were not subjected to further treatment. However, the remaining patients who failed to achieve an MRD-negative status (i.e. which still were determined to have MRD) were subjected to further treatment for multiple myeloma using a further 18 cycles of VMP+Ld combined therapy, following which MRD status was again determined.

Figure 9:
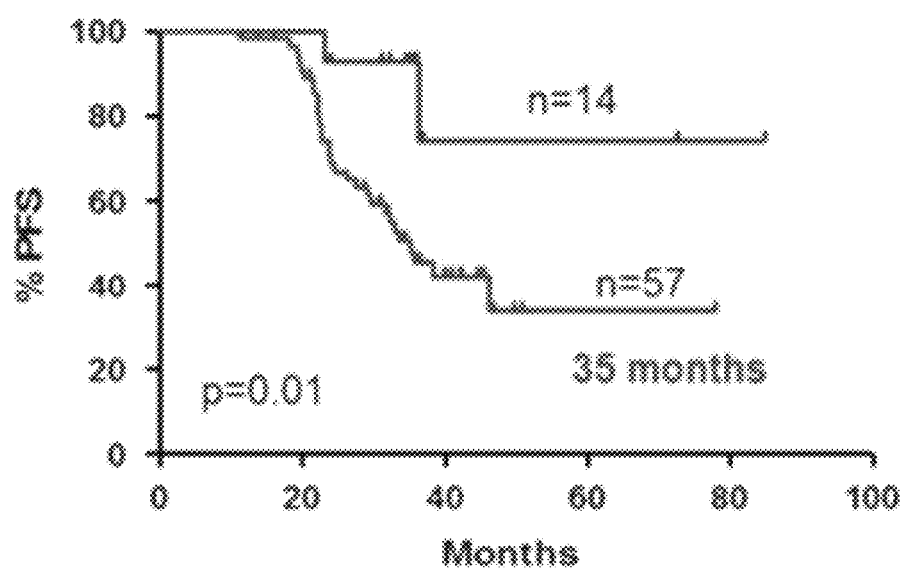
FIG. 9. Performance characteristics of the NGS assay. Progression-free survival (PFS) plot according to MRD levels. MRD-negative values (n=14) and MRD-positive values (n=57). The threshold for negative values was $10^{-5}$.
Figure 10:
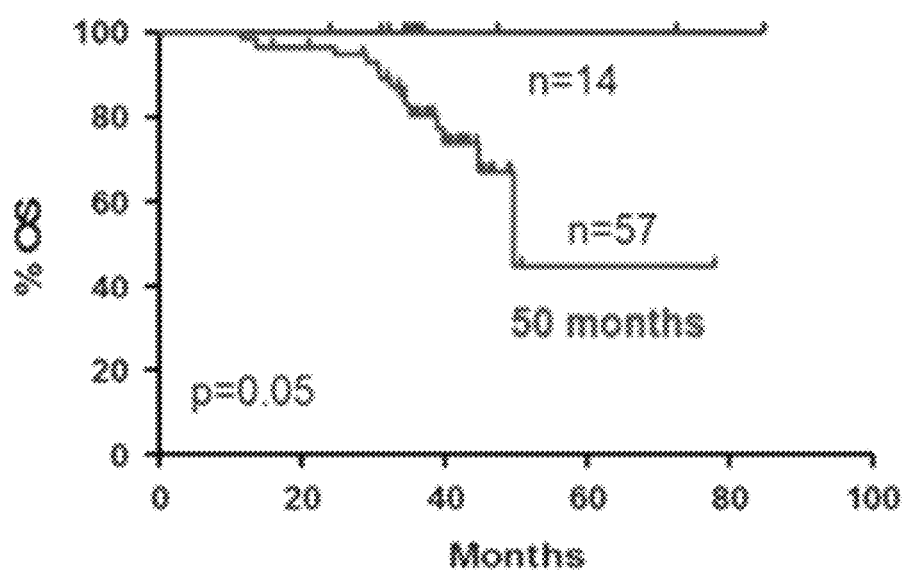
FIG. 10. Performance characteristics of the NGS assay. Overall survival (OS) plot according to MRD levels. MRD-negative values (n=14) and MRD-positive values (n=57). The threshold for negative values was $10^{-5}$.

Similar to the data obtained with other MRD methods (Blood 2014; 123: 3073-3079) the achievement of molecular responses measured by the NGS method of the present invention is able to predict 3-year survival in patients enrolled in the GEM10 clinical trial. Median PFS was 35 months vs not reached for patients with MRD-positive and -negative values, respectively (hazard ratio (HR)=2.76, 95% confidence interval (CI) 1.21-6.25, P=0.01; FIG. 9). Median OS was also prolonged in MRD-negative patients compared with MRD-positive patients, with 3-year OS rates of 100% and 45%, respectively (median OS of 50 months vs not reached respectively, HR=3.66, 95% CI 0.98-13.67, P=0.05; FIG. 10). Hence, achieving a molecular response as determined by the deep-sequencing method employed in the present invention results in improved PFS and OS.

The high efficacy of the treatment based on VMP and Rd in a sequential or alternating scheme (CR rates of 42% and 40%, and PFS of 74% and 80%, respectively) was demonstrated previously (Blood 2016; 127:420-425). In our present study, when the NGS method was employed to assess MRD negativity, more patients in the sequential treatment than in the alternating arm achieved a molecular response (36% (n=13) vs 20% (n=7), respectively). Nonetheless, no significant difference in OS between both treatment arms was observed. Taken together, the data show that patients could not only benefit from a prolonged treatment of 18 cycles but also suggest that 18 cycles of treatment in a sequential scheme can be associated with higher number of molecular responses and prolonged PFS.

Figure 11:
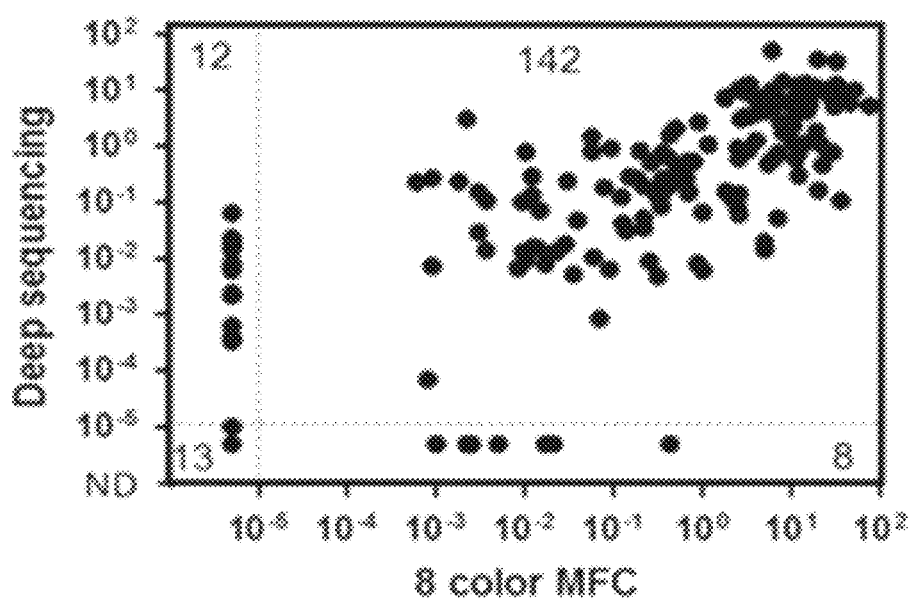
FIG. 11. Comparison between deep-sequencing (next generation sequencing, NGS) and multiparameter flow cytometry (8c-MFC) data. Scatter plot showing correlation of MRD values between deep sequencing and eight-color MFC. Numbers on upper left and lower right indicates samples with discordant results. Spearman correlation coefficient R=0.7917, P<0.0001.
Figure 12:
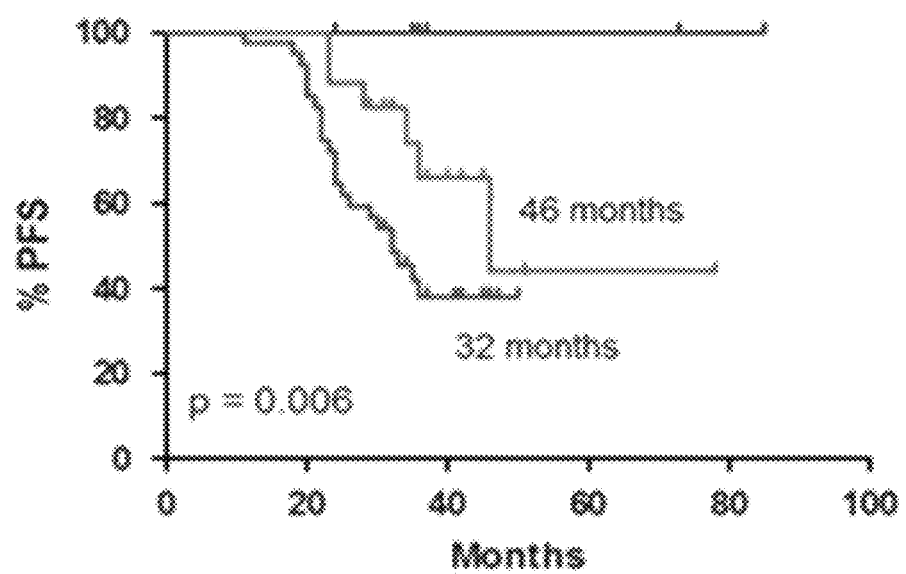
FIG. 12. Comparison between deep-sequencing (NGS) and multiparameter flow cytometry (8c-MFC) data. Progression-free survival (PFS) plot of patients grouped according to concordance of MRD levels between NGS and 8c-MFC. Data corresponds to patients with MRD-negative values (MRD<$10^{-5}$) by both methods (8c-MFC negative, NGS negative; line showing approx. 100% PFS); MRD-positive values (MRD>$10^{-5}$) by both methods (8c-MFC positive, NGS positive; line showing 50% OS at 50 months); and MRD with discrepant data between NGS and 8c-FCM (discordant 8c-MFC and NGS; line showing 50% PFS at 46 months).
Figure 13:
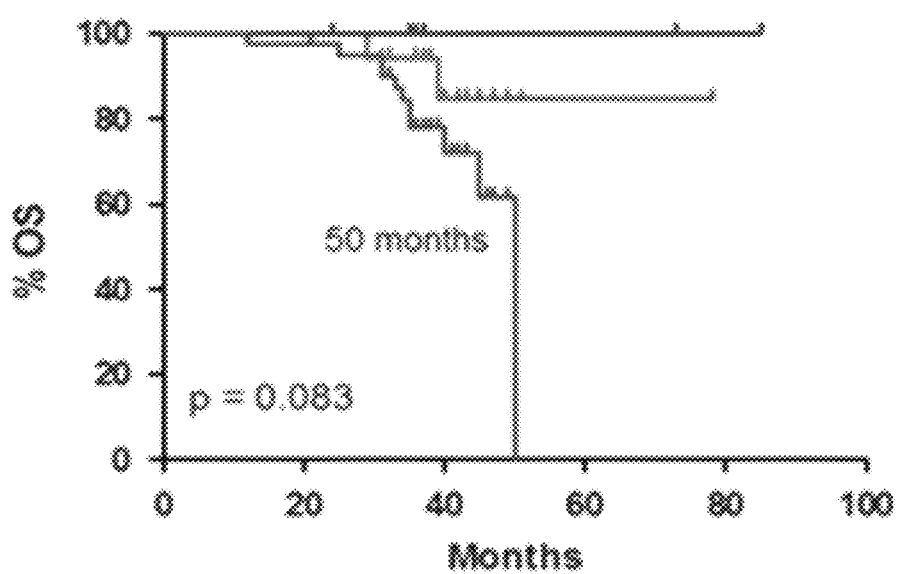
FIG. 13. Comparison between deep-sequencing (NGS) and multiparameter flow cytometry (8c-MFC) data. Overall survival (OS) plot of patients grouped according to concordance of MRD levels between NGS and 8c-MFC. Data corresponds to patients with MRD-negative values (MRD<$10^{-5}$) by both methods (8c-MFC negative, NGS negative; line showing approx. 100% OS); MRD-positive values (MRD>$10^{-5}$) by both methods (8c-MFC positive, NGS positive; line showing 50% PFS at 32 months); and MRD with discrepant data between NGS and 8c-FCM (discordant 8c-MFC and NGS).

Sixty-six of these patients were also analyzed for MRD by MFC using an eight-color monoclonal antibody combination (8c-MFC). The levels of MRD obtained with the present method have a high degree of correlation with those assessed by 8c-MFC (total 66 patients, n=175 samples, Spearman coefficient R=0.7917, P<0.0001; n=109 post-treatment samples, R=0.6388, Po0.0001), with a global 89% concordance between MFC and NGS data (FIG. 11). Accordingly, there were no significant differences in terms of PFS and OS between the data obtained by the present method of quantifying the level of MRD, and that using MFC. Nevertheless, patients with discordant results between these two technologies, show an intermediate median PFS (46 months) as compared to double-positive (32 months) or double-negative (not reached) MRD values (P=0.0063; FIG. 12). At the time of the analysis, the OS for patients with discordant results was similar to that of NGS MRD-negative patients (not reached) versus a median of 50-month survival for MRD-positive patients (P=0.0835; FIG. 13).

Due to the need of new response criteria that allows the identification of deeper responses than the now defined as clinical CR, the International Myeloma Working Group (IMWG) has defined new response categories of MRD negativity (Lancet Oncol 2016; 17: e328-e346.). One of them is sequencing MRD negative, reflecting the importance of the sensitivity of deep-sequencing methodology applied to the detection of very low numbers of tumor cells. In the new criteria, the IMGW recommends both deep-sequencing or next-generation flow to assess MRD in the BM, depending on the availability of the techniques at each center. As shown in the high degree of correlation of this study in multiple myeloma, the method of quantifying the level of MRD employed in the present invention using deep sequencing serves to define MRD negativity by sequencing as per the new criteria of the IMWG.

Conclusions:

In summary, these data confirm the clinical application of quantifying MRD levels in multiple myeloma (MM) patients using the in-house deep-sequencing method of the present invention. Said method shows a high analytical reproducibility and can be implemented in any laboratory with NGS capability, can be applied to the majority of multiple myeloma patients with a short turn-round time, has a sensitivity of $10^{-5}$ and can be fully automated (from DNA extraction to data analysis), and thus easily standardized minimizing lab-to-lab variation.

Examples Part III

Materials and Methods xiii) Samples 190 patients with de novo or secondary non-M3 AML were included in mutational profile screening at diagnosis. A selection for retrospective MRD assessment was performed using the following criteria: the NPM1 type A mutation, or point mutations (PM) in FLT3, IDH1 and/or 1DH2 at diagnosis; and availability of at least one follow-up genomic (g) DNA sample. Thus, 106 follow-up samples corresponding to 63 patients diagnosed between 2006 and 2016 were studied.

Patients were treated according to PETHEMA (Programa Espanol de Tratamientos en Hematologia) or CETLAM (Grupo cooperativo de Estudio y Tratamiento de Leucemias Agudas y Mielodisplasias) protocols. The main clinical characteristics of patients are summarised in Table 5. All participants gave written informed consent in accordance with the Declaration of Helsinki. Clinical data were collected in the following Spanish AML epidemiological registries: NCT01700413, NCT02006004, NCT00464217, NCT02607059, NCT01041040 and NCT01296178. All patients achieved CR by cytomorphological criteria after induction therapy (<5% of bone marrow blasts). 51 follow-up samples (48%) were taken at post-induction and 55 (52%) at post-consolidation. Median follow-up was 73 days (IQR 20-596).

TABLE 5

Characteristics of acute myeloid leukaemia (AML) patients included in the MRD study.

| Patients (n = 63) | Data |
|---|---|
| Sample type | |
| BM/PB | 58 (92%)/5 (8%) |
| Sex | |
| Male/Female | 21 (33%)/42 (67%) |
| Age at diagnosis | |
| Median | 54 (IQR, 41.5-66.0) |
| Blasts at diagnosis (n = 48) | |
| Median count | 69 (IQR, 42.25-81.25) |
| Leukocytes at diagnosis (n = 31) | |
| Median count ($\times 10^9$/L) | 14.05 (IQR, 3.80-39.80) |
| AML secondary (n = 33) | |
| No/Yes | 29 (0.46%)/4 (0.06%) |
| ECOG (n = 23) | |
| 0/1/2/3/ | 7 (0.11%)/10 (0.16%)/4 (0.06%)/1 (0.01%) |
| Cytogenetic risk (n = 43) | |
| Favorable/Intermediate/Adverse | 24 (0.38%)/17 (0.27%)/2 (0.03%) |
| FLT3-ITD | |
| FLT3 negative/FLT3 positive | 49 (78%)/14 (22%) |
| HSCT | |
| No/Yes | 44 (68%)/20 (32%) |
| allo-HSCT/auto-HSCT | 7 (35%)/13 (65%) |
| Relapse | |
| No/Yes | 42 (67%)/21 (33%) |
| Death | |
| No/Yes | 40 (63%)/23 (37%) |
| Treatment* (n = 34) | |
| 3 + 7 scheme/clinical trials | 27 (43%)/7 (11%) |

To construct calibration curves, commercial (Horizon Discovery, UK) reference standard gDNA was used for somatic SNVs in IDH1 (R132C) and IDH2 (R172K). As a further source of gDNA, the OCI-AML3 cell line (ACC 582, DSMZ, Germany) was also used with the NPM1 type A mutation (c.863_864insCCTG) to examine InDels. As OCI-AML3 cells also present a SNV in DNMT3A (R882C), this was included in the technical optimization.

xiv) DNA Extraction and Quantification from Sample

DNA extraction was performed in a Maxwell® 16MDx instrument (Promega Biotech Iberica, SL) and quantified on a Qubit® 2.0 Fluorometer (Invitrogen™, Thermo Fisher Scientific, Inc., WA, USA).

xv) MDR Assessment by Next-Generation Sequencing (NGS)

The sequencing workflow included one first study at diagnosis and a second study at follow-up.

Mutational profile screening at diagnosis was done with a custom NGS myeloid panel of 32 genes [see Table 6, showing genes sequenced by NGS grouped by biological function, the chromosome where it is located, genomic coordinates (start-end) of region sequenced, the number of amplicons that the gene covers, the region of the gene that encompasses all the amplicons expressed as a percentage, and the number of exons] and also with NPM1 analysis by q-PCR (Leukemia 2006, 20:1103-1108).

The custom NGS myeloid panel of 32 genes was sequenced by NGS grouped by biological function, the chromosome where it is located, genomic coordinates (start-end) of region sequenced, the number of amplicons that the gene covers, the region of the gene that encompasses all the amplicons expressed as a percentage, and the number of exons.

TABLE 6

Genes included in the NGS panel

| | Gene | Chr | Start | End | Amplicons | Coverage (%) | Exons |
|---|---|---|---|---|---|---|---|
| Trancription factor | ETV6 | Chr 12 | 11802955 | 12044078 | 20 | 94 | 8 |
| | RUNX1 | Chr 21 | 36164534 | 36421235 | 18 | 69 | 10 |
| Signaling molecular | EPOR | Chr 19 | 11488599 | 11495009 | 21 | 93 | 8 |
| | FLT3 | Chr 13 | 28578144 | 28644774 | 53 | 97 | 24 |
| | HRAS | Chr 11 | 532519 | 534348 | 10 | 83 | 5 |
| | JAK2 | Chr 9 | 5021946 | 5126885 | 57 | 97 | 23 |
| | SH2B3 | Chr 12 | 111855922 | 111886159 | 15 | 64 | 7 |
| Epigenetic Regulation | DNMT3A | Chr 2 | 25457019 | 25523119 | 51 | 91 | 25 |
| | IDH1 | Chr 2 | 209101751 | 209116313 | 22 | 98 | 8 |
| | IDH2 | Chr 15 | 90627407 | 90634952 | 21 | 87 | 11 |
| | TET2 | Chr 4 | 106155047 | 106197701 | 64 | 99 | 10 |
| | ASXL1 | Chr 20 | 30954090 | 31025087 | 52 | 91 | 13 |
| | KDM6A | Chr X | 44732713 | 44970702 | 64 | 93 | 29 |
| | KMT2A | Chr 11 | 118339409 | 118392930 | 145 | 96 | 37 |
| | MPL | Chr 1 | 43803438 | 43818424 | 30 | 92 | 12 |
| | PHF6 | Chr X | 133511597 | 133559416 | 22 | 98 | 11 |
| Transcriptional regulation | CBL | Chr 11 | 119077153 | 119170540 | 41 | 93 | 16 |
| | EZH2 | Chr 7 | 148504653 | 148544423 | 44 | 99 | 21 |
| | KIT | Chr 4 | 55524151 | 55604786 | 51 | 99 | 22 |
| | KRAS | Chr 12 | 25362621 | 25398385 | 10 | 83 | 5 |
| | NRAS | Chr 1 | 115251095 | 115258874 | 9 | 100 | 4 |

TABLE 6-continued

Genes included in the NGS panel

|  | Gene | Chr | Start | End | Amplicons | Coverage (%) | Exons |
|---|---|---|---|---|---|---|---|
|  | CALR | Chr 19 | 13049314 | 13055076 | 23 | 86 | 9 |
| Splicing | SF1 | Chr 11 | 64532722 | 64545911 | 30 | 80 | 19 |
|  | SF3A1 | Chr 22 | 30730553 | 30752852 | 37 | 94 | 18 |
|  | SF3B1 | Chr 2 | 198256947 | 193299851 | 66 | 97 | 26 |
|  | SRSF2 | Chr 17 | 74732208 | 74733231 | 5 | 70 | 2 |
|  | U2AF35 | Chr 21 | 44513107 | 44524598 | 15 | 87 | 10 |
|  | ZRSR2 | Chr X | 15808511 | 15841407 | 26 | 97 | 11 |
|  | PRPF40B | Chr 12 | 50024310 | 50037977 | 54 | 95 | 26 |
| Tumor supressor | PTEN | Chr 10 | 89624161 | 89725315 | 21 | 93 | 9 |
|  | TP53 | Chr 17 | 7572847 | 7579960 | 21 | 93 | 13 |
|  | VHL | Chr 3 | 10183314 | 10195319 | 27 | 55 | 3 |

Figure 4:
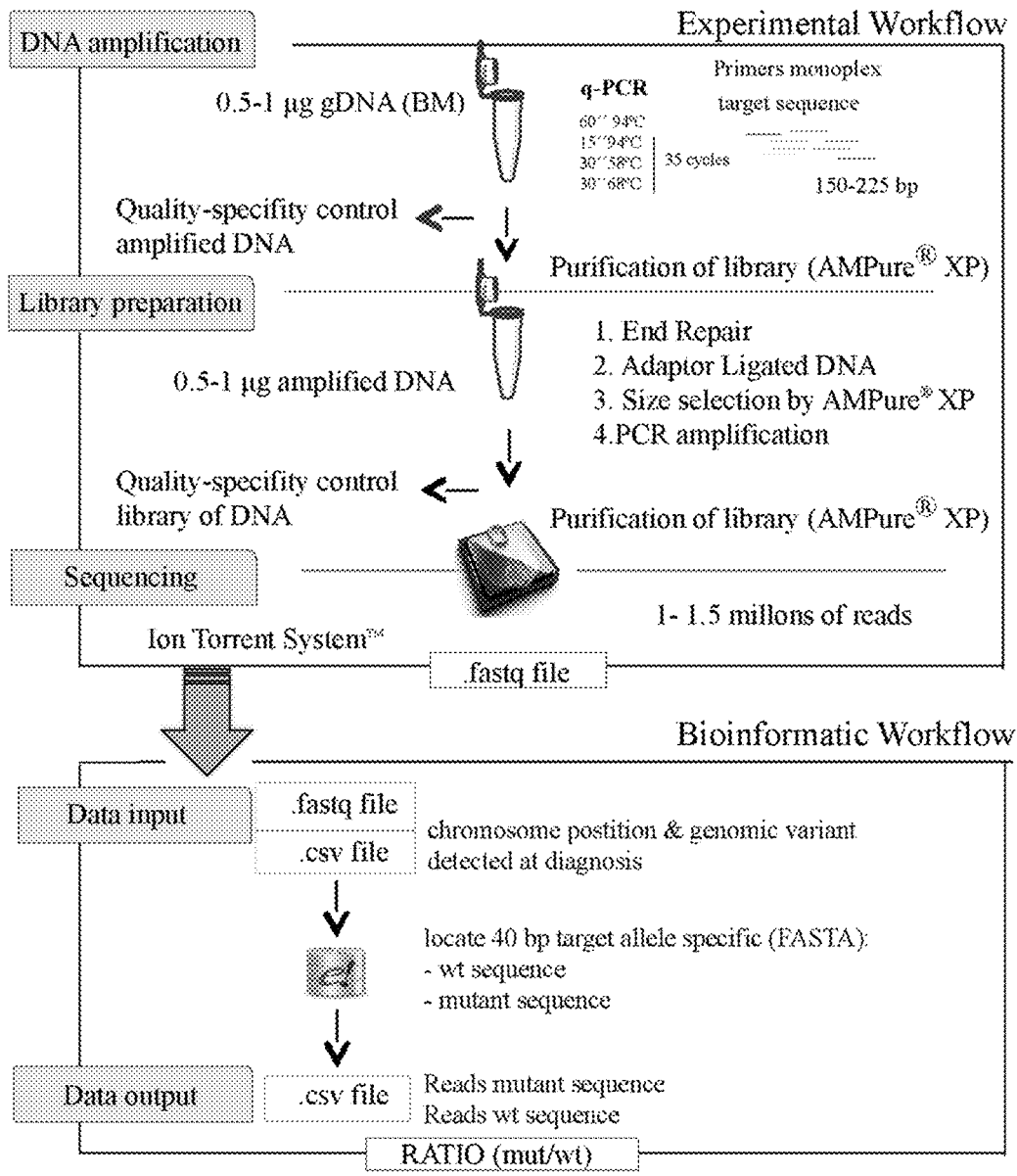
FIG. 4. DNA amplification, library preparation and sequencing experimental workflow of next-generation sequencing (NGS) method of the present invention. In particular, gDNA is amplified by q-PCR using specific primers. The product is purified, and the quality and specificity are measured. Library preparation may be carried out using a commercial kit, in four steps: end repair, adaptor ligation, size selection, and PCR amplification. The products are then purified, and the quality and specificity are measured. The library is then sequenced by NGS. A custom bioinformatic tool analyses the obtained sequences, focusing the search on the precise position and delimiting the chromosome region through Ensemble perl API annotation. This approach discriminates wild-type sequences from mutated sequences at specific positions and specific alternative fixed variants. The results are expressed as a ratio of sequences mutated among wild-type sequences.

The specific mutations detected at diagnosis were studied at follow-up. Previously, a variety of experimental steps were tested, to establish a protocol (FIGS. 4 and 19) that included DNA amplification, library preparation and sequencing as experimental steps. To do this, the same primer pairs selected from Table 7 for specific mutations used at diagnosis were used to amplify 0.5-1 µg of gDNA (3 µg in standard dilution assays by PCR using Platinum™ Taq DNA Polymerase High Fidelity (Invitrogen™, Thermo Fisher Scientific, Inc.) under the following conditions: 60 seconds at 94° C. for initial denaturation, followed by 35 cycles of 15 seconds at 94° C. for denaturation, 30 seconds at 58° C. for annealing and 30 seconds at 68° C. for extension. The final volume was 100 µL (79.6 µL DNA-H₂O, 10 µL 10× High Fidelity PCR Buffer, 4 µL 50 nM MgSO₄, 2 µL 10 mM dNTP Mix (NZYMix, Lda), 0.4 µL DNA polymerase (5 U/µL), 2 µL of 10 µM forward primer and 2 µL of 10 µM reverse primer. At diagnosis said primers were selected from the pairs of forward and reverse primers shown in Table 7, wherein specific primer (TIB MOLBIOL, Roche Diagnostics, SL) sequences were taken from a custom AML panel used at diagnosis (Ion AmpliSeq™ Thermo Fisher Scientific, Inc) for DNMT3A (used only for optimisation), IDH1, IDH2 and FLT3, or from a commercial panel (Ion AmpliSeq™ AML Panel) in the case of NPM1. Said selected primers were used in subsequent follow-ups,

TABLE 7

Sequences of primers selectable for MRD assays in patients suffering from acute myeloid leukaemia or other myeloid neoplasms

| Gene | Primer sequence 5'-3' | Sequence identifier | Sense |
|---|---|---|---|
| IDH1 | AAGAATAAAACACATACAAGTTGGAAATTTCT | SEQ ID NO: 138 | Forward |
|  | GAGAAGCCATTATCTGCAAAAATATCCC | SEQ ID NO: 139 | Reverse |
| IDH2 | ACAAAGTCTGTGGCCTTGTACTG | SEQ ID NO: 140 | Forward |
|  | CTGGACCAAGCCCATCACCAT | SEQ ID NO: 141 | Reverse |
| NPM1 | GTTAACTCTCTGGTGGTAGAATGAAAAATAGA | SEQ ID NO: 142 | Forward |
|  | GATATCAACTGTTACAGAAATGAAATAAGACG | SEQ ID NO: 143 | Reverse |
| FLT3 | TTGGAAACTCCCATTTGAGATCATATTCAT | SEQ ID NO: 144 | Forward |
|  | TCTATCTGCAGAACTGCCTATTCCTAA | SEQ ID NO: 145 | Reverse |
| DNMT3A | GATGACTGGCACGCTCCAT | SEQ ID NO: 146 | Forward |
|  | GCTGTGTGGTTAGACGGCTTC | SEQ ID NO: 147 | Reverse |
| FLT3 a | GGGAGAAAAGGCAGACTTTAAGGG | SEQ ID NO: 148 | Forward |
|  | GAAGATCTTCTTTGCTTTGCATATCAAGT | SEQ ID NO: 149 | Reverse |
| NRAS A | CAATAACACCAGCACTCCTCCAA | SEQ ID NO: 150 | Forward |
|  | GAAATACGCCAGTACCGAATGAAAAA | SEQ ID NO: 151 | Reverse |
| NRAS B | TGGATCACATCTCTACCAGAGTTAATCA | SEQ ID NO: 152 | Forward |
|  | GATTTGCCAACAAGGACAGTTGA | SEQ ID NO: 153 | Reverse | xvi) Preparation of Libraries

Libraries were constructed using NEBNext® Fast DNA Library Prep Set for Ion Torrent™ (New England Biolabs, Inc., Ipswich, Mass., USA). Specificity and quantification of the final product, both for amplified DNA and amplified libraries, was analysed with the Agilent Bioanalyser 2100 (Agilent Technologies, Palo Alto, Calif., USA).

xvii) Massive Parallel Sequencing

Finally, the libraries were sequenced on the Ion Proton System platform (Life Technologies, Thermo Fisher Scientific Inc.) with an estimated depth from 1 to 1.5 million reads, generating .fastq files. These files were analysed with the method of quantifying the level of MRD employed in the present invention that specifically detects target mutated sequences and wild-type sequences in absolute values. Using Ensembl perl API,[19] the search was focused at the precise position and mapping chromosome regions of 40 bp, which included the position of the mutation.

xviii) Digital PCR of NMP1 and IDH1/2 Mutations

Digital PCR (dPCR) for 10-fold dilutions curves of NPM1, IDH1 and/or IDH2 mutated gDNA was performed with specific primers and probes. Allele frequency was calculated as an absolute value as the ratio of mutated copies/μL to wild-type copies/μL. The dPCR assays were performed using QuantStudio™ 3D Digital PCR System using the FAM™/VIC® TaqMan® Assay (Applied Biosystems™, Thermo Fisher, La Jolla Calif., USA) to study NPM1 type A (c.863_864insTCTG), IDH1 (c.394C/T) and IDH2 (c.515G/A). A final volume of 14.5 μL (7.5 μL of PCR Master Mix 2×, 0.75 μL TaqMan® Assay 20× and 6.75 μL of gDNA at 50 ng/μL) was loaded into a QuantStudio™ 3D Digital PCR Chip v2 (Thermo Fisher) and amplified by PCR using the GeneAmp® 9700 system (Thermo Fisher). PCR was performed according to the following conditions: 10 minutes at 96° C. for initial denaturation, 39 cycles of 2 minutes at 56-60° C. followed by 30 seconds at 98° C., and a final 2 minutes step at 60° C. After the PCR, each chip was read individually using the QuantStudio™ 3D Digital PCR Instrument (Thermo Fisher Scientific, Inc), which generates a file (.eds) containing the processed image data that is then interpreted using QuantStudio™ 3D AnalysisSuite Software (Thermo Fisher).

xix) MRD Monitoring of NMP1 by q-PCR

Detection and quantification of mutated NPM1 transcripts was performed by allele-specific q-PCR, according the procedure described in Leukemia 2006, 20:1103-1108. Note that this study was carried out with RNA. For normalisation of the expression of mutated NPM1, ABL1 or GUS-β expression was used as a control. MRD-positive status was considered as the presence of NPM1 copies >0.001% after therapy.

xx) MRD Monitoring by MFC

After erythrocyte lysis, follow-up bone marrow samples were analysed using a panel of 4-colour monoclonal antibodies for the detection of the same immunophenotypic alterations described at diagnosis (Leukemia 2012, 26:1730-1741). MRD-positive status by flow cytometry was considered as the presence of AML cells greater than 0.1% at post therapy.

xxi) Statistical Analyses

Contingency tables were used to analyse associations between categorical variables using Fisher's exact test or Chi-square test for statistical significance. Student's t-test was used to compare averages of continuous variables between groups. The concordance between sequencing, MFC and q-PCR was analysed in log space using the Spearman correlation test. ROC (Receiver Operating Characteristic) curves were employed to establish the cutoff value to predict survival. For survival analysis, the endpoints examined were disease-free survival (DFS) and overall survival (OS), from the starting point of the treatment. Survival curves were calculated according to the Kaplan-Meier method and the log-rank test was used for estimation of survival and differences between groups. Univariate and multivariate analyses were performed using the Cox regression model. Statistical analyses were performed using the R statistical software platform. All p-values were two-sided, with statistical significance defined as a p-value of 0.05 or less.

Example 5. Novel Deep Targeted Sequencing Method for Minimal Residual Disease Monitoring in Acute Myeloid Leukaemia as a Useful Tool to Predict Relapse and Survival A high-throughput sequencing method for MRD assessment in acute myeloid leukaemia patients (i.e. the quantification of the level of MRD), by measuring levels of cell clonotypes with mutations of NPM1, IDH1/2, and FLT3 single nucleotide variants (SNV) was designed and evaluated. For clinical validation, DNA from acute myeloid leukaemia (AML) patients (n=190) was analysed at diagnosis using a custom next-generation sequencing (NGS) AML panel of 32 genes. In addition, NPM1 was analysed by quantitative (q)-PCR, and FLT3 internal tandem duplication (ITD) mutations were assessed by GENESCAN (n=233). 106 follow-up samples from 63 AML patients in complete remission after therapy under PETHEMA or CETLAM protocols were available. Predictive value of MRD status by NGS, multiparameter flow cytometry (MFC), and q-PCR was determined by survival analysis.

Results:

92% of AML patients could benefit from deep sequencing MRD approach

In total, 227 single nucleotide polymorphisms (77.6%) and 80 InDels (22.4%) were detected in 190 patients analysed at diagnosis using the NGS 32 gene custom panel. One variant was detected in 23 cases (12%), 2 or more variants in 156 cases (82%) and no variants in 11 cases (6%). In addition, the NPM1 type A mutation was detected in 53 (28%) patients by q-PCR. Focus was only on MRD markers with potential relevance for relapse (Blood 2016, 128:686-698), and as such the need to examine variants located in genes associated with preleukemic status (TET2, SRSF2, ASXL1, or DNMT3A) was obviated. Consequently, 92% of patients in the cohort could benefit from this approach.

Based on those genes reported as potential markers to monitor MRD (Expert Rev. Hematol. 2017, 10:563-574), and also the availability of follow-up samples, focus was placed on IDH1/2 and FLT3-SNV. IDH1 mutations were identified in 13 patients (7%), IDH2 mutations in 27 patients (14%) and FLT3-SNV mutations (18%) in 34 patients.

Deep Sequencing MRD has a Sensitivity of $10^{-4}$-$10^{-6}$

Figure 14:
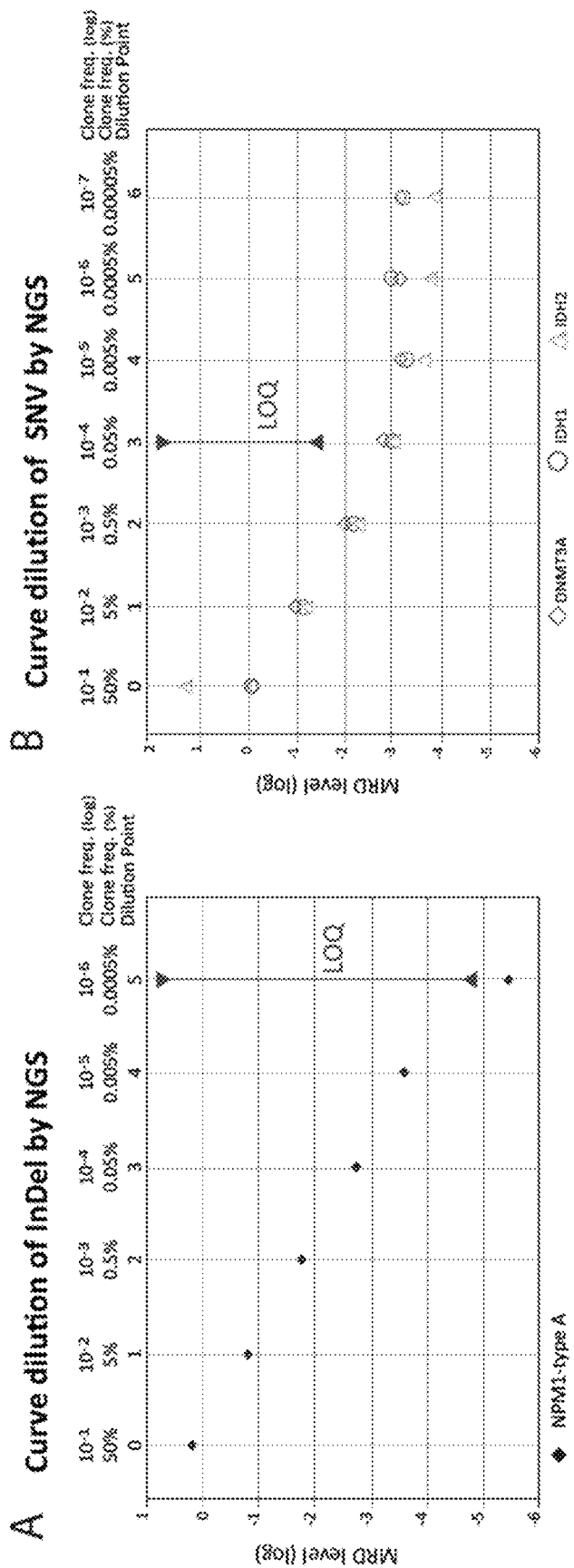
FIG. 14. Calibration curve of MRD in serial dilutions (upper panels) 10-fold dilution curve for the assessment of sensitivity of sequencing in InDels (panel A), using OCI-AML3 gDNA with 50% NPM1 type A mutation ($R^2$=0.98); and in point mutations (panel B), using OCI-AML3 gDNA with 50% mutated DNMT3A ($R^2$=0.98), and gDNA with 50% mutated IDH1 or IDH2, from a commercial standard ($R^2$=0.91, $R^2$=0.98, respectively); (lower panels), 10-fold dilution curve for the assessment of sensitivity of dPCR in InDels (panel C), using OCI-AML3 gDNA with 50% NPM1 type A mutation ($R^2$=0.98); and in point mutations (panel D) ($R^2$=0.98), using gDNA with 50% mutated IDH1 or IDH2, from a commercial standard ($R^2$=0.91 and $R^2$=0.98, respectively). Vertical bars indicate LOQ according to the sample. Clone frequency is expressed as target concentration in mutated copies/µL in wild-type copies/µL.
Figure 14:
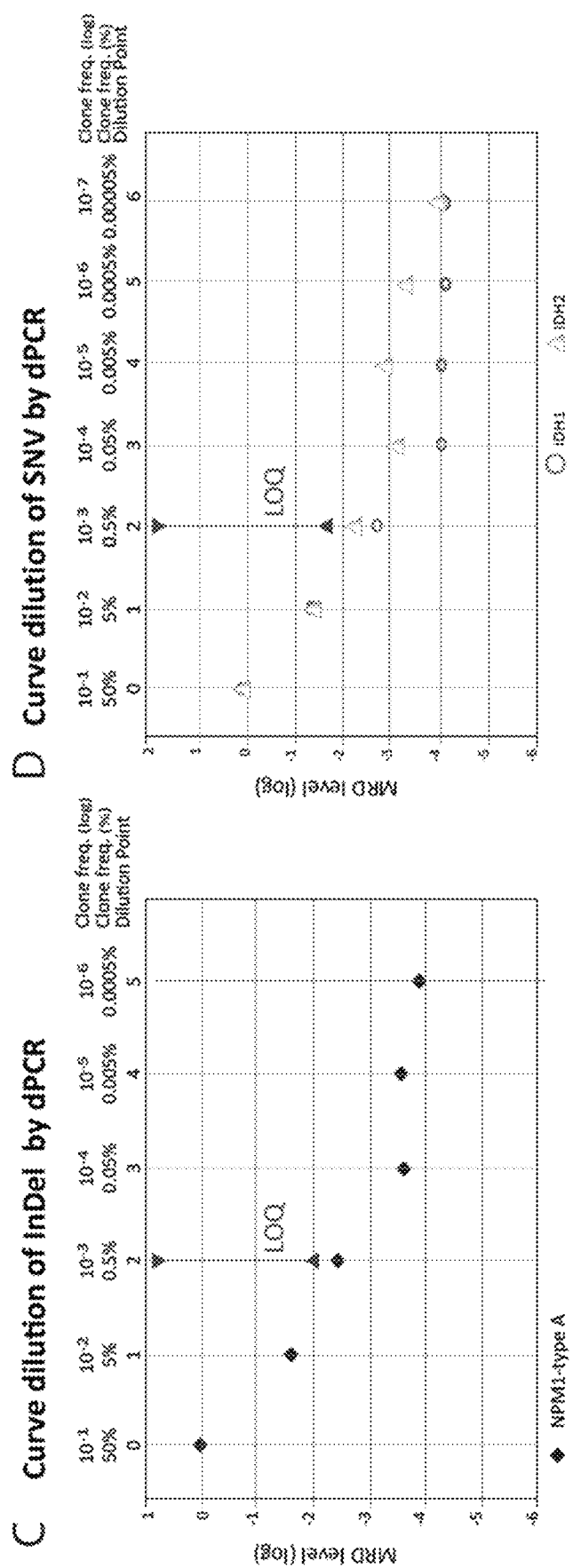

To establish the limit of quantification (LOQ) of the method, 10-fold serial dilutions of mixed mutated and control DNA were used. In order to study prototype InDels (NPM1 type A and DNMT3A R882C), gDNA from OCI-AML3 cells (DNMT3A) and commercial reference gDNA (IDH1 and IDH2) were used to study prototype SNVs. Also used was a commercial reference gDNA for PM in IDH1 and IDH2. As OCI-AML3 cells also present a PM in DNMT3A, this was also included in the technical validation. As a control, a pool of gDNA from ten control individuals without somatic mutations in these chromosomal regions was used. In all cases, initial allele frequency was 50% and a total of six dilutions was carried out to construct a calibration curve, covering a theoretical dynamic range from $10^{-1}$ to $10^{-7}$. As shown in FIG. 14, MRD testing by next-generation sequencing of NPM1 (InDel) could quantify one mutated cell in one million (LOQ $10^{-6}$) [FIG. 14, panel A], and in the case of PM (IDH1, IDH2 and DNMT3A) the LOQ was $10^{-4}$, which was reproducible for all SNVs tested [FIG. 14, panel B]. The patients achieving an MRD-negative status were not subjected to further treatment. However, the remaining patients who failed to achieve an MRD-negative status (i.e. which still were determined to have MRD) were subjected to further treatment for acute myeloid leukaemia using a further 3+7 scheme of intensive chemotherapy therapy, following which MRD status was again determined.

Next-Generation Sequencing (NGS) is More Sensitive than dPCR for MRD

The sensitivity of sequencing was compared with that of dPCR using the same LOQ dilution protocol. Clone frequency expressed as target concentration (mutated copies/

μL in wild-type copies/μL) gradually decreased at each dilution, reaching an LOQ of $10^{-3}$ for NPM1, IDH1 and IDH2 as shown in [FIG. 14, panel C and FIG. 14, panel D]. While both methods showed similar detection limits and good linearity, the LOQ for the sequencing method was one order of magnitude higher than that for dPCR for PM (IDH1 and IDH2), and two orders of magnitude higher for InDels (NMP1).

MRD Status Tested by Sequencing has Prognosis Impact in AML

Median of depth coverage was 401,300 reads (range 7,362-1,939,645) for the 88 NPM1 samples and 18 SNV (9 IDH1, 7 IDH2, and 2 FLT3) follow-up samples evaluated.

Figure 15:
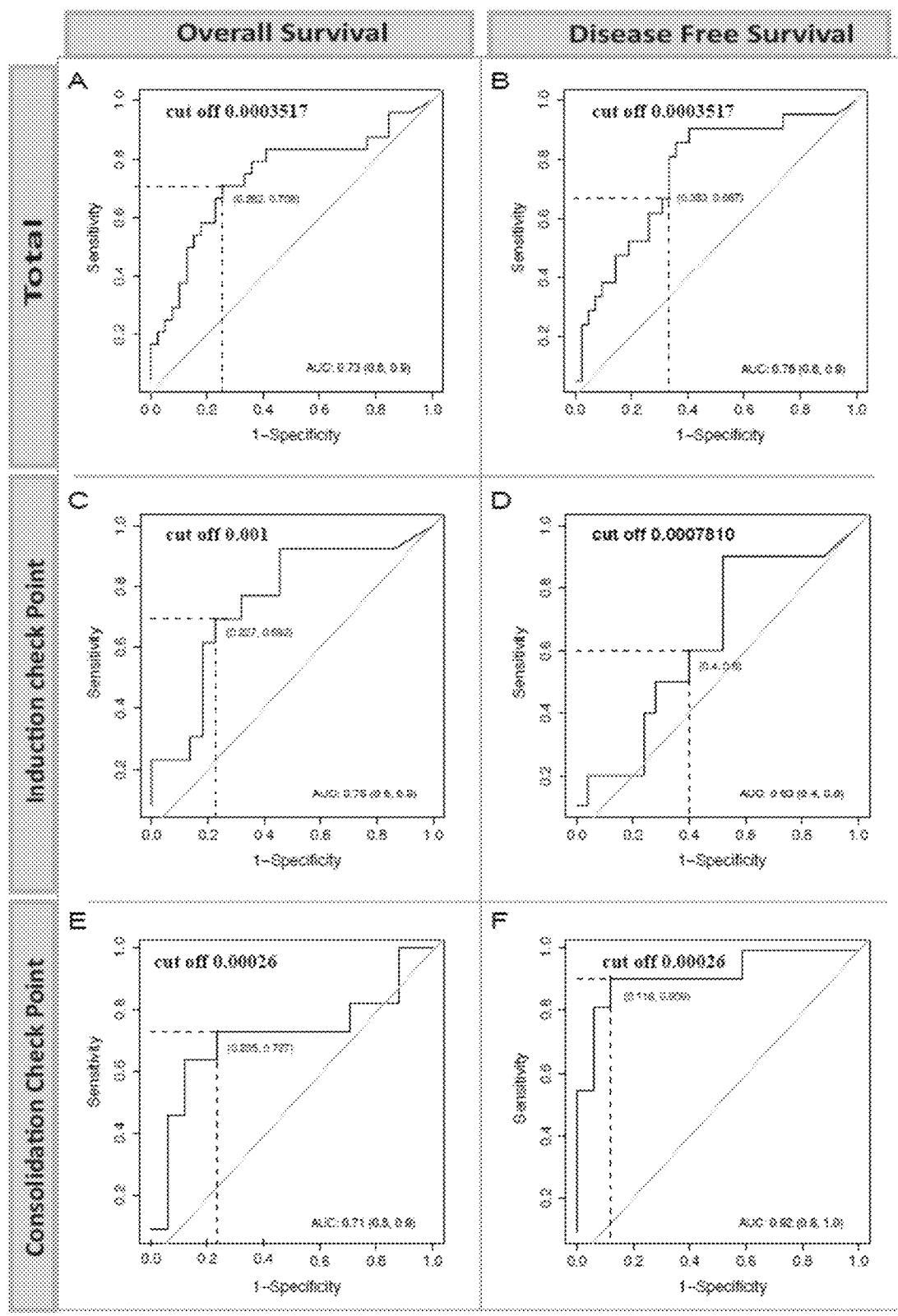
FIG. 15. ROC curves. Plots show the sensitivity or true positive rate (TPR) in the y-axis against 1-specificity or the false positive rate (FPR) in the x-axis, at various threshold settings. ROC curves determined the optimal cutoff level which maximizes sensitivity and specificity for 63 cases evaluated at each checkpoint: global, postinduction and post-consolidation. Both OS (left-hand panels A, C and E) and DFS data (right-hand panels B, D and F) are estimated. Area under the curve (AUC) and 95% CI is annotated.

We detected no mutated sequence in 13 (12%) samples, 1-5 mutated sequences in 19 (18%) samples, and more than 10 in 74 (70%) samples. The ratio of mutated sequences to wild-type sequences defined MRD levels. Considering MRD levels from the 106 samples evaluated we established the optimal cutoff to classify MRD status (positive vs negative) by ROC curves (FIG. 15) at each check-point of MRD evaluation (post-induction, post-consolidation or both).

Figure 16:
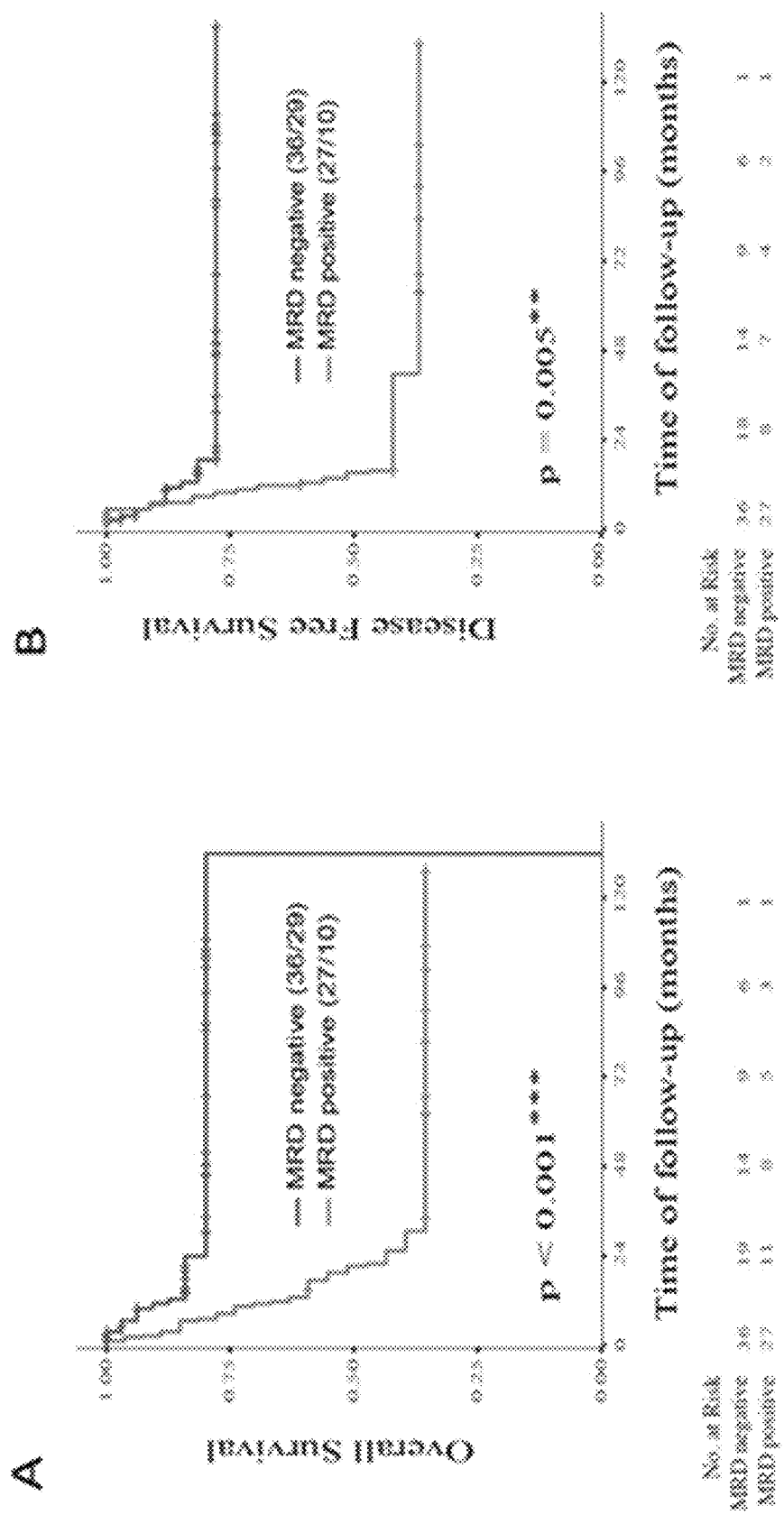
FIG. 16. Analysis of overall survival and disease-free survival in AML patients stratified according to MRD levels by sequencing. Kaplan-Meier plots of overall survival (OS, left-hand panels A, C and E) and disease-free survival (DFS, right-hand panels B, D and F), revealing prognostically different groups: (panel A) OS for all data sets; (panel B)
Figure 16:
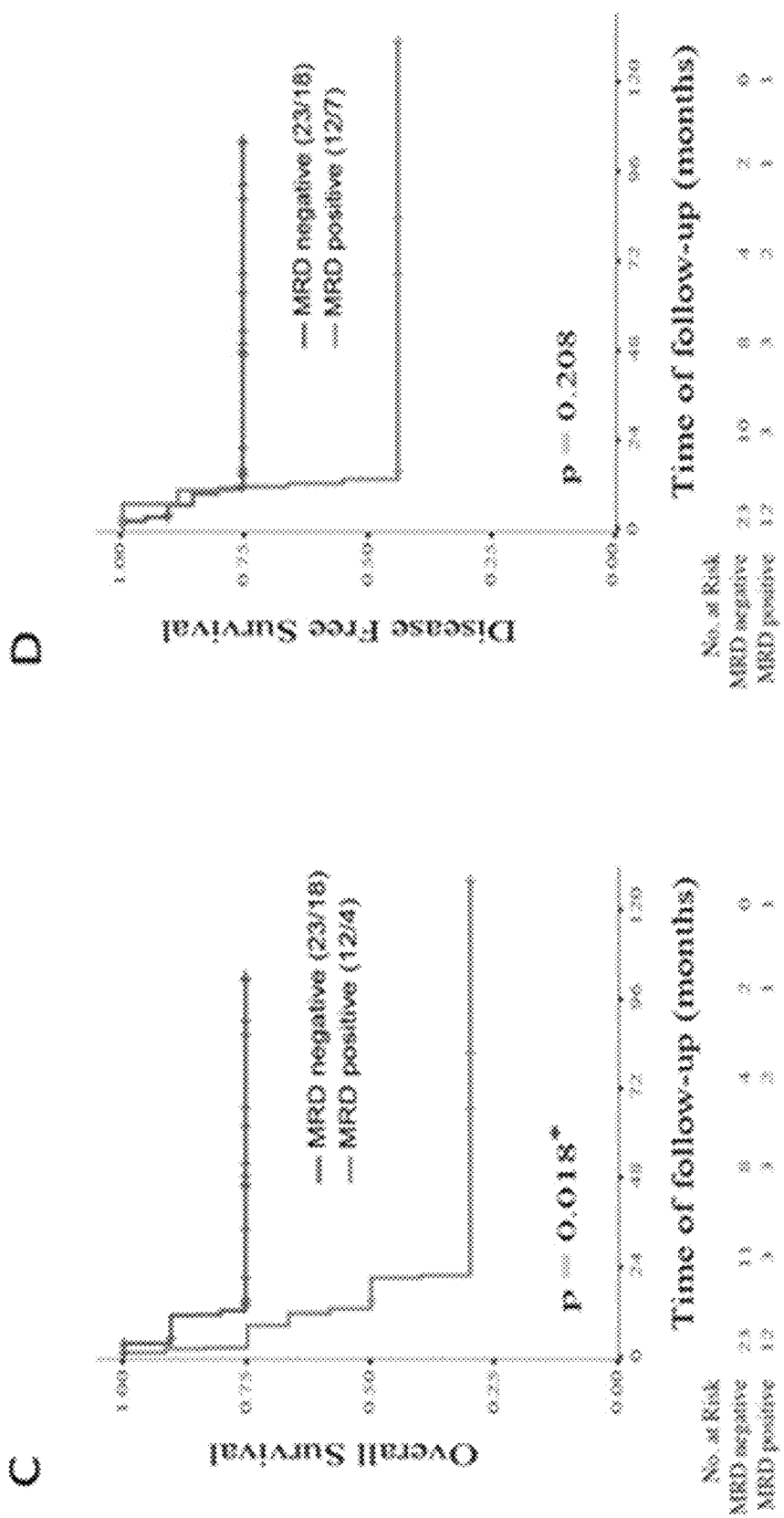
Figure 16:
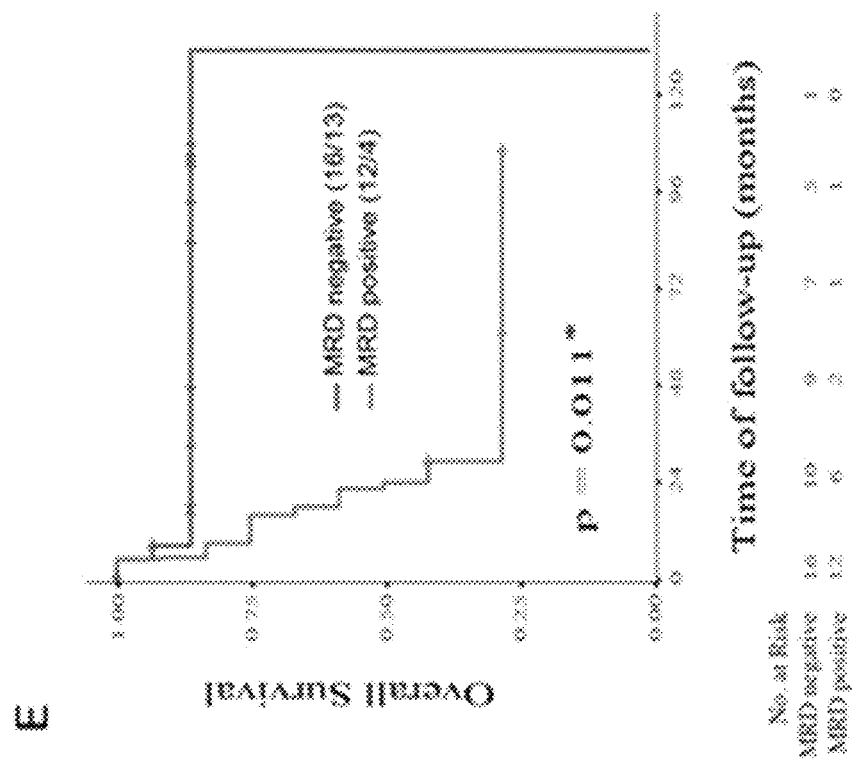

Survival analysis shown in FIG. 16 revealed that positive MRD status (patients with MRD levels >0.035%) was associated with a higher risk of relapse (48% vs 81%; HR: 3.4; 95% CI: 1.4-8.5; p=0.005) and death (37% vs 81%; HR: 4.2; 95% CI: 1.6-10.7; p<0.001) [FIG. 16(A) and FIG. 16(B)]. Considering only samples obtained at post-induction (n=35), we found that positive MRD status (MRD levels >0.1%) was associated with a significantly lower rate of OS (33% vs 78%; HR: 3.5; 95% CI: 1.1-10.7; p=0.019), but a non-significant lower rate of DFS (58% vs 78%; HR:2.18; 95% CI:0.63-7.5; P=0.208) [FIG. 16(C) and FIG. 16(D)]. At post-consolidation (n=28), MRD positive status (MRD levels >0.025%) was associated both with significantly shorter OS (33% vs 81%; HR:6.0; 95% CI:1.3-28.7; P<0.001), and significantly shorter DFS (17% vs 94%; HR:19.6; 95% CI: 2.5-155.6; P<0.001) [FIG. 16(E) and FIG. 16(F)].

In univariate analysis (Table 8 shows univariate Cox regression analysis of each prognostic factor influencing the risk of relapse and risk of death of AML patients, for both risk of death and risk of relapse), the risk of death was significantly higher in patients with an increased age (HR: 1.04; 95% CI: 1.00-1.07; p=0.013), those with FLT3-ITD (HR: 3.45; 95% CI: 1.40-8.52; p=0.007), and those with MRD-positive status tested by NGS (HR: 4.22; 95% CI: 1.66-10.71; p=0.002). Risk of relapse was significantly higher only in those patients with MRD-positive status tested by NGS (HR: 3.4; 95% CI: 1.37-8.49; p=0.008).

TABLE 8

Univariate Cox regression analysis.

| | Risk of Death | | Risk of Relapse | |
|---|---|---|---|---|
| | HR (95% CI) | $p_{value}$ | HR (95% CI) | $p_{value}$ |
| Sex (female vs male) | 1.20 (0.50-2.83) | 0.682 | 0.94 (0.37-2.44) | 0.906 |
| Age per year | 1.04 (1.00-1.07) | 0.013* | 1.03 (0.99-1.06) | 0.069 |
| Increase in blasts at dx (%) | 1.00 (0.98-1.03) | 0.738 | 1.00 (0.99-1.03) | 0.476 |
| Increase in leukocytes at dx ($\times 10^9$/l) | 1.01 (0.99-1.03) | 0.077 | 1.02 (0.99-1.03) | 0.074 |
| Decrease in ELN risk | 0.71 (0.09-5.72) | 0.752 | 0.77 (0.10-6.12) | 0.800 |
| Increase in ELN risk | 1.52 (0.18-12.5) | 0.692 | 1.24 (0.14-10.6) | 0.844 |
| Mutated NPM1 (yes vs no) | 1.39 (0.51-3.76) | 0.514 | 2.04 (0.78-5.28) | 0.141 |
| Mutated FLT3-ITD (no vs yes) | 3.45 (1.40-8.52) | 0.007** | 2.37 (0.86-6.51) | 0.095 |
| Intensive qt to Allo-HSCT | 1.56 (0.39-6.29) | 0.531 | 1.64 (0.32-8.52) | 0.551 |
| Auto-HSCT to Allo-HSCT | 0.28 (0.05-1.68) | 0.164 | 0.62 (0.10-3.77) | 0.559 |
| MRD⁺ by MFC | 2.10 (0.67-6.62) | 0.203 | 2.40 (0.77-7.46) | 0.130 |
| MRD⁺ by q-PCR | 2.51 (0.56-11.2) | 0.228 | 5.01 (0.64-38.8) | 0.123 |
| MRD⁺ by NGS | 4.22 (1.66-10.7) | 0.002** | 3.41 (1.37-8.48) | 0.008** |

*p-values are considered significant (<0.05),
**(<0.01).
HR, hazard ratio;
CI, confidence interval,
dx, diagnosis;
ELN, European Leukaemia Net;
qt, chemotherapy;
allo-HSCT, allogeneic haematopoietic stem-cell transplantation;
auto-HSCT, autologous haematopoietic stem-cell transplantation;
MRD, minimal residual disease;
MFC, multiparametric flow cytometry;
NGS, next-generation sequencing.

In multivariate analysis (Table 9 shows multivariate Cox regression analysis evaluating most relevant factors for predicting risk of death and risk of relapse in AML patients), the risk of death was significantly higher in patients with an increased age (HR: 1.03; 95% CI: 1.00-1.60; p=0.030), those with mutated FLT3-ITD (HR: 4.56; 95% CI: 1.69-12.3; p=0.003), or those with MRD-positive status tested by NGS (HR: 3.91; 95% CI: 1.47-3.36; p=0.030). As expected, the risk of relapse was higher in MRD-positive patients tested by NGS (HR: 4.37; 95% CI: 1.65-11.54; p=0.015).

TABLE 9

Multivariate Cox regression analysis.

| | Risk of Death | | Risk of Relapse | |
|---|---|---|---|---|
| | HR (95% CI) | $p_{value}$ | HR (95% CI) | $p_{value}$ |
| Age per year | 1.03 (1.00-1.60) | 0.030* | 1.02 (0.99-1.06) | 0.169 |
| Sex (female vs male) | 1.25 (0.48-3.25) | 0.645 | 0.80 (0.29-2.20) | 0.669 |
| Mutated NPM1 (yes vs no) | 1.17 (0.41-3.36) | 0.760 | 1.83 (0.69-4.85) | 0.221 |

TABLE 9-continued

Multivariate Cox regression analysis.

|  | Risk of Death | | Risk of Relapse | |
| --- | --- | --- | --- | --- |
|  | HR (95% CI) | $p_{value}$ | HR (95% CI) | $p_{value}$ |
| Mutated FLT3-ITD (no vs yes) | 4.56 (1.69-12.3) | 0.003** | 2.55 (0.90-7.25) | 0.220 |
| MRD+ by NGS | 3.91 (1.47-10.3) | 0.006** | 3.31 (1.29-8.55) | 0.013* |

*p-values are considered significant (<0.05),
**(<0.01).
HR, hazard ratio;
CI, confidence interval,
MRD, minimal residual disease;
NGS, next-generation sequencing.

MRD tested by sequencing improves prediction of OS and DFS over MFC and q-PCR A positive correlation was found when comparing MRD assessment by NGS vs MFC (r=0.47, p=0.005), and NGS vs q-PCR (r=0.62, p<0.001) for the complete data set of samples studied (n=106) (FIG. 16). As shown in FIG. 17, there were differences between positive MRD and negative MRD groups of patients tested by MFC, but they were not significant for OS (p=0.193) or DFS (p=0.117). Similarly, differences were observed between positive MRD and negative MRD groups by q-PCR of NPM1 although significance was not reached for OS (p=0.212) or DFS (p=0.086).

Discussion

This Example shows that a high sensitivity MRD-NGS method has been validated to detect and quantify NPM1, IDH1/2 and FLT3-SNV mutated sequences at very low allele frequency in follow-up gDNA samples. To ensure a high applicability, the mutational profile of patients with AML was first studied using an NGS custom panel of 32 genes frequently mutated in myeloid diseases. This approach is a good screening method to choose a precise MRD marker and allowed a potential MRD marker to be detected in 92% of patients. Because the method of the present invention has the capacity to examine multiple markers and considering that 82% of patients in the cohort had two or more genetic alterations, this approach is sufficiently robust to monitor MRD in patients who present clonal evolution.

The sensitivity achieved with this method equates to one mutated cell per million cells (LOQ $10^{-6}$) for InDels and one mutated cell per 10,000 cells (LOQ $10^{-4}$) for PM. This difference in sensitivity is related to the fact that InDels, such as NPM1 type A, are rarely generated erroneously by NGS and the quantification is precise. Although it is known that this method, like any NGS method, has an intrinsic error rate that limits its sensitivity for most SNVs to around 1-2% of all reads, this limitation can nevertheless be overcome because of the scalable nature of NGS (Expert Rev. Hematol. 2017, 10:563-574). Thus, NGS sensitivity was boosted by increasing the amount of DNA by PCR prior to sequencing, which increased the depth of coverage to over one millions reads. By also optimizing the bioinformatic analysis, we focused the search for the precise variant in order to eliminate random sequencing errors, enhancing the specificity of the technique and reducing the computational time. To the best of knowledge, this presents possibly the highest sensitivity reported for a NGS method and higher than that of q-PCR or MFC, whose ranges of sensitivity are reported to be from 0.1% to 5% (Genes, Chromosom. Cancer 2012, 51:689-695; JAMA 2015, 63110:811-822; Leukemia 2014, 28:129-137; Biol. Blood Marrow Transplant. (2017) 23:1064-1071).

dPCR is a relatively novel technique for precise and absolute quantification of nucleic acids, which is based on limiting partitions of the PCR volume and Poisson statistics (J. Mol. Diagnostics 2017, 19). It is also a highly sensitive technique, with a high specificity due to the detection of mutant alleles (J. Clin. Med. 2017, 6:87). However, when the same standard dilutions were compared, NGS afforded a 2-log increment in LOQ for InDels (NPM1) and a 1-log increment for point mutations (PM) (IDH1/2) over dPCR. Moreover, the NGS technique achieved a higher sensitivity than dPCR, whose sensitivity for InDels was similar to that in previously published studies (0.05%) (Oncotarget 2016, 7(52): 86469-86479). Compared with NGS, dPCR is a faster measurement technique; however, as it is focused, it requires allele-specific primers that can complicate the experimental procedure, and a high number of parallel experiments are needed to raise the sensitivity, increasing the cost of the assay. Additionally, while dPCR multiplexing is possible, unfortunately only a few targets can be monitored simultaneously within each sample (J. Clin. Med. 2017, 6(9): E87). Another advantage of this technology is that it does not require calibration curves in each assay, and the results are reported in absolute values, facilitating its standardisation.

This example shows that the sensitivity by sequencing, $10^{-4}$ to $10^{-6}$, is also higher than that described for MFC, which is in the range $10^{-3}$-$10^{-5}$ depending on the immunophenotypically aberrant populations present in AML patients (Hematology 2016, 2016: 356-365; J. Clin. Oncol. 2013, 31, 3889-3897). Moreover, although this method shows a similar sensitivity to that of q-PCR ($10^{-4}$), it does not require oligonucleotides that hybridise specifically to a particular sequence, so all positions in the amplified region can be studied. Accordingly, the NGS test is capable of detecting all NPM1 subtype mutations in the same assay.

Positive correlations were found when MRD levels were evaluated by NGS vs MFC and q-PCR, but no such correlation was evident between NGS and MFC. This could be explained, in part, because NPM1 mutations (83% of cases) are usually associated with monocytic subtype-AML, which frequently presents more difficulties for identifying MRD by MFC. Indeed, the level of success of MFC depends greatly on the immunophenotype of the abnormal blasts and how to discriminate them from background regenerative blasts (Mod. Pathol. 2014, 27:1438-46). Moreover, due to the lack of standardisation, MFC shows substantial variability across laboratories, including sample processing, instrument configuration, number of events and training of pathologists (Int. J. Lab. Hematol. 2017, 39:53-60). The lack of a strong correlation between NGS and q-PCR could be explained by the nature of the sample (sequencing uses gDNA, while q-PCR uses cDNA). Although RNA overexpression allows a higher sensitivity of detection, in contrast to mutated DNA, RNA levels do not correlate with the number of tumoral cells. Accordingly, mutated DNA is more representative of the tumoral burden than is overexpression of mutated RNA (Am. J. Hematol. 2014, 89:610-615). It should be noted that the prediction of survival and progression of AML using MRD-NGS was improved over the other methodologies employed.

Finally, survival analysis showed that MRD-positive status tested by sequencing was associated with a higher risk of relapse and death, and that MRD-negative status at post-consolidation time was associated with a longer OS and DFS. Cox regression multivariate analysis confirmed that MRD positive status by sequencing was the only factor with significant risk prediction of relapse (p=0.015).

CONCLUSIONS

The method of quantifying the level of MRD of the present invention achieved an applicability of 94% of AML patients. This NGS-based method simplifies and standardizes MRD evaluation (i.e. the quantification of the level of MRD), with a high applicability in AML patients. It also improves upon MFC and q-PCR to predict AML outcome (presence or absence of MRD) following therapy.

The invention claimed is:

1. A method of diagnosing and therapeutically treating cancer in a subject which comprises:
   (A) diagnosing the subject with cancer when a level of minimal residual disease (MRD) in the subject is >0, wherein the MRD is quantified by:
      (a)—amplifying by polymerase chain reaction using a PCR instrument and primers, at least one nucleotide sequence comprised in an amount, D, of genomic DNA of a biological sample obtained from said subject after therapeutic treatment for said disease, wherein the genomic DNA has an average weight, k, per diploid cell of said biological sample, wherein said primers comprise a locus-specific forward primer and a locus-specific reverse primer, and said primers identify one specific variant of a nucleotide sequence present in said biological sample, wherein said one variant or the absence of said one variant is indicative of disease; and
         sequencing said at least one nucleotide sequence on a massively parallel sequencing platform to obtain at least one first list of characters reading from left to right, wherein said sequencing is massively parallel sequencing;
      (b)—amplifying by polymerase chain reaction using a PCR instrument and the same locus-specific forward primer and the same locus-specific reverse primer as in step (a), at least one nucleotide sequence in a biological sample obtained from said subject prior to therapeutic treatment for said disease; and
         sequencing said at least one nucleotide sequence on a massively parallel sequencing platform to obtain at least one second list of characters reading from left to right, wherein said sequencing is massively parallel sequencing;
      (c) determining a degree of similarity by comparing the at least one first list of characters obtained in step (a) with the at least one second list of characters obtained in step (b), wherein the degree of similarity, DS, of the first list of characters obtained in step (a) with the second list of characters obtained in step (b) is determined using at least one computer program product, either by:
         (i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;
         (ii) excluding the character or longest continuous sequence of characters selected in step (i) from subsequent steps of selecting a character or longest continuous sequence of characters which is the same in the first list of characters and the second list of characters;
         (iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
         selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected;

(iv) excluding each character and/or each longest continuous sequence of characters selected in step (iii) from subsequent steps of selecting a character or longest continuous sequence of characters which is the same in the first list of characters and the second list of characters;

(v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected;

(vi) excluding each character and/or each longest continuous sequences of characters selected in step (v) from subsequent steps of selecting a character or longest continuous sequence of characters which is the same in the first list of characters and the second list of characters;

(vii) repeating steps (v) and (vi) until no character or longest continuous sequence of characters which is the same in the first list of characters and the second list of characters is selected;

(viii) adding up
the number of characters in the first list of characters which were excluded in any of the steps (i) to (vii); and
the number of characters in the second list of characters which were excluded in any of the steps (i) to (vii)
to obtain the total number of characters, $C_c$, in the first and second lists of characters which are the same as in the second and first lists of characters, respectively;

(ix) adding up
$C_c$; and
the number of characters in the first list of characters which are located between the characters and/or longest continuous sequences of characters that were excluded from the first list of characters, and which were not excluded in any of the steps (i) to (vii) of step (c); and
the number of characters in the second list of characters which are located between the characters and/or longest continuous sequences of characters that were excluded from the second list of characters, and which were not excluded in any of the steps (i) to (vii) of step (c), to obtain the total number of characters, $C_t$, in the first and second lists of characters; and (x) calculating DS according to the following formula:

$$DS = C_c/C_t$$

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected;

(xii) excluding the character or longest continuous sequence of characters selected in step (xi) from subsequent steps of selecting a character or longest continuous sequence of characters which is the same in the first list of characters and the second list of characters;

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected;

(xiv) excluding each character and/or each longest continuous sequence of characters selected in step (xiii) from subsequent steps of selecting a character or longest continuous sequence of characters which is the same in the first list of characters and the second list of characters;

(xv) repeating steps (xiii) and (xiv) until no character or longest continuous sequence of characters which is the same in the first list of characters and the second list of characters is selected;

(xvi) adding up
the number of characters in the first list of characters which were excluded in any of the steps (xi) to (xv); and
the number of characters in the second list of characters which were excluded in any of the steps (xi) to (xv)
to obtain the total number of characters, $C_c$, in the first and second lists of characters which are the same as in the second and first lists of characters, respectively;

(xvii) adding up
C_c; and
the number of characters in the first list of characters which are located between the characters and/or longest continuous sequences of characters that were excluded from the first list of characters, and which were not excluded in any of the steps (xi) to (xv) of step (c); and
the number of characters in the second list of characters which are located between the characters and/or longest continuous sequences of characters that were excluded from the second list of characters, and which were not excluded in any of the steps (xi) to (xv) of step (c),
to obtain the total number of characters, $C_t$, in the first and second lists of characters; and
(xviii) calculating DS according to the following formula:

$$DS = C_c/C_t$$

(d) selecting using at least one computer program product, for each first list of characters obtained in step (a), the DS of highest value, $DS_{HV}$;
(e) adding up using at least one computer program product, the number of first lists of characters which have a $DS_{HV}$ that is greater than a threshold value, T, to obtain the total number of first lists of characters, $L_c$, which are the same as a second list of characters;
(f) adding up, using at least one computer program product,
$L_c$; and
the number of first lists of characters which do not have a $DS_{HV}$ that is greater than T,
to obtain the total number of first lists of characters, $L_t$; and
(g) calculating using at least one computer program product, the level of minimal residual disease (MRD) according to any of the following formulae:

$$MRD = (L_c \times k)/(L_t \times D)$$

or $$MRD = L_c/L_t$$

or $$MRD = L_c \times (D/k)/L_t^2;$$

(B) administering a therapeutic amount of chemotherapy to the subject having an MRD>0, wherein the chemotherapy comprises (i) bortezomib plus melphalan and prednisone (VMP) and lenalidomide plus dexamethasone (Rd), and/or (ii) cytarabine and an anthracycline antibiotic or an anthracenedione, optionally followed by additional cytarabine; and
(C) repeating step (A), and when the level of MRD determined in step (A) is >0, repeating step (B), until the level of MRD in step (A) equals 0.

2. The method according to claim 1, wherein
each character in each of the first and second lists of characters respectively obtained in steps (a) and (b), comprises a letter associated with a number or symbol, wherein said number or symbol represents quality (Q), wherein quality (Q) is an integer mapping of the probability that the letter which represents a nucleotide that is identified at the corresponding position in the nucleotide sequence is incorrect, and wherein said letter represents the nucleotide that is identified at the corresponding position in the nucleotide sequence having the highest quality (Q); and
a character in the first list of characters is determined in step (c) as the same as a character in the second list of characters, when the letter having the highest quality is the same in the first and second lists of characters.

3. The method according to claim 2, wherein a character in the first list of characters is determined in step (c) as the same as a character in the second list of characters, when the letter having the highest quality (Q) is the same in the first and second lists of characters, and the quality of the letter in the first list of characters is within 1 percent of the quality of the letter in the second list of characters.

4. The method according to claim 1, wherein the sequencing is massively parallel sequencing using emulsion-PCR or massively parallel signature sequencing.

5. The method according to claim 1, wherein the disease is a haematological cancer.

6. The method according to claim 1, wherein the disease is selected from a lymphoproliferative disease and a myeloid neoplasia.

7. The method according to claim 6, wherein the disease is selected from multiple myeloma, follicular lymphoma, mantle cell lymphoma, Hodgkin's lymphoma, non-Hodgkin's lymphoma, Burkitt's lymphoma, acute lymphoblastic leukaemia, acute myeloid leukaemia, chronic lymphocytic leukaemia, chronic myelogenous leukaemia, acute monocytic leukemia, atypical chronic myeloid leukaemia, juvenile myelomonocytic leukaemia, myelodysplastic syndrome, myeloproliferative neoplasm and myeloproliferative myelodysplastic syndrome.

8. The method according to claim 7, wherein the disease is selected from multiple myeloma or acute myeloid leukaemia.

9. The method according to claim 1, wherein the cancer is selected from acute lymphoblastic leukaemia, acute myeloid leukaemia, chronic lymphocytic leukaemia, chronic myelogenous leukemia, follicular lymphoma, or multiple myeloma.

10. The method according to claim 9, wherein said primers are selected from:
any of SEQ ID NO: 39 to SEQ ID NO: 137 when said disease is any lymphoproliferative disease including multiple myeloma; or
any of SEQ ID NO: 138 and 139, SEQ ID NO: 140 and 141, SEQ ID NO: 148 and 149, SEQ ID NO: 150 and 151 or SEQ ID NO: 152 and 153 when said disease is any myeloid neoplasm including acute myeloid leukemia.

11. The method according to claim 1, wherein said primers are selected from any of SEQ.ID.NO. 39 to SEQ.ID.NO. 137, SEQ.ID.NO. 138 and 139, SEQ.ID.NO. 140 and 141, SEQ.ID.NO. 148 and 149, SEQ.ID.NO. 150 and 151, or SEQ.ID.NO. 152 and 153.

12. The method according to claim 1, wherein said therapy is chemotherapy and:
when said disease is multiple myeloma and the level of MRD is $>10^{-6}$; or
when said disease is a myeloid neoplasm and the level of MRD is $>10^{-5}$:
steps A and B are repeated,
wherein each repetition of step A comprises administering the same therapy as previously administered to said subject or therapy different to that previously administered to said subject.

13. The method according to claim 12, wherein:
when said disease is multiple myeloma and the level of MRD is $>10^{-5}$; or
when said myeloid neoplasm is acute myeloid leukemia and the level of MRD is $>2.5\times10^{-4}$:
steps A and B are repeated.

14. The method according to claim 1, wherein:
when said disease is multiple myeloma and said therapy is chemotherapy which consists of between 9 and 18 cycles of treatment, each cycle comprising administration of bortezomib plus melphalan and prednisone (VMP) and lenalidomide plus dexamethasone (Rd), and the level of MRD is calculated according to either of the following formulae:

$$MRD=(L_c\times k)/(L_t\times D)$$

or $$MRD=L_c\times(D/k)/L_t^2; \text{ and}$$

when said disease is acute myeloid leukemia and said therapy is chemotherapy which consists of:
1 or 2 cycles of treatment, each cycle comprising administration of cytarabine over 7 days and subsequent administration of an anthracycline antibiotic or an anthracenedione over 3 days; or
1 or 2 cycles of treatment, each cycle comprising administration of cytarabine over 7 days and subsequent administration of an anthracycline antibiotic or an anthracenedione over 3 days, followed by 1 or 2 cycles of treatment each comprising administration of cytarabine,
and the level of MRD is calculated according to the following formula:

$$MRD=L_c/L_t,$$

and
when said disease is multiple myeloma and said therapy is chemotherapy which consists of between 9 and 18 cycles of treatment, each cycle comprising administration of bortezomib plus melphalan and prednisone (VMP) and lenalidomide plus dexamethasone (Rd), and the level of MRD is calculated according to either of the following formulae:

$$MRD=(L_c\times k)/(L_t\times D)$$

or $$MRD=L_c\times(D/k)/L_t^2$$

and is $>10^{-5}$; or
when said disease is acute myeloid leukemia and said therapy is chemotherapy which consists of 1 or 2 cycles of treatment, each cycle comprising administration of cytarabine over 7 days and subsequent administration of an anthracycline antibiotic or an anthracenedione over 3 days, and the level of MRD is calculated according to the following formula:

$$MRD=L_c/L_t$$

and is $>10^{-3}$; or
when said disease is acute myeloid leukemia and said therapy is chemotherapy which consists of 1 or 2 cycles of treatment, each cycle comprising administration of cytarabine over 7 days and subsequent administration of an anthracycline antibiotic or an anthracenedione over 3 days, followed by 1 or 2 cycles of treatment each comprising administration of cytarabine, and the level of MRD is calculated according to the following formula:

$$MRD=L_c/L_t$$

and is $>2.5\times10^{-4}$,
steps A and B are repeated, wherein each repetition of step A comprises administering the same chemotherapy as previously administered.

15. The method according to claim 14, wherein the anthracycline antibiotic or anthracenedione is idarubicin.

* * * * *